US012753392B2

(12) United States Patent
Westenfelder et al.

(10) Patent No.: US 12,753,392 B2
(45) Date of Patent: *Oct. 6, 2026

(54) NEO-ISLETS COMPRISING STEM AND ISLET CELLS AND TREATMENT OF DIABETES MELLITUS THEREWITH

(71) Applicant: SymbioCellTech, LLC, Salt Lake City, UT (US)

(72) Inventors: Christof Westenfelder, Salt Lake City, UT (US); Anna Gooch, Salt Lake City, UT (US); Ping Zhang, Salt Lake City, UT (US); Zhuma Hu, Salt Lake City, UT (US)

(73) Assignee: SymbioCellTech LLC, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/934,263

(22) Filed: Sep. 22, 2022

(65) Prior Publication Data

US 2023/0033991 A1 Feb. 2, 2023

Related U.S. Application Data

(63) Continuation of application No. 15/261,750, filed on Sep. 9, 2016, now Pat. No. 11,485,954.

(60) Provisional application No. 62/264,238, filed on Dec. 7, 2015, provisional application No. 62/216,920, filed on Sep. 10, 2015.

(51) Int. Cl.

| | |
|---|---|
| ***C12N 5/071*** | (2010.01) |
| ***A61K 31/436*** | (2006.01) |
| ***A61K 35/28*** | (2015.01) |
| ***A61K 35/39*** | (2015.01) |
| ***A61K 45/06*** | (2006.01) |
| ***C12N 5/00*** | (2006.01) |
| ***C12N 5/0775*** | (2010.01) |
| *A61K 9/00* | (2006.01) |

(52) U.S. Cl.

CPC .......... *C12N 5/0676* (2013.01); *A61K 31/436* (2013.01); *A61K 35/28* (2013.01); *A61K 35/39* (2013.01); *A61K 45/06* (2013.01); *C12N 5/0012* (2013.01); *C12N 5/0663* (2013.01); *C12N 5/0667* (2013.01); *C12N 5/0677* (2013.01); *A61K 9/0019* (2013.01); *C12N 2502/1358* (2013.01); *C12N 2502/1382* (2013.01)

(58) Field of Classification Search

None

See application file for complete search history.

(56) References Cited

U.S. PATENT DOCUMENTS

| | | | |
|---|---|---|---|
| 8,372,641 | B2 | 2/2013 | Westenfelder |
| 2007/0031384 | A1 | 2/2007 | Atala et al. |
| 2011/0045077 | A1 | 2/2011 | Weir et al. |
| 2011/0129918 | A1 | 6/2011 | Hung |
| 2012/0214230 | A1 | 8/2012 | Anneren et al. |
| 2013/0095081 | A1 | 4/2013 | March et al. |
| 2014/0105867 | A1 | 4/2014 | Grant et al. |
| 2014/0212395 | A1 | 7/2014 | Hornstein et al. |
| 2014/0303079 | A1 | 10/2014 | Petersen et al. |

FOREIGN PATENT DOCUMENTS

| | | | |
|---|---|---|---|
| JP | 2013507959 | A | 3/2013 |
| JP | 6771567 | B2 | 10/2020 |
| WO | 2011049524 | A1 | 4/2011 |
| WO | 2011133718 | A1 | 10/2011 |
| WO | 2012112982 | A2 | 8/2012 |
| WO | 2015058139 | A1 | 4/2015 |
| WO | 2017044847 | A1 | 3/2017 |

OTHER PUBLICATIONS

Shin et al., Tissue Eng. Part A 21(5-6): 1024-1035 (2015; published online Jan. 30, 2015).*

Huang et al., Cell Transplantation 27(7): 1017-1026 (2018).*

"Stochastic." Merriam-Webster.com Dictionary, Merriam-Webster, https://www.merriam-webster.com/dictionary/stochastic. Accessed Apr. 23, 2025. (Year: 2025).*

(Continued)

*Primary Examiner* — Allison M Fox

(74) *Attorney, Agent, or Firm* — Patent Law Works

(57) ABSTRACT

Described are Neo-Islets comprising: a) dedifferentiated islet cells and mesenchymal and/or adipose stem cells; or b) redifferentiated islet cells and mesenchymal and/or adipose stem cells where the cells have been treated so as to facilitate redifferentiation. Further described herein are methods of generating Neo-Islets, the methods comprising: culturing a) dedifferentiated islet cells and mesenchymal and/or adipose stem cells; or b) redifferentiated islet cells and mesenchymal and/or adipose stem cells; on a surface that promotes the formation of cell clusters. Also described are methods of treating a subject, the methods comprising: providing to the subject Neo-Islets described herein. Additionally described are methods of treating a subject suffering from Type 1 Diabetes Mellitus, Type 2 Diabetes Mellitus, and other types of insulin-dependent diabetes mellitus, or impaired glucose tolerance by providing to the subject Neo-Islet as described herein. Additionally described are methods of treatment in which intraperitoneal administration of islet-sized Neo-Islets composed of high numbers of mesenchymal stem cells and cultured islet cells, durably and reversibly treats, without hypoglycemia, both streptozotocin-induced and spontaneous Type 1 Diabetes Mellitus, Type 2 Diabetes Mellitus, and other types of insulin-dependent diabetes mellitus, or impaired glucose tolerance.

9 Claims, 29 Drawing Sheets
(9 of 29 Drawing Sheet(s) Filed in Color)

(56) References Cited

OTHER PUBLICATIONS

Bar, et al. Redifferentiation of Expanded Human Pancreatic β-Cell-derived Cells by Inhibition of the Notch Pathway, J Biol Chem. 287(21): 17269-17280, Mar. 28, 2012.

Bassi, E. J, et al. "Immune Regulatory Properties of Allogeneic Adipose-Derived Mesenchymal Stem Cells in the Treatment of Experimental Autoimmune Diabetes." Diabetes (New York, N.Y.), vol. 61, No. 10, 2012, pp. 2534-2545.

Buder, Brian, et al. "Encapsulated Islet Transplantation: Strategies and Clinical Trials." Immune Network, vol. 13, No. 6, 2013, pp. 235-239.

Burr S.P., F. Dazzi, O. Garden: Mesenchymal stromal cells and regulatory T cells: the Yin and Yang of peripheral tolerance Immunol. Cell Biol. 91:12-8, 2013.

Canadian Intellectual Property Office Office Action and Examination Search Report, Application No. 2,995,599, Dated Mar. 11, 2019, 4 pages.

Chao et al., A novel Human Stem Cell coculture System that Maintains the Survival and Function of culture Islet-Like Cell Clusters, Cell transplantation, Jun. 1, 2008, pp. 657-664, DOI: 10.3727/096368908786092801 Retrieved from the Internet: URL:https://journals.sagepub.com/doi/pdf/10.3727/096368908786092801.

Crop M.J., C.C. Baan, S.S. Korevaar, J.N.M. IJzermans, I.P.J. Alwayn, W. Weimar, and M.J. Hoogduijn: Donor-Derived Mesenchymal Stem Cells Suppress Alloreactivity of Kidney Transplant Patients. Transplantation 87:896-906, 2009.

Delarosa O., B. Sanchez-Correa, S. Morgado, C. Ramirez, B. del Rio, R. Menta, E. Lombardo, R. Tarazona, and J.G. Casado: Human Adipose-Derived Stem Cells Impair Natural Killer Cell Function and Exhibit Low Susceptibility to Natural Killer-Mediated Lysis. Stem Cells Dev. 21:1333-1343, 2012.

Dominici, M, et al. "Minimal Criteria for Defining Multipotent Mesenchymal Stromal Cells. The International Society for Cellular Therapy Position Statement." Cytotherapy, vol. 8, No. 4, 2006, pp. 315-317.

English, K, Mechanisms of mesenchymal stromal cell immunomodulation. Immunol. Cell Biol., Abstract, 91:19-26, 2012.

Extended European Search Report Communications , Application No. 16845186.2, Mail date Jan. 8, 2019, 9 pages.

Hara, M., X. Wang, T. Kawamura, V.P. Bindokas, R.F. Dizon, S.Y. Alcoser, M.A. Magnuson, and G.I. Bell: Transgenic mice with green fluorescent protein-labeled pancreatic beta-cells. Am. J. Physiol. Endocrinol. Metab. 284:E177-E183, 2003.

Japanese Office Action, Application No. 2018532519, dated Apr. 15, 2019, with translation, 9 pages.

Japanese Office Action, Application No. 2018532519, dated Dec. 23, 2019, with translation, 9 pages.

Joglekar, M. V., Hardikar, A. (2010). Epithelial-to-mesenchymal transition in pancreatic islet β cells. Cell Cycle, 9 (20), 4077-4079. https://doi.org/10.4161/cc.9.20.13590.

Karaoz, et al. "Adipose Tissue-derived Mesenchymal Stromal Cells Efficiently Differentiate into Insulin-producing Cells in Pancreatic Islet Microenvironment Both in Vitro and in Vivo." Cytotherapy 15, No. 5 (2013): 557-70.

Karaoz, et al. "Bone Marrow-derived Mesenchymal Stem Cells Co-cultured with Pancreatic Islets Display Beta Cell Plasticity." Journal of Tissue Engineering And Regenerative Medicine 5, No. 6 (2011): 491-500.

Kim, Y.-H, et al., Interleukin (IL)-10 induced by CD11b(+) cells and IL-10-activated regulatory T cells play a role in immune modulation of mesenchymal stem cells in rat islet allografts. Mol. Med. 17:697-708, 2011.

Lange, C., F. Tögel, H. Ittrich, F. Clayton, C. Nolte-Ernsting, A.R. Zander, and C. Westenfelder: Administered mesenchymal stem cells enhance recovery from ischemia/reperfusion-induced acute renal failure in rats. Kidney Int. 68:1613-7, 2005.

Le Blanc, K., L.C. Davies: Mesenchymal stromal cells and the innate immune response. Immunol. Lett. in press: May 15, 2015. pii: S0165-2478(15)00072-3. doi: 10.1016/j.imlet.2015.05.004.

Merck Manual, 18th Edition, Japanese version, 2007, p. 1346-1348. English translation taken from Merck Manual Professional Version website (https://www.merckmanuals.com/professional). Brutsaert, Erika F, MD, Diabetes Mellitus (DM), New York Medical College (2019), 9 pgs.

Ouziel-Yahalom, Limor, et al. "Expansion and Redifferentiation of Adult Human Pancreatic Islet Cells." Biochemical and Biophysical Research Communications, vol. 341, No. 2, 2006, pp. 291-298.

PCT International Search Report and Written Opinion for International Application No. PCT/US2016/051105, mailed Dec. 8, 2016, 3 pages.

Pittenger M.F., A.M. Mackay, S.C. Beck, R.K. Jaiswal, R. Douglas, J.D. Mosca, M.A. Moorman, D.W. Simonetti, S. Craig, and D.R. Marshak: Multilineage potential of adult human mesenchymal stem cells. Science 284:143-7, 1999.

Plock J.A., et al., Adipose- and Bone Marrow-Derived Mesenchymal Stem Cells Prolong Graft Survival in Vascularized Composite Allotransplantation. Transplantation, Abstract, 99(9):1765-73: 2015.

Prabakar, Kamalaveni R, et al. "Generation of Glucose-Responsive, Insulin-Producing Cells from Human Umbilical Cord Blood-Derived Mesenchymal Stem Cells." Cell Transplantation, vol. 21, No. 6, 2012, pp. 1321-1339.

Russ, et al. "Epithelial-Mesenchymal Transition in Cells Expanded In Vitro from Lineage-Traced Adult Human Pancreatic Beta Cells." PLoS ONE 4, No. 7 (2009): E6417.

Russ, et al., InsulinProducing Cells Generated from Dedifferentiated Human Pancreatic Beta Cells Expanded In Vitro, PLoS ONE, vol. 6, issue 9, pp. 1-12, Sep. 30, 2011.

Scuteri, et al. A Double Mechanism for the Mesenchymal Stem Cells Positive Effect on Pancreatic Islets, PLoS ONE, vol. 9, issue 1, pp. 1-8, Jan. 8, 2014.

Spaggiari G.M., L. Moretta: Cellular and molecular interactions of mesenchymal stem cells in innate immunity. Immunol. Cell Biol., Abstract, 91:27-31, 2013.

Third Part Preissuance Submission of Information Disclosure Statement, U.S. Appl. No. 15/261,750, filed Sep. 9, 2018, 1 pg.

Tögel F., K. Weiss, Y. Yang, Z. Hu, P. Zhang, and C. Westenfelder: Vasculotropic, paracrine actions of infused mesenchymal stem cells are important to the recovery from acute kidney injury. Am. J. Physiol. Renal Physiol. 292: F1626-35, 2007.

Tögel F., Z. Hu, K. Weiss, J. Isaac, C. Lange, and C. Westenfelder: Administered mesenchymal stem cells protect against ischemic acute renal failure through differentiation-independent mechanisms. Am. J. Physiol. Renal Physiol. 289:F31-42, 2005.

Vrabelova D., C.A. Adin, A. Kenzig, C. Gilor, F. Xu, J.L. Buss, A. Rajab: Evaluation of a high-yield technique for pancreatic islet isolation from deceased canine donors. Domest. Anim. Endocrinol. 47:119-26, 2014.

Westenfelder, C. et al. (2017), Durable Control of Autoimmune Diabetes in Mice Achieved by Intraperitoneal Transplantation of "Neo-Islets," Three-Dimensional Aggregates of Allogeneic Islet and "Mesenchymal Stem Cells". Stem Cells Translational Medicine, 6: 1631-1643. doi:10.1002/sctm.17-0005.

Woolcott O.O., et al., Simplified method to isolate highly pure canine pancreatic islets. Pancreas 41:31-8, 2012.

Zhou, X., et al., Cell Fusion Connects Oncogenesis with Tumor Evolution. Am. J. Pathol. 185:2049-60, 2015.

* cited by examiner

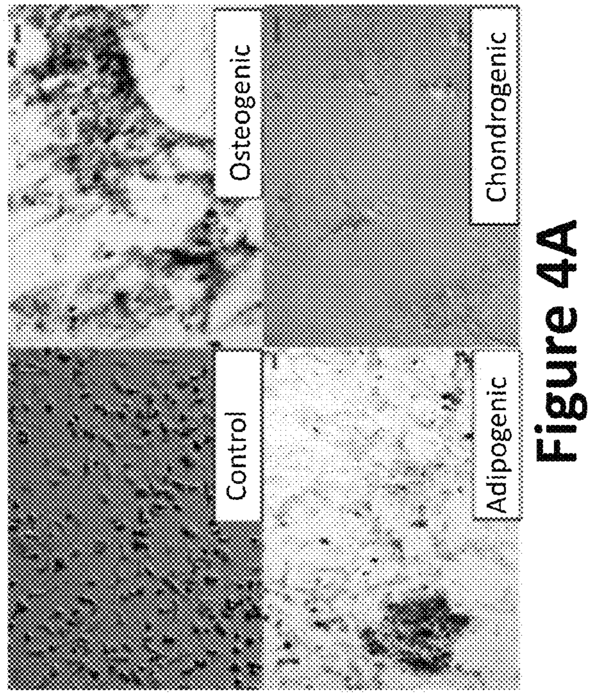
Figure 4A
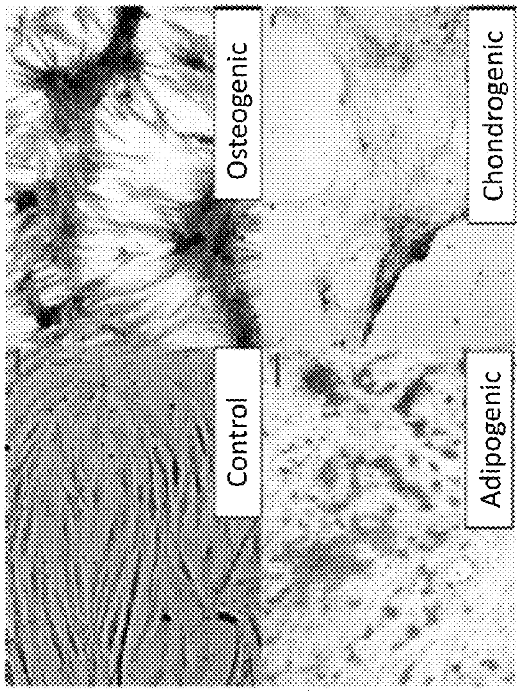
Figure 4B
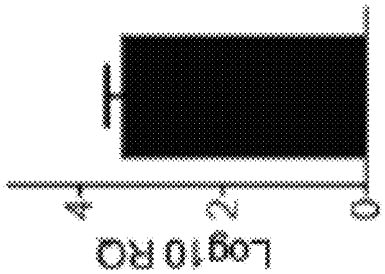
Figure 4C
| Cell Surface Epitopes | C57Bl/6 Mouse ASCs (n=3) | Dog ASCs (n=7) |
|---|---|---|
| CD34 | - | - |
| CD44 | + | + |
| CD45 | - | - |
| CD90 | + | - |
| CD105 | + | - |
| I-A[b]/DLA-DR | - | - |
-, negative: <5%; +, positive > 95%
Figure 4D Figure 7A
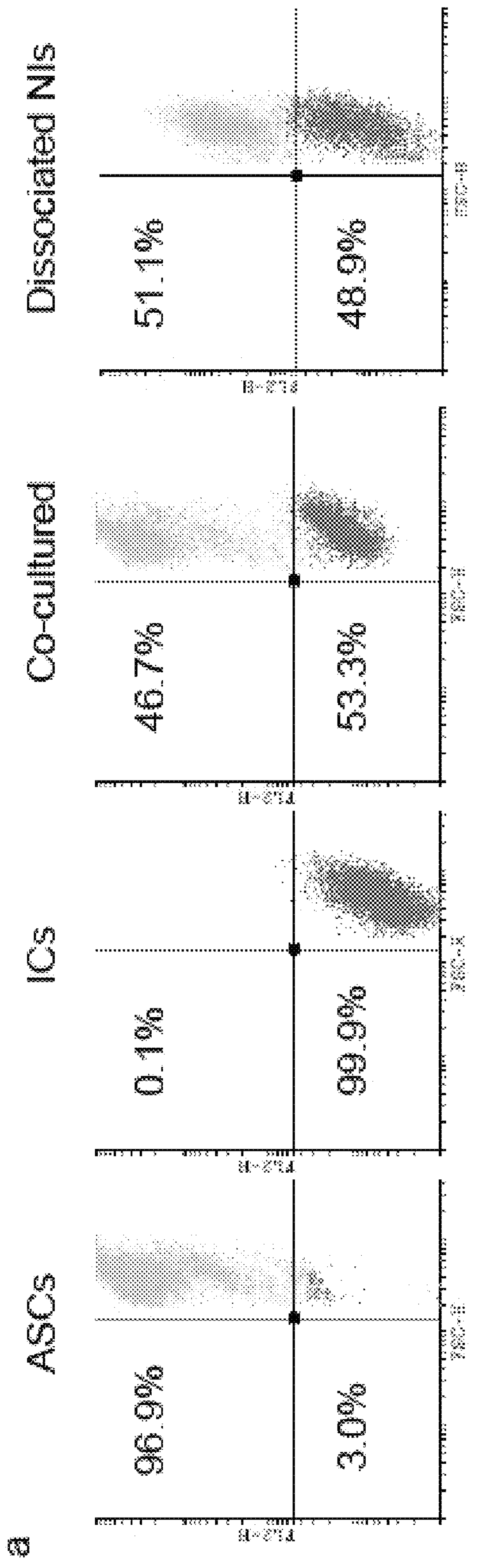
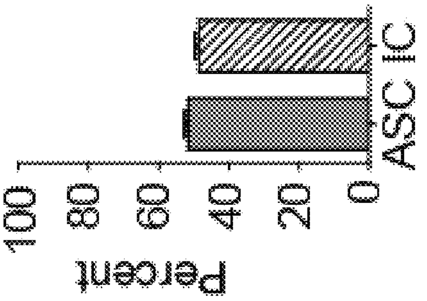
Figure 7B

Gene expression profiles of redifferentiated MOUSE Symbions (left) and freshly isolated MOUSE Islets (right) normalized to freshly formed MOUSE Symbions

Gene expression profiles of redifferentiated DOG Symbions (left) and freshly isolated DOG Islets (right) normalized to freshly formed DOG Symbions

GSIS by 50 mouse Islets (open bars, left y-axis) vs. 50 mouse Symbions (cross hatched bars, right y-axis)

Figure 10A
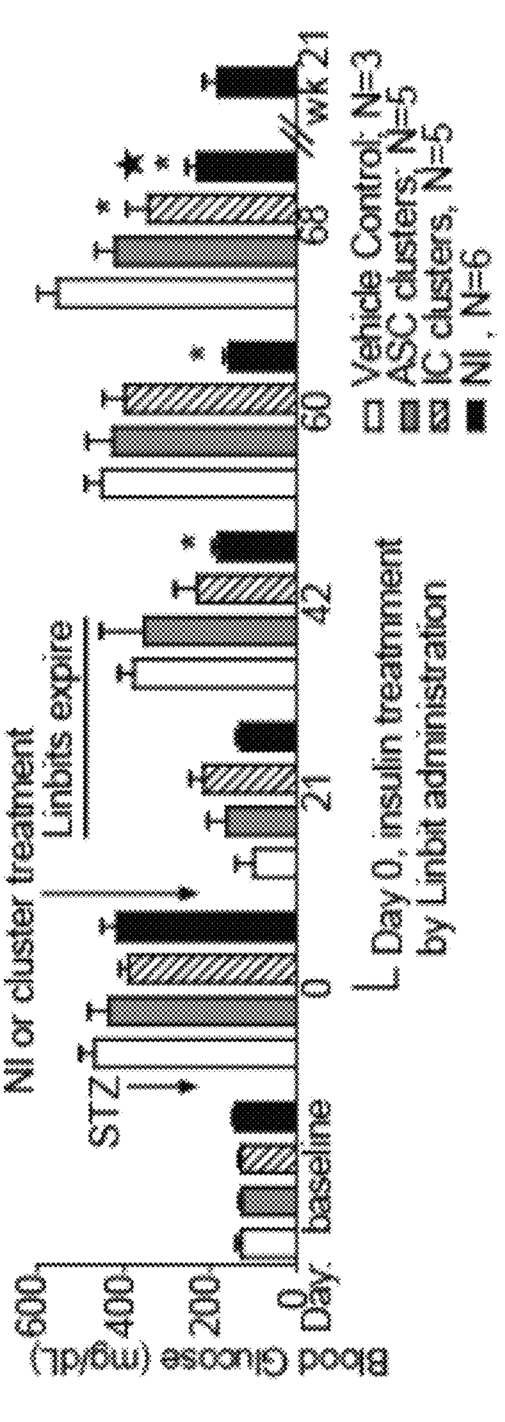
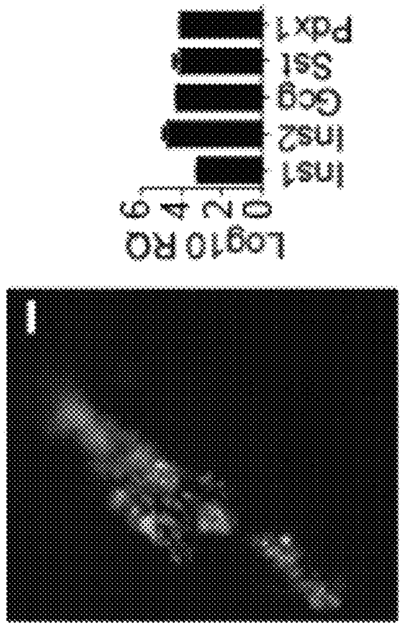
Figure 10B
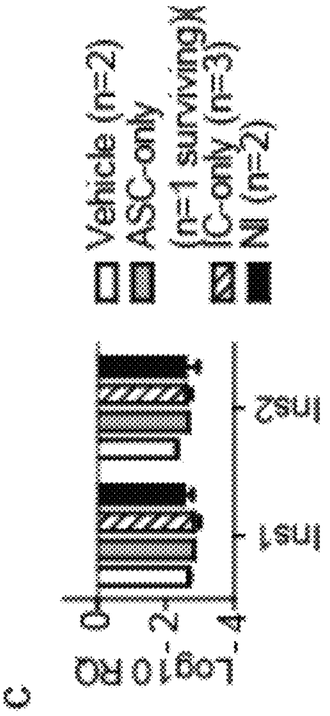
Figure 10C

*, Differences between treated and control groups are statistically significant; P < 0.05.

Kaplan-Meier Plot: Survival of early Symbion-treated vs. control NOD/SCID mice

*, Differences between Symbion-treated and Controls are statistically significant, P = 0.03.

*, Differences between treatment and control groups are statistically significant; P< 0.05.

*, Differences between treated and control groups are statistically significant; $P < 0.05$.

Figure 23

| Serum from NOD mice treated with | Percent Positive (cy3 positive) IgG Response (mean ± SE) to | | |
|---|---|---|---|
| | C57Bl/6 MSCs | C57Bl/6 cultured Islet Cells | C57Bl/6 intact islets |
| Vehicle (N=3) | 1.1±0.2 | 5.5±1.3 | 1.7±1.7 |
| C57Bl/6 NIs (N=3) | 0.8 ± 0.1 | 1.0±0.2 | NA |
| C57Bl/6 islets (N=3, positive control) | NA | NA | 32.0±6.1* |
| IgG Isoptye antibody control | 0.3 | 0.1 | NA |

NA, not applicable; PE, Phycoerythrin

NEO-ISLETS COMPRISING STEM AND ISLET CELLS AND TREATMENT OF DIABETES MELLITUS THEREWITH

CROSS-REFERENCE TO RELATED APPLICATION

This application is a continuation of U.S. patent application Ser. No. 15/261,750, filed Sep. 9, 2016, pending, which claims the benefit of U.S. Provisional Patent Application Ser. No. 62/216,920, filed Sep. 10, 2015, and U.S. Provisional Patent Application Ser. No. 62/264,238, filed Dec. 7, 2015, the disclosure both of which are hereby incorporated herein in its entirety by this reference.

TECHNICAL FIELD

The application relates to the field of biotechnology, medicine, and cell culture. It specifically relates to, e.g., methods of producing compositions (also identified as "Neo-Islets" or "cell clusters") that include stem cells and islet cells. It also relates to the utilization of Neo-Islets comprising stem cells and islet cells for treatment of, for example, insulin-dependent diabetes mellitus, noninsulin-dependent diabetes mellitus, or impaired glucose tolerance.

BACKGROUND

Insulin-producing β-Cells, when isolated from a donor pancreas, generally proliferate very poorly ex vivo, i.e., not sufficiently to generate adequate cell numbers for the treatment of insulin-dependent diabetes mellitus. Current technologies and many preclinical therapies designed to overcome this shortage and provide diabetic patients with a long-lasting, physiologically released insulin replacement therapy (islet and pancreas transplants; precursor cell-derived therapies, etc.) are hampered both by the shortage of donor cells and the need to suppress the patient's immune system, leading to a new set of adverse effects for the patient, such as opportunistic infections and malignancies. The great shortage of suitable pancreas donors combined with the need for repeated islet transplants, requiring up to five donors each, continues to prevent the general availability of these expensive therapies. Micro- and macro-encapsulation systems of insulin-producing cells are tested to facilitate immune isolation and overcome this problem. However, the utilized encapsulation materials represent foreign bodies and can induce an auto-immune response that will result in the failure of the therapy or require prolonged use of anti-rejection drugs.

BRIEF SUMMARY

Described herein are Neo-Islets comprising: a) dedifferentiated islet cells and mesenchymal and/or adipose stem cells; or b) redifferentiated islet cells and mesenchymal and/or adipose stem cells.

Further described herein are methods of generating a Neo-Islet, the methods comprising: culturing a) dedifferentiated islet cells and mesenchymal and/or adipose stem cells; or b) redifferentiated islet cells and mesenchymal and/or adipose stem cells, on a surface that promotes/allows the formation of Neo-Islets. In embodiments, the surface is a hydrophobic and/or ultra-low adhesion surface.

Also described are methods of treating a subject, the methods comprising: providing to the subject the Neo-Islets described herein. Additionally described are methods of treating a subject suffering from Type 1 Diabetes Mellitus or Type 2 Diabetes Mellitus, by, e.g., providing to the subject Neo-Islets as described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 4A-4D. Mouse (FIG. 4A) and canine (FIG. 4B) ASC phenotyping. FIGS. 4A and 4B, left upper panels: bright field images of plastic adherent, confluent ASC cultures; Right upper panels: Osteogenic differentiation (calcium staining with Alizarin Red); Left lower panels: adipogenic differentiation (Oil Red-O staining); Right lower panels: Chondrogenic differentiation (Alcian blue staining). Red scale bars=50 μm. FIG. 4C: IDO-1 gene expression of canine ASCs exposed to IFNγ normalized to that of unexposed cASCs (mean±SEM of 4 independent experiments). IDO-1 gene expression is stimulated 3.4-fold when canine ASCs are exposed to IFNγ. FIG. 4D: Cultured mouse and dog ASCs were examined by FACS for their positive expression of CD44, and negative expression of CD45, CD34 and I-A[b] and DLA-DR transplant antigens. While all M/ASCs are characterized by plastic adherence and ability to undergo trilineage differentiation, not all non-human M/ASCs express the same set of cell surface epitopes as those from humans, and while most express CD44, expression of CD90 is variable. Canine M/ASC expression of CD90 is variable.

FIG. 3A depicts images and a schematic of mouse cells undergoing Neo-Islet formation, wherein 1) green fluorescent protein positive (gfp+) mouse MSCs are culture expanded; 2) Mouse islet cells are culture expanded; 3) the cells are co-cultured in ultra-low-adhesion plates and readily form Neo-Islets. The Neo-Islets can subsequently be cultured in redifferentiation medium (RDM).

FIGS. 7A and 7B. Percent of Cell Tracker Green stained dog ASCs and unstained dog ICs in cNIs prior to and post formation. FIG. 7A: Representative FACS scatter plots (x=forward scatter; y=fluorescence) showing the percent of green and unstained (i) ASCs alone (far left panel), (ii) ICs alone (left middle panel) (iii) cells at initiation of co-culture (right middle panel), (iv) dissociated NIs formed from the co-culture in (iii; far right panel) 24 hrs. post-co-culture collected and dissociated to single cell preparation. 96.9% of the ASCs were effectively stained green prior to co-culture and only 0.1% of the unstained ICs are autofluorescent. Upon initiation of co-culture, approximately 47% of the cells are ASC and 53% are ICs, and after formation, within the NIs, approximately 51% of the cells are ASCs and 49% are ICs. FIG. 7B: Bar graph of the percent of ASCs and ICs in NIs 24 hrs. post-coculture (mean±SEM) of n=12 independent repetitions of the experiment conducted in FIG. 7A, indicating that consistently, NIs are composed of approximately 50% ICs and 50% ASCs. Differences between bars are not statistically significant.

FIG. 8A: Gene expression profile of islet associated genes in mouse (top) and dog (bottom) Neo-Islets. Gene expression profiles were obtained from redifferentiated mouse Neo-Islets (top left), freshly isolated mouse islets (top right), and freshly formed mouse Neo-Islets (mouse normalization) on the following 14 islet associated genes: insulin 1 (ins1), insulin 2 (ins2), glucagon (gcg), somatostatin (sst), pancreatic duodenal homeobox-1 (pdx1), Insulin transcription factor mafA (mafa), nk6 homeobox 1 (nkx6.1), pancreatic polypeptide (ppy), glut-1, glut-2, ucn3, kcj11, sur2 and glp1 receptor (glp1r). Gene expression profiles were obtained from redifferentiated dog Neo-Islets (bottom left), freshly isolated dog islets (bottom right), and freshly formed dog Neo-Islets (dog normalization) on the following 6 islet associated genes: insulin (ins), gcg, sst, nkx6.1, sur1, and glp1r. Both freshly formed mouse and dog Neo-Islets express low levels of all tested islet associated genes, and have the capacity to undergo redifferentiation resulting in higher levels of these genes. FIG. 8B: Top: Gene expression profiles for insulin 1 (ins1), insulin 2 (ins2), glucagon (gcg), somatostatin (sst), pancreatic polypeptide (ppy), pancreatic duodenal homeobox-1 (pdx1), Insulin transcription factor mafA (mafa), glucose transporter 2 (glut-2), vascular endothelial growth factor α (vegf-α) and stromal cell derived factor 1 (cxcl-12) were obtained from freshly formed mouse Neo-Islets generated from either P1 mouse islet cells and P5 mouse MSCs (left), or P2 mouse islet cells and P5 mouse MSCs (right), and normalized to freshly isolated mouse islets. Middle: gene expression profiles of islet cell associated genes, insulin (ins), gcg, pdx1 and sulfonylurea receptor 1 (sur1), as well as ASC associated genes vegf-α, cxcl12, and transforming growth factor β1 (tgfβ-1) in freshly formed canine Neo-Islets produced from either P1 dog islet cells and P2 dog ASCs (left) or P2 dog islet cells and P2 dog ASCs (right) and normalized to fresh dog islets. Bottom: Gene expression profile for ins, gcg, sst, ppy, pdx1, mafa, nk6 homeobox 1 (nkx6.1), urocortin 3 (ucn3), sur1, vegf-α, cxcl12, tgfβ-1, and igf-1 in freshly formed human Neo-Islets generated from either P1 human islet cells and P3 human ASCs (left) or P2 human islet cells and P2 human ASCs (right) normalized to freshly isolated human islets. This panel demonstrates that across species (murine, canine, human), (a) Neo-Islets made from dedifferentiated, passaged islet cells express low levels of islet cell genes, and (b) islet cell gene expression decreases with passaging. FIG. 8C: Glucose Stimulated Insulin Secretion (GSIS) by 50 freshly formed C57Bl/6 mouse Neo-Islets comprising dedifferentiated P1 islet cells and P5 MSCs (cross hatched bars) vs. 50 freshly isolated C57Bl/6 mouse islets (open bars). Experiments were performed in duplicate. Neo-Islets release approximately 1% of the insulin that freshly isolated islets do in response to exposure to 25 mM glucose for 60 minutes (~0.5 ng vs. ~50 ng Insulin). This parallels the decrease in insulin gene expression over passages seen in Panel B.

FIGS. 10A-10C. Blood glucose levels of NI and cluster treated, STZ diabetic C57Bl/6 mice and in vivo redifferentiation of ICs into endocrine cells contained in the NIs. FIG. 10A: Blood glucose levels over time are shown in groups of STZ-diabetic mice all treated i.p. on Day 7 with (i) vehicle, (ii) $2\times10^5$ ASC clusters/kg b.wt, (iii) $2\times10^5$ IC clusters/kg b.wt. or (iv) $2\times10^5$ NIs/kg b.wt. *, P<0.05 vs. vehicle-treated group. *, P<0.05 vs. ASC-cluster treated group. FIG. 10B: Left, Fluorescence image (green, eGFP+ cells) of a representative omentum from an NI-treated, euglycemic mouse 21 weeks post NI injection (scale bar=200 μm). Right, omental gene expression (mean±SEM) normalized to that of NIs prior to administration, demonstrating NI engraftment, and significant endocrine redifferentiation. FIG. 10C: Ins 1 and Ins2 expression profiles (mean±SEM) from whole pancreata of ASC-cluster, IC-cluster, and NI treated vs. vehicle-treated diabetic mice normalized to those of non-diabetic mice. Since pancreatic insulin gene expression levels were similarly decreased in all treatment groups vs. those of hyperglycemic, vehicle-treated mice, it follows that the blood glucose control seen in NI-treated mice was achieved by insulin secretion from omental NIs.

FIG. 14A: Blood glucose levels over time of STZ-diabetic C57Bl/6 mice treated i.p. with $2\times10^5$ syngeneic NIs/kg b.wt. (black bars, N=6) or vehicle (open bars, N=6). FIG. 14B: Blood glucose levels of STZ-diabetic NOD/SCID mice treated with either $2\times10^5$ canine NI/kg b.wt. (black bars, N=5) or vehicle (open bars, N=5). In both FIGS. 14A and 14B, blood glucose levels were first normalized on Day zero with Linbit pellets prior to NI administration. While vehicle-treated mice become hyperglycemic once insulin is depleted from the Linbits (30-40 days post implantation), NI treated mice (syn- and xenogeneic) remain normoglycemic, indicating NIs control blood glucose levels long term. *, P <0.05 vs. vehicle-treated groups.

FIG. 18A: Fluorescence in vivo imaging of a NOD mouse treated 10 weeks previously with DiR labeled, eGFP+ NIs demonstrates their location in the upper abdomen. FIG. 18B: eGFP+C57Bl/6 mouse NIs given i.p. remained engrafted in the omentum and maintained euglycemia in spontaneously diabetic NOD mice at 11 weeks post treatment (see FIG. 9). Left image (10×): representative omentum of a NOD mouse treated with C57Bl/6 eGFP+ NIs (green; see red arrows). This image demonstrates that the NIs homed to and engrafted in the omentum, and indicates there is no rejection of the NIs. Right image (10×): enlarged image of a single, engrafted NI. Its location, close to capillaries (yellow arrow) is shown. FIG. 18C: Left panel, Main image: Sections of the omentum (10× image) depicted in FIG. 18B stained by immunohistochemistry for DNA (Dapi, blue), and insulin protein (red). Insulin protein was clearly detected. Inset, negative control in which the primary, anti-insulin antibody was omitted. Right panel, Main image: Sections of the omentum (10×) of a vehicle treated, diabetic NOD mouse stained for DNA (blue), and insulin protein (red). Inset: 40× magnification of the same section (scale bar=10 μm). No insulin was detected at either magnification. These images demonstrate the omental location and insulin synthesis by engrafted NIs. Scale bars=100 μm unless otherwise indicated.

FIG. 22A: FACS analysis of C57Bl/6 Gfp+ MSCs from Neo-Islets. The top row shows histograms of MSCs stained with isotype antibody (negative control, top left), and MSCs incubated with sera from untreated NOD mice (middle and right). The bottom row shows FACS histograms of MSCs incubated with sera from allo-Neo-Islet-treated (left three panels) or vehicle-treated (right panel) NOD mice. There is no evidence of an antibody response to allogeneic MSCs. FIG. 22B: FACS analysis of C57Bl/6 cultured islet cells from Neo-Islets. The top row shows histograms of islet cells stained with isotype antibody (negative control, top left), and islet cells incubated with sera from untreated NOD mice (middle and right). The bottom row shows FACS histograms of islet cells incubated with sera from allo-Neo-Islet-treated (left three panels) or vehicle-treated (right panel) NOD mice. These data demonstrate that there is no antibody response to allogeneic, cultured islet cells. FIG. 22C: Positive Control. Top histogram: dog ASCs incubated with NOD mouse sera collected 14 days post vehicle treatment, followed by incubation with PE labeled anti-mouse IgG. Bottom histogram: dog ASCs incubated with NOD mouse serum collected 14 days post i.p. treatment with dog ASCs, followed by incubation with PE labeled anti-mouse IgG. These data demonstrate that NOD mice do mount a robust immune response to xenogeneic cells.

FIG. 23: IgG response to the cells used to generate the NIs (MSCs and ICs) that NOD mice were treated with. Shown is a summary of FACS results for P1 C57Bl/6 MSCs and P5 C57Bl/6 cultured ICs incubated with sera and cy3-labeled anti-mouse IgG antibody. Sera were from vehicle-treated and NI-treated NOD mice from the experiment depicted in FIG. 2. Sera were collected at the time of sacrifice (Day 77). As a positive control, sera were also collected from intact C57Bl/6 (allogeneic) islet-treated NOD mice 14 days post i.p. administration of the islets and assessed by FACS as above. Cy3+: percent of Cy3+ cells (mean±SE) detected upon incubation with sera. A response of <7% was considered to be negative. Antibody mediated rejection of NIs appears unlikely since (i) NOD mice remained euglycemic (see FIG. 2), and (ii) FACS data show no IgG response to these cells in otherwise immune competent NOD mice. *, P<0.05 vs. other treatments.

DETAILED DESCRIPTION

Figure 1:
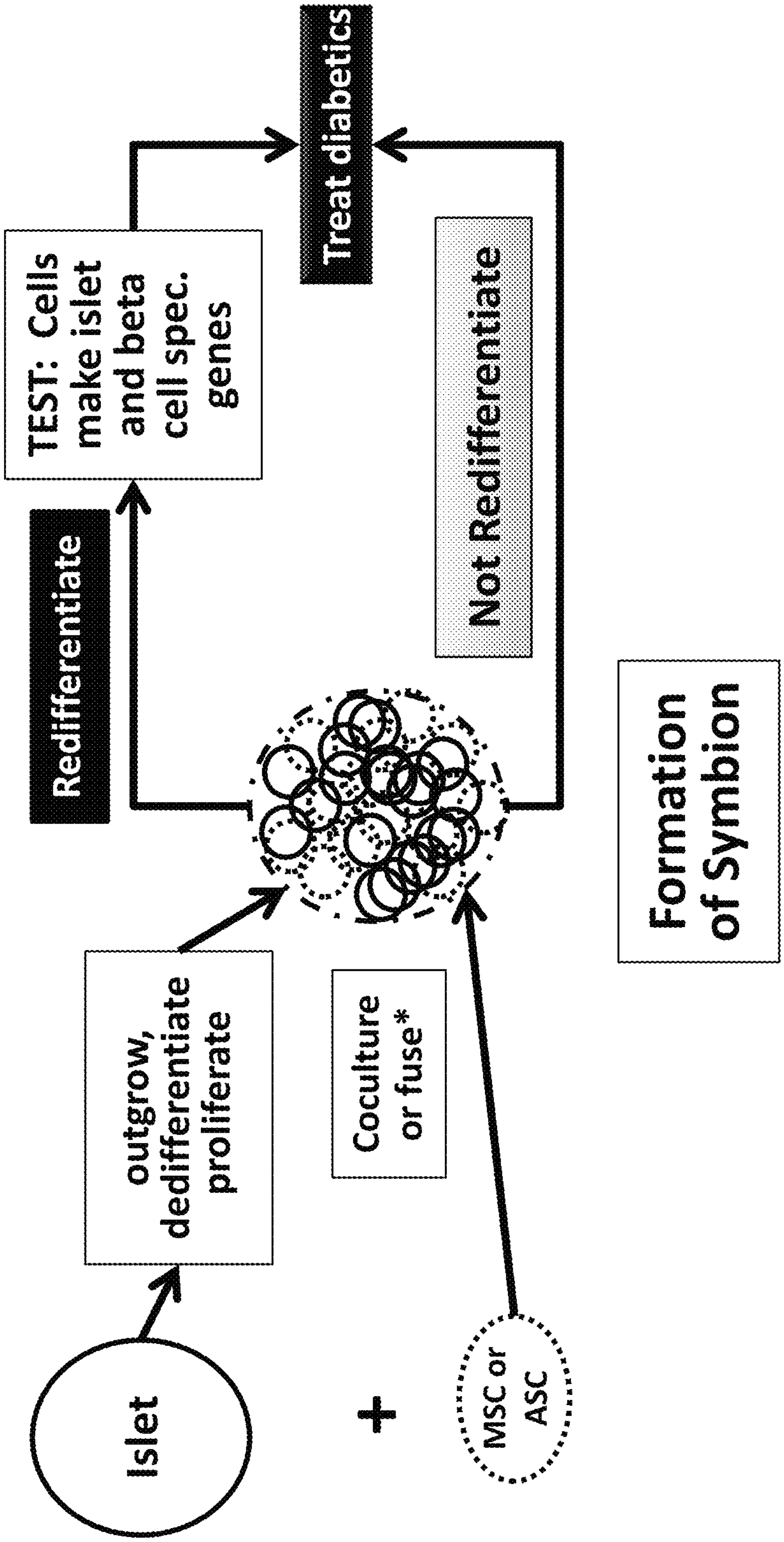
FIG. 1: depicts a schematic overview of Neo-Islet formation and their use in treatment of insulin-dependent diabetes mellitus or noninsulin-dependent diabetes mellitus.

The disclosed methods, cells, and Neo-Islets overcome the limited ability to generate sufficient therapeutic doses of isolated and cultured islet cells from a single pancreas donor and provide them to a subject in need thereof.

As used herein, Islets may comprise any of the cells found in mammalian pancreatic islets, including but not limited to Alpha cells, Beta cells, Delta cells, Gamma cells, and Epsilon cells. In one embodiment Islets comprise at least insulin expressing Beta cells.

As used herein, Neo-Islets may comprise Bone Marrow-derived Mesenchymal Stem Cells and/or Adipose-derived Stem Cells, and dedifferentiated islet cells, and/or redifferentiated islet cells. The redifferentiated islets may comprise any of the cells found in mammalian pancreatic islets, including but not limited to Alpha cells, Beta cells, Delta cells, Gamma cells, and Epsilon cells. Thus, the Neo-Islets hereof preferably produce, among other things, insulin, glucagon, somatostatin, pancreatic duodenal homeobox-1, insulin transcription factor mafA, nk6 homeobox-1, etc. (see, e.g., FIGS. 8A-8C), which might help better regulate glucose and thus explain the surprisingly good results attained herein. In one embodiment, the Neo-Islets comprise at least insulin-expressing Beta cells.

Embodiments include Neo-Islets, generated in vitro, which are the approximate size of pancreatic islets. Such Neo-Islets may comprise Bone Marrow-derived Mesenchymal Stem Cells (MSCs) and/or Adipose-derived Stem Cells (ASCs), dedifferentiated islet cells (which do not express insulin), and/or redifferentiated islet cells. Culture—expanded islet cells that are dedifferentiated via Epithelial-Mesenchymal Transition (EMT), then aggregated with MSCs and/or ASCs into the Neo-Islet cell clusters, which will spontaneously redifferentiate and resume regulated insulin secretion when administered to subjects. Pancreatic islets, like all organs, possess small numbers of MSCs and/or ASCs that intrinsically, as pericytes, exert robust anti-inflammatory, complex immune-protective, survival and tissue repair-supporting actions. Neo-Islets containing dedifferentiated cells may be treated to cause redifferentiation, the redifferentiation resulting in the Neo-Islets comprising redifferentiated islet cells that express insulin. In vitro creation of Neo-Islets, composed of culture expanded islet cells and much higher numbers of healthy MSCs and/or ASCs, enable these Neo-Islets, mediated by the pleiotropic actions of MSCs and/or ASCs, to withstand inflammatory, immune and other insults when administered to subjects with impaired glycemic control, such as Type 1 Diabetes Mellitus, Type 2 Diabetes Mellitus, and other types of insulin-dependent diabetes mellitus, or impaired glucose tolerance.

The MSC/ASC component of the Neo-Islets provides immune isolation, protection, and increased survival of the islet-derived component (the dedifferentiated islet cells or redifferentiated islet cells), thereby preventing rejection and enhancing engraftment of the Neo-Islets. Amplification of the potent immune-modulating activities of normal MSCs and/or ASCs in Neo-Islets provide auto- and allo-immune isolation of islet cells, thereby eliminating the need for anti-rejection drugs or encapsulation devices. Moreover, the MSC/ASC component of the Neo-Islet may induce, via the release of hepatocyte growth and other factors, reversal of the Epithelial to Mesenchymal transition, thus facilitating redifferentiation of dedifferentiated islet cells into insulin producing cells in vivo.

It is generally more efficient to create Neo-Islets of dedifferentiated/redifferentiated islet cells with ASCs or MSCs than it is to fuse the islet cells with ASCs or MSCs in order to immune-isolate the islet cell. While fusing cells is effective, it is highly inefficient, with only approximately 30% of cells becoming fused, and the majority of cells being lost during purification processes. Furthermore, fusion of different cell types has been associated with the development of malignancies, and thus fused cells may not be safe for therapeutic use.[2]

In further embodiments, the Neo-Islets are administered intra-peritoneally (i.p.). The ability of the mammalian omentum to take up foreign bodies and various cell types facilitates the durable and spontaneous engraftment of the Neo-Islets, which then deliver insulin to the subject physiologically, i.e., into the portal vein of the liver, additionally optimized by superior peritoneal glucose sensing to that in the subcutaneous space (see, D. R. Burnett, L. M. Huyett, H. C. Zisser, F. J. Doyle, and B. D. Mensh, "Glucose sensing in the peritoneal space offers faster kinetics than sensing in the subcutaneous space," *Diabetes* 63:2498-505 (2014), incorporated herein by this reference). The physiological route of insulin delivery might reduce insulin resistance, insulin-enhanced lipogenesis and potentially harmful exposure of peripheral tissues to high concentrations of insulin. For these reasons the omentum is uniquely suited for implantation of the Neo-Islets, in addition, should the need arise the Neo-Islets can be removed from the subject via an omentectomy (surgical removal of part or all of the omentum).

In further embodiments, should there be evidence for premature rejection of Neo-Islets, a short initial course with rapamycin will be administered to the subject to improve Neo-Islet survival and function. If a recipient of this therapy lacks or has a damaged omentum, an intra portal vein transplant or a suitable encapsulation device would be utilized.

Methods disclosed included methods for the generation of Neo-Islets.

One non-limiting example of such a method comprises:

a) dedifferentiating islet cells in vitro;
b) placing dedifferentiated islet cells in culture with mesenchymal stem cells and/or adipose-derived stem cells; and
c) forming Neo-Islets of dedifferentiated islet cells and mesenchymal stem cells and/or adipose-derived stem cells.

The dedifferentiated islet cells may be proliferated prior to forming Neo-Islets.

An additional example of such a method comprises:

a) de-differentiating islet cells in vitro;
b) placing de-differentiated islet cells in culture with mesenchymal stem cells or adipose-derived stem cells;
c) forming Neo-Islets of de-differentiated islet cells and mesenchymal stem cells or adipose-derived stem cells; and
d) redifferentiating islet cells in the Neo-Islets in vivo.

The dedifferentiated islet cells may be proliferated before culture with the stem cells to form Neo-Islets.

Yet another example of such a method comprises:

a) dedifferentiating islet cells in vitro;
b) placing dedifferentiated islet cells in culture with mesenchymal stem cells and/or adipose-derived stem cells;
c) forming Neo-Islets of dedifferentiated islet cells and mesenchymal stem cells and/or adipose-derived stem cells; and
d) redifferentiating islet cells in the Neo-Islets in vitro.

The dedifferentiated islet cells may be proliferated before culture with the stem cells to form Neo-Islets.

Another example of such a method comprises:

a) dedifferentiating islet cells in vitro;
b) redifferentiating the islet cells in vitro;
c) placing redifferentiated islet cells in culture with mesenchymal stem cells and/or adipose-derived stem cells; and
d) forming Neo-Islets of redifferentiated islet cells and mesenchymal stem cells and/or adipose-derived stem cells.

The dedifferentiated islet cells may be proliferated prior to redifferentiation.

In each of the above examples of methods, Neo-Islets may be coated with hydrogel. Such coating may be performed after any step in which a Neo-Islet is formed or prior to infusing or providing Neo-Islets to a subject.

In each of the above examples of methods, Neo-Islets may be contained within an encapsulation device. Such encapsulation may be performed after any step in which a Neo-Islet is formed or prior to infusing or providing Neo-Islets to a subject In various embodiments, the Neo-Islets may be immune privileged. As used herein, "immune privileged" refers to Neo-Islets described herein eliciting a less robust immune response than cells or Neo-Islets that are not immune privileged. In various embodiments, the immune response to "immune privileged" cells or Neo-Islets may be 0, 5, 10, 20, 30, 40, 50, 60, 70, 80, 90, 95% or 100% or less than the immune response to non-immune privileged cells or Neo-Islets.

Differentiated islet cells express, e.g., insulin, but do not proliferate, or proliferate only minimally, in vitro. Isolated islet cells may be induced to dedifferentiate in vitro. As used herein, "dedifferentiated" islet cells or islet cell nuclei are cells or nuclei that no longer express or produce insulin when challenged with glucose. The process of dedifferentiation is also referred to herein as an Epithelial-Mesenchymal transition or an "E to M" transition. Dedifferentiated islet cells may proliferate in culture at a rate superior to differentiated islet cells. Dedifferentiation of the islet cells may immediately reduce or silence insulin expression, insulin synthesis, insulin storage, and/or glucose-induced insulin secretion in these cells. Isolated islet cells may be from any suitable host (e.g., rodent, canine, human, or other mammal).

Dedifferentiated islet cells may be allowed to proliferate in vitro to form a large pool of cells that may be co-cultured with other cell types.

Proliferation associated dedifferentiation may be achieved by culturing islet cells in conditions which are adherent for the islet cells. In various embodiments, the islet cells may be cultured on a surface that has been coated with or not coated with laminin 511 or laminin 411. Dedifferentiation may optionally be performed in a dedifferentiation medium. Dedifferentiation medium may include a glucagon-like peptide 1 (GLP-1) receptor agonist. In specific embodiments, the GLP-1 receptor agonist may be GLP-1, exenatide, liraglutide, lixisenatide, albiglutide, taspoglutide, and/or Exendin-4. The GLP-1 receptor agonist may be present in the dedifferentiation culture medium at a concentration from 0.1 to 100 nM, from 1 to 50 nM, or at 1, 2, 3, 4, 5, 6, 7, 8, 9, 10, 11, 12, 13, 14, 15, 16, 17, 18, 19, 20, 25, 26, 27, 28, 29, or 30 nM.

Culturing of isolated islets and/or islet cells on laminins (e.g., Laminin 411 and 511), and addition of suitable media, may improve cell adhesion in culture, support cell survival, and moderately boost proliferation. For dedifferentiation, islet cells may be plated on a suitable substrate that allows for attachment. In specific embodiments, the substrate may include Laminin 411 and/or Laminin 511. In a more specific embodiment, β-cells may be plated on tissue culture flasks or wells coated with Laminin-411 and/or Laminin-511 and placed in RPMI, DMEM, alpha MEM, CMRL, PIM, or other suitable culture medium and supplemented with 10% to 20% fetal bovine serum or other species specific serum or platelet lysate, and glutamine/penicillin/streptomycin. The culture medium may also be supplemented with at least 10 nM Exendin-4.

Examples of sera in which the Neo-Islets may be cultured include, but are not limited to, sera available from world-wideweb.sigmaaldrich.com. Specific non-limiting examples include: Fetal Bovine Serum, Bovine Calf Serum, Adult Bovine Serum, Chicken Serum, Goat Serum, Porcine Serum, Rabbit Serum, Sheep Serum, Horse Serum, Canine Serum, Baboon Serum, Coyote Serum, Goose Serum, Mouse Serum, Rat Serum, Rhesus Monkey Serum, Serum Replacement, and Human Serum.

MSCs and ASCs are undifferentiated, adult stem cells that proliferate well, and do not produce insulin.

Dedifferentiated islet cells proliferate well, but do not, or only minimally express or secrete insulin. In some embodiments, dedifferentiated islet cells are allowed to proliferate to generate sufficient numbers for subsequent manipulation. In certain embodiments, once sufficient dedifferentiated islet cells have been generated the cells are treated with an islet cell or beta cell-specific redifferentiation medium. Redifferentiation of the islet cells restores insulin production, resulting in the re-expression of physiological insulin expression, synthesis, storage, and glucose-sensitive insulin release.

Described is the redifferentiation of dedifferentiated islet cells to generate a redifferentiated islet cell. Redifferentiation, as used herein, refers to the treatment of dedifferentiated islet cells to generate a redifferentiated islet cell having restored expression of physiological insulin expression, synthesis, storage, and glucose-sensitive insulin release. In certain embodiments, redifferentiation may be a two-step process.

In a first step, a dedifferentiated islet cell may be exposed to a culture medium containing a low level of glucose. The low level of glucose may be selected from 1, 2, 3, 4, 5, 5.1, 5.2, 5.3, 5.4, 5.5, 5.6, 5.7, 5.8, 5.9, and 6 mM D-glucose. The medium may contain other components such as Insulin/Transferrin/Selenium (ITS), penicillin/streptomycin (Pen/Strep), fetal bovine serum (FBS), dog serum, or human platelet lysate. The first step may include culturing the dedifferentiated islet cell in the culture medium containing a low level of glucose for 1, 2, 3, 4, 5, 6, 7, 8, 9, 10, 11, 12, 13, 14, 1 to 14, 2 to 13, 3 to 12, 4 to 10, or 5 to 9 days.

In a second step, the dedifferentiated islet cell may be exposed to a culture medium containing a high level of glucose. The high level of glucose may be selected from 15, 16, 17, 18, 19, 20, 22, 23, 24, 25, 26, 27, 28, 29, 30, 31, 32, 33, 34, and 35 mM D-glucose. The medium may contain other components such as insulin/transferrin/selenium (ITS), penicillin/streptomycin (Pen/Strep), fetal bovine serum (FBS), dog serum, or human platelet lysate, N2 supplement, B27 supplement, nicotinamide, Activin A, Alk-5 inhibitor II, triiodothyronine, and a glucagon-like peptide 1 (GLP-1) receptor agonist. Nicotinamide may be present in the culture medium at a concentration from 0.1 to 100 mM, from 1 to 50 mM, or at 1, 2, 3, 4, 5, 6, 7, 8, 9, 10, 11, 12, 13, 14, 15, 16, 17, 18, 19, 20, 25, 26, 27, 28, 29, or 30 mM. Activin A may be present in the culture medium at a concentration from 0.1 to 100 mM, from 1 to 50 mM, or at 1, 2, 3, 4, 5, 6, 7, 8, 9, 10, 11, 12, 13, 14, 15, 16, 17, 18, 19, 20, 25, 26, 27, 28, 29, or 30 mM. The GLP-1 receptor agonist may be present in the culture medium at a concentration from 0.1 to 100 nM, from 1 to 50 nM, or at 1, 2, 3, 4, 5, 6, 7, 8, 9, 10, 11, 12, 13, 14, 15, 16, 17, 18, 19, 20, 25, 26, 27, 28, 29, or 30 nM. The Alk-5 inhibitor II may be present in the culture medium at a concentration from 1, 2, 3, 4, 5, 6, 7, 8, 9, 10, 11, 12, 13, 14, 15, 16, 17, 18, 19, 20, 25, 26, 27, 28, 29, or 30 μM. The triiodothyronine may be present in the culture medium at a concentration from 0.1 to 100 μM. The GLP-1 receptor agonist may be Exendin-4. The second step may include culturing the dedifferentiated islet cell in the culture medium containing a high level of glucose for 10, 12, 13, 14, 15, 16, 17, 18, 19, 20, 21, 22, 23, 24, 25, 26, 27, 28, 10 to 28, 11 to 27, 12 to 26, 13 to 25, or 14 to 29 days.

In some embodiments, a method is provided for generating insulin-producing cells through a substantial expansion in the amount of starting material (dedifferentiated islet cells) for subsequent culturing with proliferating MSCs or ASCs.

Methods are disclosed for the formation of the Neo-Islets as described herein. Such Neo-Islets may be approximately the size of islets found in the pancreas. Neo-Islets may be formed, e.g., by any method known in the art. In a non-limiting example, Neo-Islets are formed by the culturing of cells on hydrophobic, ultra-low adhesion surfaces.

Examples of hydrophobic and/or ultra-low adhesion surfaces include, but are not limited to untreated polystyrene, low attachment hydrogel layers, and uncharged surfaces.

Also described are methods of treating a subject in need of insulin and/or suffering from Type 1 ("T1DM") or Type 2 Diabetes Mellitus ("T2DM"), or suffering from impaired glucose tolerance or Prediabetes Mellitus, using the described Neo-Islets is disclosed. In some embodiments, Neo-Islets are administered intraperitoneally (i.p.) and/or to the omentum of the subject. In certain embodiments, Neo-Islets are administered s.c., i.v., or otherwise parenterally to the subject. In certain embodiments, administration of the Neo-Islets to the subject increases and/or restores insulin production, secretion, and glucose-responsiveness. In certain embodiments, the Neo-Islets may be coated with hydrogel or other FDA approved material prior to administration to further enhance survival of the Neo-Islets in vivo, such as gelfoam, or a thrombin clot. In embodiments where the Neo-Islets contain dedifferentiated islet cells, these cells may undergo redifferentiation in the subject after treatment of the subject with the Neo-Islets.

Methods of treating subjects with Neo-Islets comprise providing a sufficient dose of the Neo-Islets to a subject suffering from T1DM, T2DM, or impaired glucose tolerance to increase and/or restore insulin production, secretion, and glucose-responsiveness. This dose would be understood by those of ordinary skill in the art to vary depending on the route of administration, the degree of pathology in the subject to be treated, and the subject's response to therapy, see, e.g., Example 5 below discussing the doses of Neo-Islets administered i.p. in animal models. In certain embodiments, subsequent doses of Neo-Islets could be administered to the subject depending on their initial response to therapy.

The high efficiency (i.e. the very small loss of viable cells) of the methods described herein also provides a significant increase in the number of doses that can be obtained from a single pancreas over currently conventional treatment. For example, based on the average number of islets that can be obtained from a canine pancreas, expanding the islet cells to a first passage results, on average, the ability to generate 774 doses of neo-islets for a 10 kg canine. If the islet cells are expanded to a second passage results, on average, the ability to generate 1,550 therapeutic doses of neo-islets for a 10 kg canine. If these numbers are used as the basis for human treatment, it is estimated that 1,000 to 2,000 doses of neo-islets for a 70 kg human can be obtained per human pancreas. In contrast, current human islet transplants require approximately 4 pancreata for a single human dose. Further, repeat doses are often needed to achieve insulin independence.

"Treating" or "treatment" does not require a complete cure. It means that the symptoms of the underlying disease are at least reduced, and/or that one or more of the underlying cellular, physiological, or biochemical causes or mechanisms causing the symptoms are reduced and/or eliminated. Insulin requirements may be reduced. End organ damage may be reduced. The need for anti-rejection drugs may be reduced or eliminated. It is understood that reduced, as used in this context, means relative to the state of the disease, including the molecular state of the disease, not just the physiological state of the disease.

The treatment (especially in the early stages) may be aided by the administration of insulin and/or oral hypoglycemic agents (or drugs). Such drugs include the biguanides (e.g., metformin), sulfonylureas (e.g., glimepiride, glyburide, or glipizide), meglitinides (e.g., repaglinide), diphenylalanine derivatives (e.g., nateglinide), thiazolidinediones (e.g., pioglitazone), DPP-4 inhibitors (e.g., sitagliptin, saxagliptin, linagliptin), alpha-glucosidase inhibitors (e.g., acarbose or miglitol), bile acid sequestrants (e.g., colesevelam), etc. Dosages and administration of such drugs, adjuvants and/or intermediate treatment(s) would be readily determined by a person of ordinary skill in the art and dependent on the subject being treated, and need not be repeated here.

Also described are methods of preparation and packaging the Neo-Islets known in the art to allow for preparation of the Neo-Islets remotely from the subject to be treated while ensuring survival of the Neo-Islets before administration, further enhancing survival of the Neo-Islets in vivo after administration. For instance, various implants are well known to those of ordinary skill in the art. Encapsulation and microencapsulation devices and methods are also well known.

Packaging may be accomplished, for example, by means known in the art, such as packaging fresh or frozen Neo-Islets into, e.g., syringes, sterile bags, infusion bags, bottles, etc., for delivery to a subject or health care practitioner. Plasmalyte A pH 7.4 may be extremely useful in packaging the Neo-Islets.

The use of animal models, including rodent and canine models, is well understood by those of ordinary skill in the art to provide a useful tool in developing treatments for human diabetes (Aileen J. F. King, "The use of animal models in diabetes research," *Br. J. Pharmacol.*, 2012 Jun; 166(3):877-894). Indeed, as King notes, it is ideal to provide more than one animal model to better represent the diversity of human diabetes, as is disclosed herein. The description provided would enable those of ordinary skill in the art to make and use Neo-Islets to treat T1DM, T2DM, and impaired glucose tolerance in humans without any undue experimentation.

In some embodiments, the subject may be a mammal, such as, for example, a rodent, canine, feline, equine, or human. In further embodiments, cells in the Neo-Islet may be allogenic, xenogenic, or a combination of allogenic and xenogenic cells in relation to the subject or other cells in the Neo-Islet.

As used herein, "comprising," "including," "containing," "characterized by," and grammatical equivalents thereof are inclusive or open-ended terms that do not exclude additional, unrecited elements or method steps, but also include the more restrictive terms "consisting of" and "consisting essentially of"

EXAMPLES

The following examples are provided for illustration purposes only and are not to be construed as limiting the disclosure to the embodiments specifically disclosed therein.

Since Pancreatic islets, like all tissues, possess small numbers of Mesenchymal Stem Cells, as pericytes, that exert immune-modulating, anti-inflammatory and other protective trophic effects locally,[3-9] we hypothesized and tested whether Neo-Islets (NIs) comprising endocrine islet cells with much higher numbers of MSCs/ASCs could be formed, and whether such Neo-Islets would provide effective: (i) Autoimmune-Isolation without encapsulation devices, (ii) Survival benefits of allogeneic Neo-Islets in vivo, thereby reducing or eliminating the need for anti-rejection drugs, (iii) Redifferentiation in vivo of islet cells, and thereby (iv) Adequate and physiologic insulin secretion and durable maintenance of euglycemia in rodents with T1DM.

The unique and well documented pleiotropic and largely comparable actions of bone marrow-derived Mesenchymal Stromal Cells (MSCs) or adipose tissue-derived Adipose Stem Cells (ASCs), if combined with equal numbers of islet cells in islet-sized cell clusters or "Neo-Islets" (NI), are harnessed to shield administered β-cells from allo- and auto-immune attacks and inflammatory damage, and to enhance β-cell survival and induce angiogenesis. Physiologically, only about 2% of the total cell numbers in islets are thought to represent MSCs, located as pericyte-like cells in microvascular niches. Their cytoprotective functions within the islets likely parallel those in the bone marrow and other organs, i.e., vasculo-protection and stabilization, anti-inflammatory, trophic and immune-modulating activities. Such NIs of approximate islet size were generated in vitro from culture expanded, via Epithelial-Mesenchymal Transition (EMT) and associated dedifferentiation, islet cells and bone marrow-derived MSCs of C57Bl/6 mice. $5\times10^3$ NIs, each composed of ~500 islet cells and ~500 MSCs, were intraperitoneally (i.p.) administered to spontaneously diabetic, immune-competent NOD mice that develop an autoimmune form of T1DM that largely resembles human T1DM. This allogeneic treatment protocol was chosen as it models the most common clinical situation in recipients of pancreas or islet transplants. By not using anti-rejection drugs or encapsulation devices, we rigorously tested that high numbers of MSCs in NIs do enable islet cells to survive, redifferentiate into normally functioning endocrine cells, and thereby durably establish glycemic control in NOD mice with autoimmune T1DM. While NI treated diabetic NOD mice thrived normally, vehicle treated, diabetic NOD mice remained hyperglycemic and began to die. These initial data implied that NIs survive, engraft, and redifferentiate into functional endocrine cells in vivo, and that both allo- and auto-immune protection is achieved. Importantly, following i.p. administration the NIs were taken up by the omentum where they engrafted long term and redifferentiated into physiologically insulin-producing cells. NOD mice did not mount a humoral allo-immune response to the MSCs and islet cells that are used to form NIs. NI-treated diabetic animals showed a significant increase in regulatory T cell (Treg) numbers in their omenta and spleens compared to animals that were treated with islets. When NIs were injected into nondiabetic animals, they also engrafted and survived in the omentum without causing hypoglycemia, further demonstrating regulated insulin secretion. Insulin secretion from the omentum occurs into the portal system of the liver, as does that from the pancreas, which is physiologic and results in inactivation of ~50% of the delivered insulin. This limits the post-hepatic exposure of muscle, adipose tissue, the vasculature and other organs to supraphysiological, potentially hypoglycemia-inducing and otherwise harmful insulin levels that are generated when insulin is subcutaneously given. When streptozotocin (STZ) diabetic mice were treated with similarly sized cell clusters composed of either only MSCs or Islet cells, blood glucose levels, compared to NI treated, euglycemic animals, were only minimally lowered compared to vehicle treated controls. This clearly demonstrated that the therapeutic efficacy of NIs depends critically on the collaboration of MCSs and islet cells. Finally, when STZ-diabetic NOD/SCID mice were treated i.p. by identical protocol with canine NIs (cNI), euglycemia was readily and durably induced and intraperitoneal Glucose Tolerance Tests (IP GTT) were normalized. Importantly, the insulin that was released during the IP GTT was canine specific, and when cNIs were surgically removed, hyperglycemia redeveloped. Taken together, the present data demonstrate that the complex pleiotropic actions of MSCs or ASCs (M/ASCs), as hypothesized, can be readily harnessed to protect cultured islet cells, and when combined with them in NIs and administered i.p., facilitate long term glycemic control in mice with autoimmune T1DM. We conclude, therefore, that these observations have significant translational relevance for the treatment of T1DM.

Reagents: Reagents used and their sources are listed in the following table.

| Reagent | Source |
|---|---|
| 20 mM citrate buffer pH 4.5 | Sigma, St. Louis, MO |
| 4',6-diamidino-2-phenylindole dihydrochloride | Life Technologies, Carlsbad, CA |
| Accumax | Innovative Cell Technologies, Inc., San Diego, CA |
| ACK buffer | Life Technologies, Carlsbad, CA |
| Anti-Ki67 rabbit IgG monoclonal antibody (ab16667) | Abcam, Cambridge, MA |
| Bovine Serum Albumin (BSA) | Sigma, St. Louis, MO |
| Canine IFN-gamma (781-CG-050) | R&D Systems, Minneapolis, MN |
| Canine Insulin ELISA kit | Mercodia, Uppsala, Sweden |
| Canine serum | Golden West Biologicals, Temecula, CA |
| Click-iT EdU Alexa Fluor 594 Imaging Kit | Invitrogen, Carlsbad, CA |
| Cell Tracker Green | Life Technologies, Carlsbad, CA |
| Collagenase 1 | Worthington, Lakewood, NJ |
| Collagenase P | Roche, Indianapolis, IN |
| Cy3 conjugated goat anti-rabbit IgG (111116003) | Jackson ImmunoResearch, West Grove, PA |
| Cy3-conjugated goat-anti-mouse IgG ab | Jackson ImmunoResearch, West Grove, PA |
| DAB substrate Staining (SK-4100) | Vector Laboratories, Burlingame, CA |
| DiI | Life Technologies, Carlsbad, CA |
| DiR | Life Technologies, Carlsbad, CA |
| dithizone | Sigma, St. Louis, MO |
| DMEM-F12 | Sigma, St. Louis, MO |
| DMSO | Sigma, St. Louis, MO |
| donkey anti-guinea pig cy5 conjugated antibody | Jackson ImmunoResearch, West Grove, PA |
| Eosin Y Solution | Sigma, St. Louis, MO |
| Fetal Bovine Serum (FBS) | Hyclone, Logan, UT |
| Fluorescein diacetate | Sigma, St. Louis, MO |
| Formalin | Sigma, St. Louis, MO |
| Gelfoam | Pfizer, Kalamazoo, MI |
| Gentamycin Penicillin Streptomycin (GPS) | Sigma, St. Louis, MO |
| guinea pig anti-insulin antibody | Dako, Carpinteria, CA |
| Hanks Buffered Saline Solution | Gibco, Carlsbad, CA |
| Hematoxylin counterstain (H-3404) | Vector Laboratories, Burlingame, CA |
| HEPES | Gibco, Carlsbad, CA |
| Histopaque 1077 | Sigma, St. Louis, MO |
| Histopaque-1.119 | Sigma, St. Louis, MO |
| Isoflurane | Baxter, Deerfield, IL |
| Laminin-511 | BioLamina, Uppsala, Sweden |
| L-Glutamine-Penicillin-Streptomycin (GPS) | Sigma, St. Louis, MO |
| Linbits | LinShin Canada, Toronto, Ontario, Canada |
| Mouse T Lymphocyte Subset Antibody Cocktail (#558391) | BD Pharmingen, San Jose, CA |
| $NaHCO_3$ | Sigma, St. Louis, MO |
| OneTouch Ultra2 Glucometer | Johnson and Johnson, New Brunswick, NJ |
| PBS | Roche, Indianapolis, IN |
| Propidium Iodide | Life Technologies, Carlsbad, CA |
| Qiagen RNeasy Mini Kit | Qiagen, Germantown, MD |
| rabbit anti Foxp3 antibody (ab54501) | Abcam, Cambridge, MA |
| RPMI 1640 | Life Technologies, Carlsbad, CA |
| Stempro Osteo-, Chondro-, Adiogenic differentiation kits | Gibco, Carlsbad, CA |
| Streptozotocin | Sigma, St. Louis, MO |
| Superscript II Reverse Transcriptase | Invitrogen, Carlsbad, CA |

-continued

| Reagent | Source |
|---|---|
| TaqMan PCR primers | Applied Biosystems, Foster City, CA |
| TaqMan Universal Master Mix II with UNG | Applied Biosystems, Foster City, CA |
| Tregs Detection Kit (#130-094-165) | Miltenyi Biotec, Bergisch Gladbach, Germany |
| Triton X 100 | Fisher Scientific, Waltham, MA |
| Trypsin EDTA | Sigma, St. Louis, MO |

Example 1: Islet Isolation

From Rodents: Mice were euthanized with Isoflurane (3-5%) in a sealed chamber, and immediately placed on a surgical board for a sterile midline incision. The pancreas was exposed, the pancreatic duct located. The common bile duct was clamped, and the pancreas was inflated with 5 ml/mouse or 15 ml/rat 1 mg/ml Collagenase P in Dissociation Buffer (Hanks Buffered Saline Solution (HBSS), $Ca^{++}$, $Mg^{++}$+25 mM HEPES+$NaHCO_3$) via the common bile duct. The inflated pancreas was removed to a sterile conical tube containing digestion solution (1 mg/ml Collagenase P in Dissociation Buffer.). The tube was placed in a 37° C. shaking water bath (120 rpm) and the contents digested for 15 minutes. The digestion was stopped with an equal volume of cold Dissociation Buffer. The digested tissue was filtered through a 400 μm screen into a fresh tube, and centrifuged at 1200 rpm for 2 minutes at 4° C. with the brake off. The pellet was washed with 20 ml Dissociation Buffer and centrifuged again (1200 rpm for 2 minutes at 4° C. with the brake off). To purify the islets further, the pellet was resuspended in 10 ml Histopaque 1077 solution and overlayed with 10 ml serum free DMEM-F12 to set up a gradient. The gradient was centrifuged at 2000 rpm for 20 minutes at 4° C. with the brake off, and the islets were collected at the interface between the medium and Histopaque into a 50 ml conical tube containing 20 ml Dissociation Buffer. The islets were then centrifuged at 1200 rpm for 2 minutes, washed with 20 ml Dissociation Buffer, spun down again, resuspended in islet culture medium, and placed in a sterile Petri dish. Islets were allowed to recover in a 37° C., 5% $CO_2$ humidified incubator at pH 7.4 overnight.

From Dogs: Fresh pancreata were obtained from euthanized dogs through an NIH sharing agreement and inflated via the common bile duct, using 1 mg/ml Collagenase P solution. Canine islets were isolated from inflated pancreases following modified versions of techniques described by Vrabelova, et al. and Woolcott, et al.[10, 11] In brief, the distended dog pancreas was cut in 15 to 20 pieces and placed in a 50 ml tube containing 20 ml of 1 mg/ml Collagenase P solution. The tube was placed into a 37° C. water bath with the shaker set at 120 rpm. Islet content in the solution was monitored by microscopic examination of dithizone stained samples obtained from small samples taken at 5-minute intervals. Digestion was continued until approximately 50% of islets were free of acinar tissue, and stopped with 20 ml of HBSS supplemented with 10 mM HEPES+1% BSA. The tissue was then gently sieved through a 400-μm screen and centrifuged for 10 seconds at 100× g at 4° C. The pellets were washed once and centrifuged for 10 seconds at 200× g (4° C.). Three layer density gradients were created by resuspending the pellets in 10 ml Histopaque-1.119, slowly layering on top 10 ml of Histopaque-1.077 followed by another layer of 10 ml of serum-free medium. The gradient was spun at 750×g for 20 minutes at 4° C. without brake. Islets were collected from the top interface and transferred to a 50 ml tube containing HBSS supplemented with 10 mM HEPES+1% BSA. The purified islet suspensions were washed with serum-free medium and centrifuged for 10 seconds at 200× g (4° C.) twice and passed through a 40-μl cell strainer. Five 50 μl aliquots from each preparation were collected and used to assess the islet yield. Finally, handpicked (to remove acinar cell content) islets were cultured in 20% FBS supplemented RPMI 1640 medium at 37° C., in a 5% $CO_2$ incubator.

From Humans: Human islets were purchased from Prodo Laboratories (Irvine, CA).

Example 2: Culture and De-Differentiation of Islet Cells

Rodent Islet Cells: Recovered mouse islets were handpicked and further purified by capturing the islets in the top of a 40 μm filter strainer. Islets were cultured as follows: islet cells were cultured by placing whole islets on Laminin-511 coated wells, and allowing the islet cells to outgrow from the islets until 90% confluent in RPMI 1640+20% FBS+GPS, which results in their dedifferentiation via reversible EMT. Culturing in this manner further purifies islet cells and removes remaining exocrine cells. Passaging: Mouse islet cells were allowed to grow to approximately 90% confluence. They were then trypsinized (1× Trypsin-EDTA for 5-10 minutes), pelleted by centrifugation at 600×g for 5 minutes, washed with DMEMF12+20% FBS+GPS, and seeded into T75 flasks. Passaged islet cells were cultured in DMEM-F12+20% FBS+GPS. Culturing in this manner further purifies islet cells and removes acinar and ductal cells.

Canine Islet Cells: Initial Culture: Recovered dog islets were handpicked and further purified by capturing the islets in the top of a 40-μm filter strainer. Cells were cultured as whole islets as described above for mice. Passaging: see as above for rodent islet cells.

Human Islet Cells: Cells were cultured as whole islets and passaged as described above for rodents.

Example 3: Isolation and Culture of ASCs and MSCs

ASCs (mouse and canine): Under sterile conditions, approximately 3-15 g abdominal fat samples were harvested from euthanized, non-diabetic mice or non-diabetic dogs (NIH tissue sharing agreement) and placed on ice in separate, sterile 50 ml conical tubes containing approximately 30 ml of 1× PBS. The fat samples were minced, placed in tubes of PBS containing 3 mg/ml Collagenase 1, and digested approximately 1 hour in a 37° C. shaking water bath. The tubes were centrifuged (600× g, 10 minutes) to pellet the cellular content. The supernatant was carefully removed, and the pellet washed two times with sterile PBS, and then resuspended in 10 ml DMEM F12+GPS+10% FBS for culture. Cells were cultured in a 37° C. humidified 5% $CO_2$ incubator at pH 7.4. Culture medium was changed twice weekly. When primary cultures reached 70-80% confluence, attached cells were passaged by exposure to 1×trypsin/EDTA for 3-5 minutes, and and further passaged or cryopreserved in 10% DMSO.

Non-diabetic Human ASCs were purchased at P1 from Lonza (Walkersville, MD), and cultured as described above.

MSCs (from rodents): Obtained cell suspensions from flushed femurs of euthanized mice were plated in T25 flasks containing DMEM-F12+10% FBS+ GPS. Cells were cultured in a 37° C. humidified 5% $CO_2$ incubator. Culture medium was changed twice weekly. When primary cultures reached 70-80% confluence, cells were detached with 1× trypsin/EDTA for 3-5 minutes, and passaged or frozen in 10% DMSO.

Prior to Neo-Islet formation, cultured MSCs or ASCs are characterized (i) by FACS for their expression of CD44 and CD90, and negative expression of CD45, CD34 and DLA-DR antigens, and (ii) by their abilities to undergo trilineage differentiation (adipogenic, osteogenic, chondrogenic) as previously described.[15] Prior to Neo-Islet formation, cultured, dedifferentiated canine islet cells are examined by (a) FACS and confirmed to be negative for expression of DLA-DR, CD90 and CD133; and (b) rtPCR for residual islet cell gene expression of insulin, glucagon, somatostatin, pdx-1, and nkx6.1. Cell viability was assessed using Fluorescein diacetate (FDA) and Propidium Iodide (PI) as follows: 1× staining solution (1 μL of 5 mg/ml FDA and 5 μL of 1 mg/ml PI dissolved in 100 μL PBS) was mixed with cells in 100 μL PBS, incubated at room temperature for 30 seconds and cells were imaged using a fluorescence microscope. Four fields were counted for red, green and total cell numbers.

Example 4: Induction of Indoleamine 2, 3 Dioxygenase (IDO-1)

Canine ASCs were tested at P2 for induction of IDO-1 in response to canine interferon gamma (IFNγ) as follows. Eight 35 mm culture dishes were seeded with $0.5\times10^6$ canine-derived ASCs each in DMEM F12+10% canine serum. 10 ng/ml canine INFγ was added to four dishes. After overnight culture in a 37° C. humidified 5% $CO_2$ incubator, cells from all dishes were harvested and assayed for IDO-1 gene expression by rtPCR. Results from IFNγ treated cultures were normalized to those of unexposed cells of the same passage number and expressed as Log10RQ.

Example 5: Neo-Islet Formation and In Vitro Characterization

Rationale: (A) To test whether Neo-Islets comprising (i) dedifferentiated, culture expanded islet cells combined with (ii) much higher numbers of MSCs/ASCs than occurs naturally in islets could be formed. (B) To determine whether and to what extent such Neo-Islets express or can be induced to express islet cell associated genes.

Methods

Outgrowth of islet cells: Islet cells were either (1) dissociated with trypsin and cells plated in Laminin-511 and/or Laminin-411 (20 μg/ml) pre-coated Tissue Culture (TC) wells or flasks, or (2) whole islets were plated in Laminin-511 and/or Laminin-411 coated TC wells. See FIG. 1. In both cases, cells were cultured and allowed to propagate in RPMI or other suitable growth medium supplemented with 20% Fetal Bovine Serum (FBS)+glutamine/penicillin/streptomycin (GPS)+Exendin 4 (Glp-1 at 10 nM for rodent cell cultures) until sub-confluence (all supplements are commercially available). This process takes approximately one to two weeks. Islet cells became dedifferentiated within a matter of days, judging from immunohistochemistry (IHC) for insulin presence, Insulin Enzyme Linked Immunosorbent Assay (ELISA), Glucose Stimulated Insulin Release assays (GSIS), gene expression profiles (rtPCR), and from murine cell lines transgenic for Green Fluorescent Protein (gfp) under the control of the insulin 1 gene promoter.[1] See FIGS. 2 and 8A-8C.

Neo-Islet formation: ASCs (P1 to P4) or MSCs (P1 to P5) and Islet cells (P1 to P2) were co-cultured at a 1:1 ratio in ultra-low attachment surface culture dishes (Corning, Kennebunk, ME) and allowed to form NIs overnight. Control ASC and Islet cell clusters were formed by the same method. Prior to their in vivo administration, samples of NIs were tested by rtPCR for expression of islet and MSC associated genes (see below).

Staining for confocal microscopy: ASCs or MSCs were stained with Cell Tracker Green (green), and passaged islet cells were stained with Lipophilic Tracer DiI (red) by following the manufacturers' instructions. Post cell staining, NIs were formed, collected, fixed in 10% formalin and stained with 4',6-diamidino-2-phenylindole dihydrochloride (DAPI) prior to confocal microscopy.

Lipophilic Tracer DiR labeling of Neo-Islets was carried out following the manufacturer's instructions.

Redifferentiation of Neo-Islets: Re-differentiation of Neo-Islets was achieved in vitro using commercially available additives, in a two-step process. Step 1: Neo-Islets of rodent, canine or human origin were cultured for 6-8 days in serum free DMEM containing 5.6 mM D-glucose and supplemented with: (a) 1% BSA fraction V, (b) ITS-G, (c) GPS. Step 2: After 6-8 days, this medium was replaced with Redifferentiation Medium (RDM) and cultured 2 weeks. RDM is DMEM containing 25 mM glucose and supplemented with: (a) N2 supplement A (commercially available), (b) SM-1 supplement (commercially available), (c) 10 mM Nicotinamide (commercially available), (d) 10 nM exendin 4 (commercially available), (e) 2 nM Activin A (commercially available). Redifferentiation tested and confirmed by rtPCR for expression of islet and MSC associated genes as described below.

Neo-Islet cellular ratio assessment: For each species (mouse, dog, human), adherent cultures of ASCs and dog, mouse ICs were harvested as described above. ASCs were stained green with cell tracker green in order to be able to distinguish them from ICs. Staining efficiency was assessed by FACS and determined to be ≥95%. ICs were left unstained. NIs were formed overnight in six-well ultra-low adhesion plates as described above using $0.5\times10^6$ ASCs and $0.5\times10^6$ ICs per well in 2 ml DMEM/F12+10% FBS. The next day, NIs were collected and dissociated to single cell preparations by 30 minutes incubation with 1 ml Accumax per well. Single cell preparations were then resuspended in 1× PBS+1% BSA and analyzed by FACS (BD FACScan Analyzer, San Jose, California) for percent green (ASC) vs. unstained (IC) cells.

rtPCR: RNA was extracted from $1\times10^6$ cell samples using a Qiagen RNeasy Mini Kit, including a DNase digestion step to exclude contaminating DNA, and following the manufacturer's instructions. Reverse transcription was performed using SuperScript II Reverse Transcriptase for 60 minutes at 42° C. Real-time PCR was carried out in duplicate using species-specific TaqMan primers (Applied Biosystems, ABS, Foster City, California) and following the manufacturer's instructions. All reactions were carried out in a total volume of 20 μL with TaqMan Universal Master Mix II with UNG. Reaction conditions were 50° C. for 2 minutes, followed by a 95° C. for 10 minutes start, and 40 cycles of melting at 95° C. for 15 seconds and annealing at 60° C. for 1 minute. All samples were run in duplicate, and the average threshold cycle (Ct) value was used for calculations. The ABS 7500 Real Time PCR System was used to monitor real-time PCR. Relative quantitation (RQ, normalization) of each target gene was calculated with the Ct method using the ABS software provided with the instrument, and by normalization to two internal housekeeping genes, beta actin and beta 2 microglobulin (B2m). RQ was calculated through normalization to external controls as indicated, and by using the software provided with the machine. Results are presented as log 10 (RQ)±log 10 (RQmin and RQmax). Differences greater than log 10 (RQ) 2 or less than log 10 (RQ) −2 were considered significant. Utilized PCR primers are listed in the following table.

| Target genes (MOUSE) | ABS catalog # |
|---|---|
| Actb | Mm04394036_g1 |
| B2m | Mm00437762_m1 |
| Ins1 | Mm01259683_g1 |
| Ins2 | Mm00731595_gH |
| Gcg | Mm01269055_m1 |
| Sst | Mm00436671_m1 |
| Ppy | Mm01250509_g1 |
| Pdx1 | Mm00435565_m1 |
| Mafa | Mm00845206_s1 |
| Slc2a1 | Mm00441480_m1 |
| Slc2a2 | Mm00446229_m1 |
| Ucn3 | Mm00453206_s1 |
| Abcc8 | Mm00803450_m1 |
| Nkx6-1 | Mm00454961_m1 |
| Glp1r | Mm00445292_m1 |
| Kcnj11 | Mm00440050_s1 |
| Vegfa | Mm01281449_m1 |
| Cxcl12 | Mm00445553_m1 |
| Tgfb1 | Mm01178820_m1 |
| Igf1 | Mm00439560_m1 |

| Target genes (DOG) | ABS catalog # |
|---|---|
| ACTB | Cf03023880_g1 |
| B2M | Cf02659077_m1 |
| INS | Cf02647520_m1 |
| GCG | Cf02624195_m1 |
| SST | Cf02625293_m1 |
| PDX1 | Cf02622671_m1 |
| NKX6-1 | Cf02705682_mH |
| ABCC8 | Cf02690717_m1 |
| GLP1R | Cf02696492_m1 |
| VEGFA | Cf02623449_m1 |
| CXCL12 | Cf02625258_m1 |
| TGFB1 | Cf02623325_m1 |
| IGF1 | Cf02627846_m1 |
| IDO-1 | Cf02640742_m1 |

| Target genes (HUMAN) | ABS catalog # |
|---|---|
| ACTB | Hs01060665_g1 |
| B2M | Hs00984230_m1 |
| INS | Hs02741908_m1 |
| GCG | Hs01031536_m1 |
| SST | Hs00356144_m1 |
| PPY | Hs00358111_g1 |
| PDX1 | Hs00236830_m1 |
| MAFA | Hs01651425_s1 |
| NKX6-1 | Hs00232355_m1 |
| UCN3 | Hs00846499_s1 |

-continued

| Target genes (HUMAN) | ABS catalog # |
|---|---|
| ABCC8 | Hs01093761_m1 |
| VEGFA | Hs00900055_m1 |
| CXCL12 | Hs03676656_mH |
| TGFB1 | Hs00998133_m1 |
| IGF1 | Hs01547656_m1 |

Results

Figure 3:
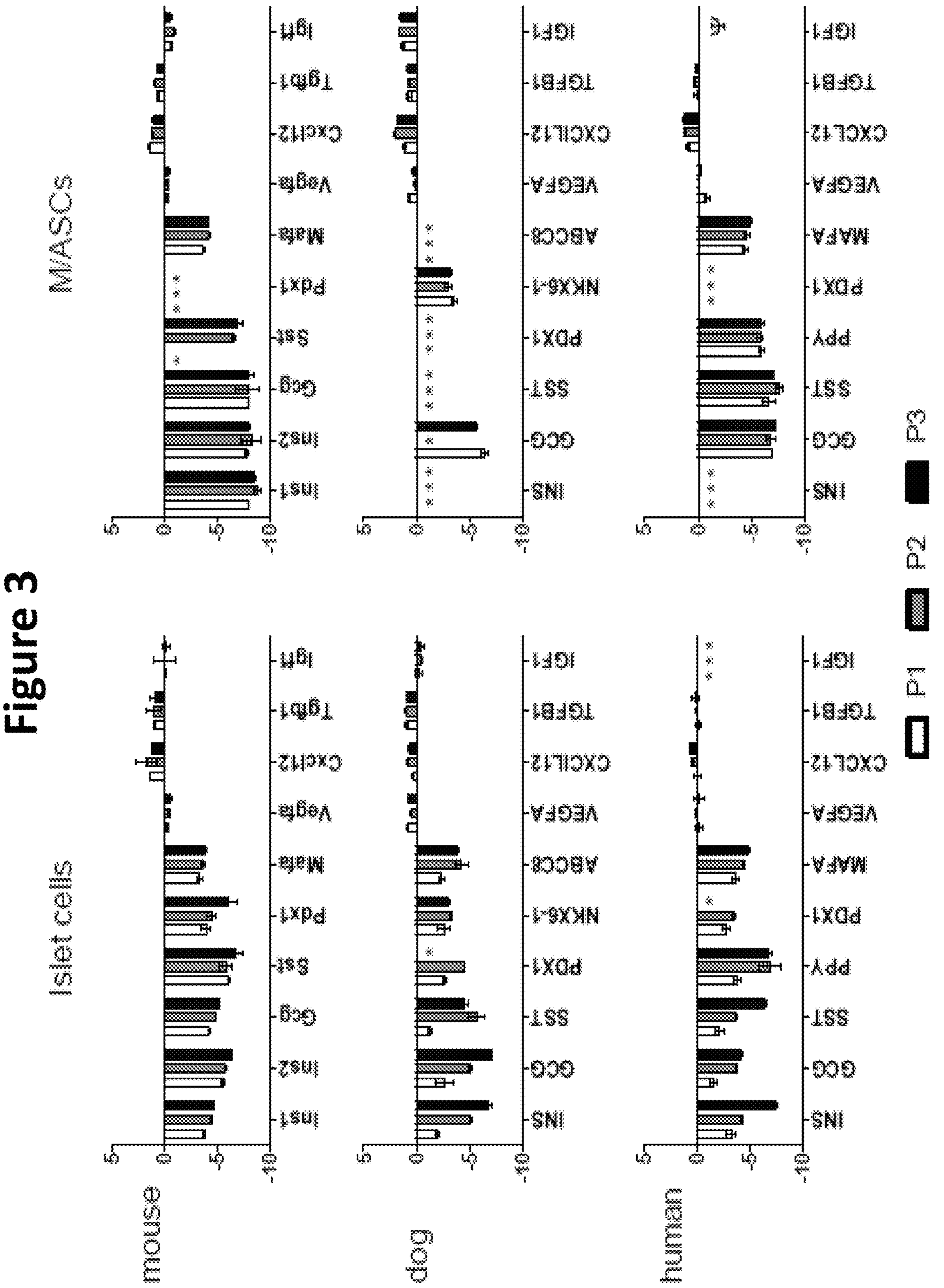
FIG. 3: Comparative, passage (P) dependent gene expression profiles of NI starting materials. Gene expression profiles (Log10RQ) of mouse, dog and human cultured islet cells (left) and M/ASCs (right) at passages 1, 2 and 3 (P1, P2, and P3, respectively). All gene expression profiles for both cell types were normalized to those of species-specific, freshly isolated islets. Overall, in mice, dogs and humans, gene expression profiles of ASCs differ from those of passaged islet cells, and passaging of islet cells progressively decreases the expression of islet cell associated genes. Data: mean with 95% CI, representative of six independent experiments. ψ, expressed in hASCs, but not in human islet cells, preventing respective normalization; *, not expressed.

Growth and Characterization of ICs and M/ASCs: The NIs' starting materials, i.e., cultured ICs and M/ASCs, were obtained as follows. Freshly isolated islets from non-diabetic mice, dogs and humans were tested for viability, placed in culture, and grown and passaged as described in the above examples. ICs grow out of the islets, proliferate and dedifferentiate as they undergo EMT, a reversible process. Cultured ICs retain residual IC-associated gene expression profiles that decrease with passaging, and exhibit a gene expression pattern distinct from those of M/ASCs (FIG. 3). All ICs were used at P1-P2 for NI formation and experimentation. MSCs and ASCs were obtained from non-diabetic mice, dogs and humans and cultured and characterized as described in Example 3. All MSCs and ASCs met the minimal criteria of plastic adherence, ability to undergo trilineage differentiation, expression of characteristic cell surface epitopes, and importantly, absent expression of I-A[b] (mouse)/DLA-DR (dog)/HLA-DR (human) transplant antigens. Exposure of canine ASCs to IFNγ significantly induced indoleamine 2, 3 dioxygenase (IDO-1) gene expression (FIGS. 4A-4D), an important inhibitor of the T cell response in inflammatory states such as insulitis. M/ASCs were used at P1-P5 for NI formation and experimentation. Both ICs and M/ASCs were karyotyped (Veterinary Medicine and Biomedical Sciences, Texas A&M University, College Station, TX) and found to be normal.

Neo-Islet formation and imaging: FIG. 1 shows a schematic of Neo-Islet formation and a proposed use. As shown in the figure, dedifferentiated islet cells and ASCs or MSCs were used to form Neo-Islets that can be induced to produce islet cell specific proteins to treat T1DM or T2DM; dedifferentiated islet cells and ASCs or MSCs. The islet cells were first outgrown from the islet (mouse, canine or human), and allowed to dedifferentiate and proliferate for one or more passages. Once dedifferentiated, such cells express and produce significantly reduced to no islet cell specific genes or proteins, respectively. ASCs or MSCs were cultured by standard methods up to 4 passages. Once sufficient numbers of each cell type are available, the two cell types can be co-cultured in low-adhesion flasks to form islet-sized Neo-Islets.

Figure 2:
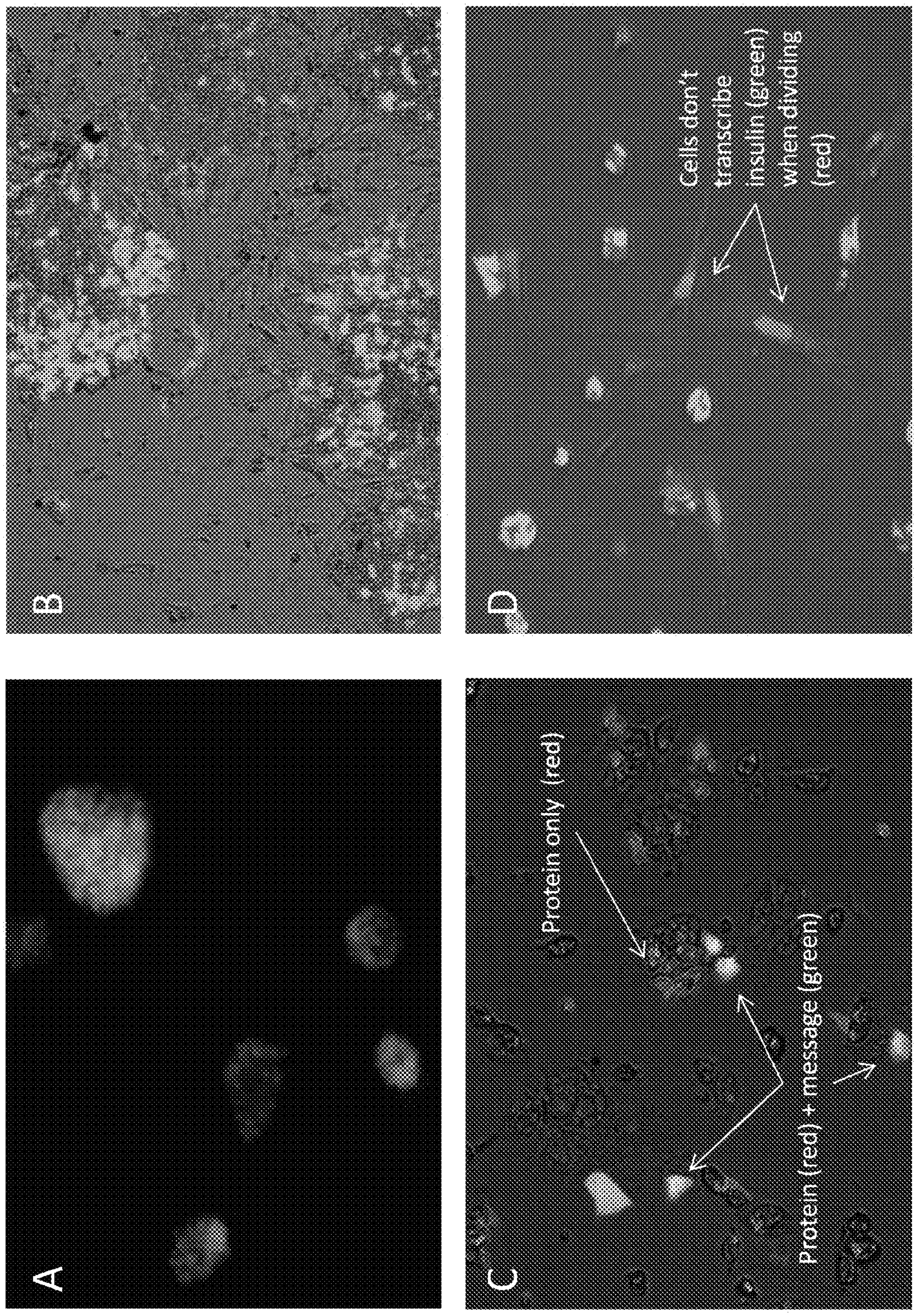
FIG. 2: Outgrowth and Epithelial to Mesenchymal transition of cultured islet cells. All images are at 10× magnification. Panel A: Whole islets freshly isolated from the transgenic C57Bl/6 ins 1gfp mouse, wherein the Green Fluorescent Protein gene (gfp) is under the control of the Insulin 1 (ins1) gene promoter.[1] Islet beta cells are green. Panel B: Ins 1gfp+ whole islets after 6 days of culture. Significant insulin gene expression is still apparent (green cells), but cells are outgrowing from the islets and proliferating. In these outgrown cells, insulin gene expression is downregulated and the cells are no longer green. Panel C: Dissociated ins 1gfp+ mouse Islet cells cultured for 1 day, and fixed and analyzed by immunocytochemistry for insulin protein, using a guinea-pig anti-insulin antibody, and a $cy^3$-conjugated anti-guinea pig antibody to visualize insulin protein (red). The image reveals that while there are very few gfp+ cells, approximately half the cells contain insulin, yet are not green. This indicates that the beta cells attach and proliferate as they lose the expression of the insulin gene due to Epithelial Mesenchymal transition. Panel D: Dissociated Ins 1gfp+ islet cells cultured 2 days in the presence of EdU. Cells were fixed and stained with Hoechst33342 (nuclei, blue) and for EdU (red). Cells that are not dividing are bright green and have a round, epithelial morphology, while cells that are dividing (red nuclei) are taking on an elongated, mesenchymal appearance, and are only faintly green, indicating the down-regulation of insulin gene expression, and illustrating their Epithelial Mesenchymal transition.

FIG. 2 illustrates the outgrowth and Epithelial to Mesenchymal transition that resulted from culturing islet cells in the manner described herein. To help illustrate this phenomenon, the transgenic, C57Bl/6, ins 1gfp+ mouse, wherein the green fluorescent protein (gfp) is under the control of the Insulin 1 (ins') gene promoter, was used.[1] As only islet beta cells express the Insulin 1 gene, insulin-gene-expressing beta cells isolated from this strain appear green, and are thus readily identifiable. Panel A shows whole islets isolated from the ins1-gfp+ mouse. These islets were cultured on Laminin-511 coated plates as described above. Panel B of FIG. 2 is of Ins 1gfp+ whole islets after 6 days of culture. While there was still significant insulin gene expression where islets attached (green cells), cells are detaching from the islets and proliferating, and in these cells, insulin gene expression is downregulated (cells are no longer green). This is more fully illustrated in Panel C of FIG. 2, which depicts Ins 1gfp+ islet cells that were trypsinized to dissociate the islets prior to culture, then fixed and stained for Insulin protein (red). Where cells are green or yellow the ins1 gene is still actively transcribed and translated. Where cells appear red only, insulin protein is present, but lack of green (or yellow) color indicates the gene is down-regulated. Finally, Panel D of FIG. 2 shows Ins 1gfp+ islet cells that were grown in the presence of EdU to track cell division. These cells were fixed and stained with Hoechst (nuclei, blue) and for EdU (red). Cells in which ins 1 gene translation is occurring appear green. Nuclei of cells that are dividing appear red. As can be seen in the image, cells that are not dividing are bright green and have a round, epithelial morphology, while cells that are dividing (red nuclei) are taking on an elongated, mesenchymal appearance, and are only faintly green, indicating the down-regulation of insulin gene expression.

Figure 5:
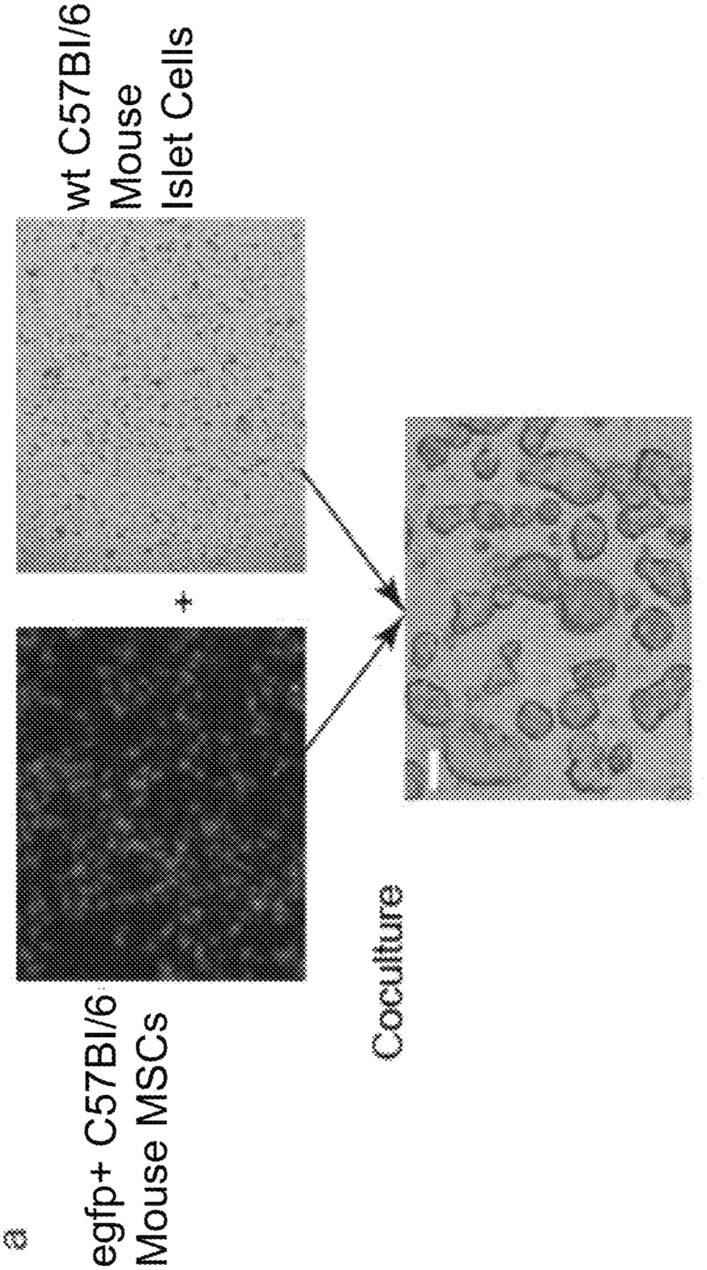
FIG. 5: Neo-Islet formation and imaging.
Figure 6:
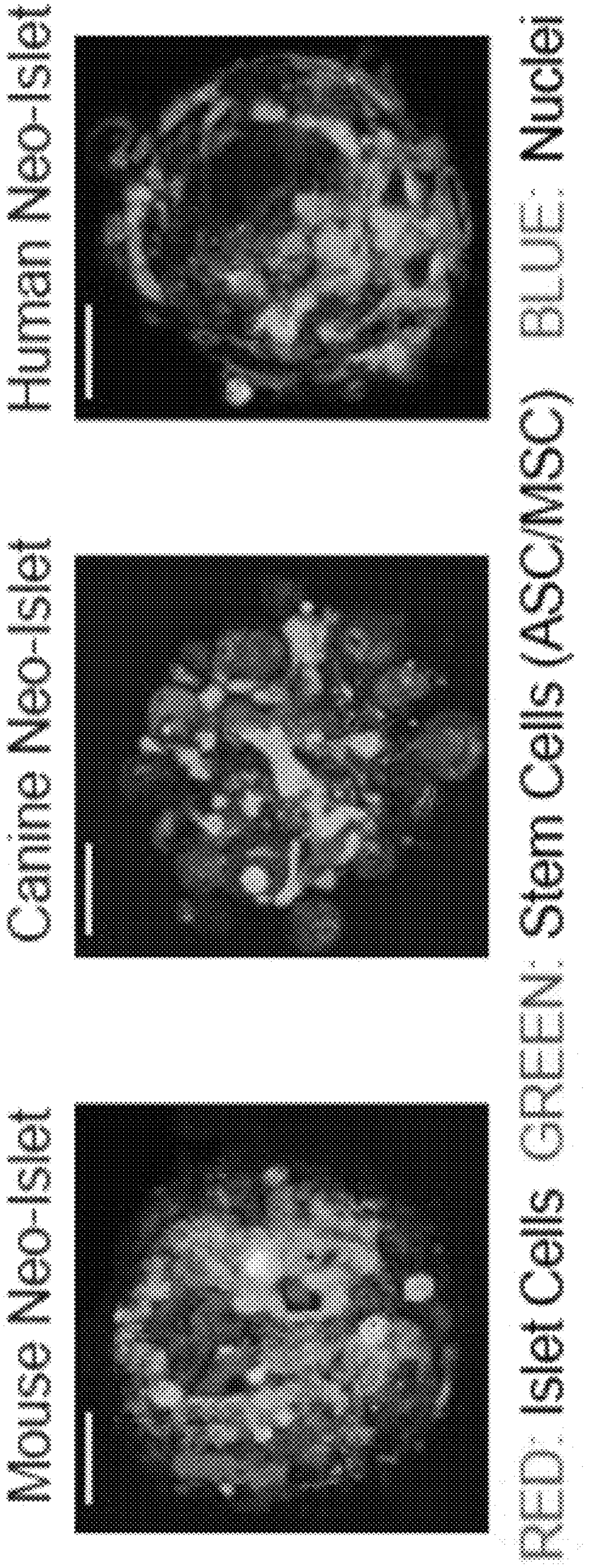
FIG. 6: LEFT, MIDDLE and RIGHT PANELS: images (63× magnifications) of Murine (left), Canine (middle) and Human (right) Neo-IsletNeo-Islets; ASCs (green), islet cells (red) and nuclei (blue). Morphology and cell composition do not differ significantly among murine, canine and human Neo-IsletNeo-Islets.

NIs of approximate islet size of 150 μm were prepared by overnight co-culturing of bone marrow-derived MSCs or their adipose-derived analogs ASCs (M/ASCs) with culture expanded murine islet cells (ICs) at a 1:1 ratio (found to be optimal) in an ultralow cell adhesion system. An example of this process using mouse cells is shown in FIG. 5. To further assess the potential translational relevance of such murine NIs, we confirmed that comparable NIs could be readily generated from both canine and human ICs and M/ASCs. Green fluorescent protein positive (gfp+) C57Bl/6 mouse MSCs and C57Bl/6 mouse islet cells were grown. The two cell types were then cultured in low-adhesion plates and formed Neo-Islets. Confocal images (63× magnification) of single Murine, Canine and Human Neo-Islets of ASCs (green) and islet cells (red) are shown respectively in the left, middle and right images of FIG. 6. As can be seen, for Neo-Islets of either murine, canine or human origin, endocrine and stem cells are distributed equally throughout the Neo-Islet. The percent of each cell type in NIs was further assessed as follows. Canine ASCs were stained with Cell Tracker Green and cocultured with unstained islet cells at a 1:1 ratio as above. After NIs were formed, they were dissociated with Accumax to single cells and analyzed by FACS as described in Online Methods, which revealed that at 24 hours post-formation, NIs are comprised of approximately 50% M/ASCs and 50% ICs (FIG. 7A), further indicating both cell types remain in a 1:1 ratio within NIs post-formation.

Figure 8A:
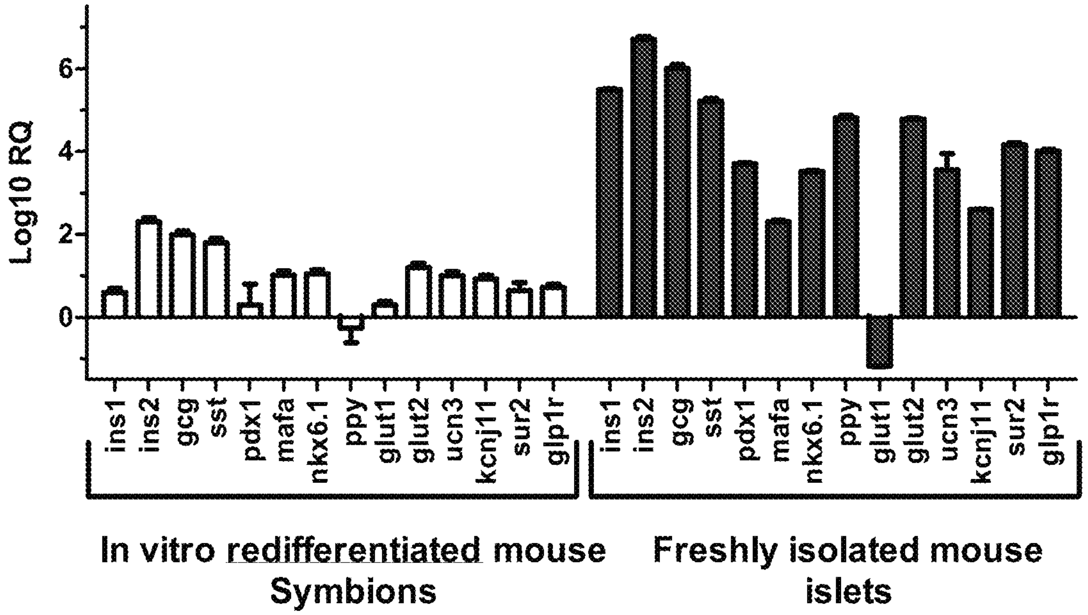
FIGS. 8A-8C: Gene Expression Profiles of Mouse, Dog, and Human Neo-Islets. All data are normalized to 2 housekeeping genes, β-actin and (32 microglobulin.
Figure 8A:
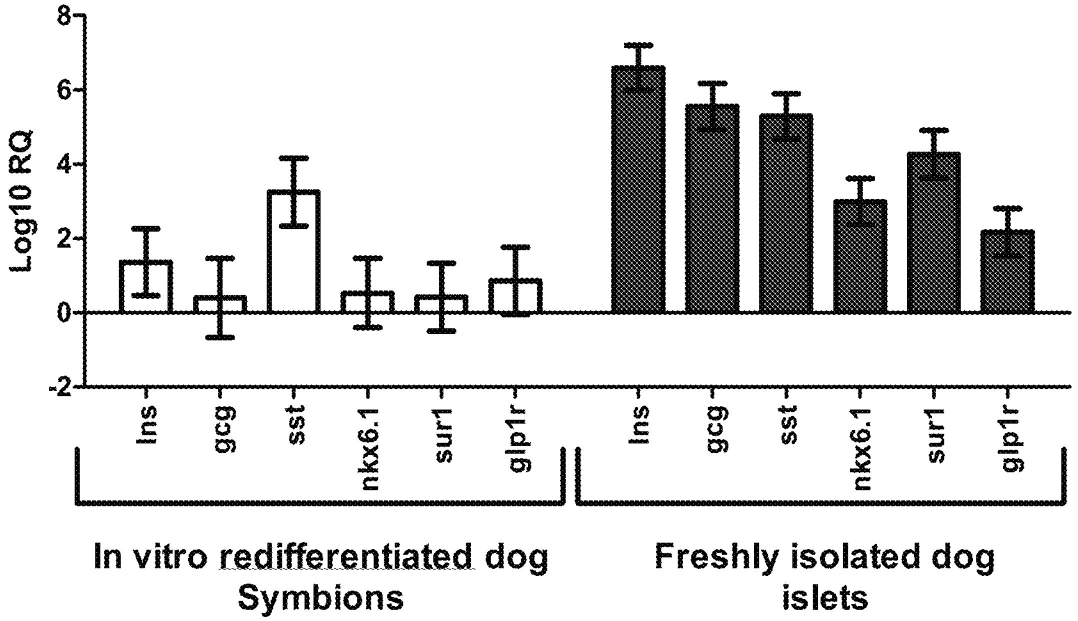
Figure 8B:
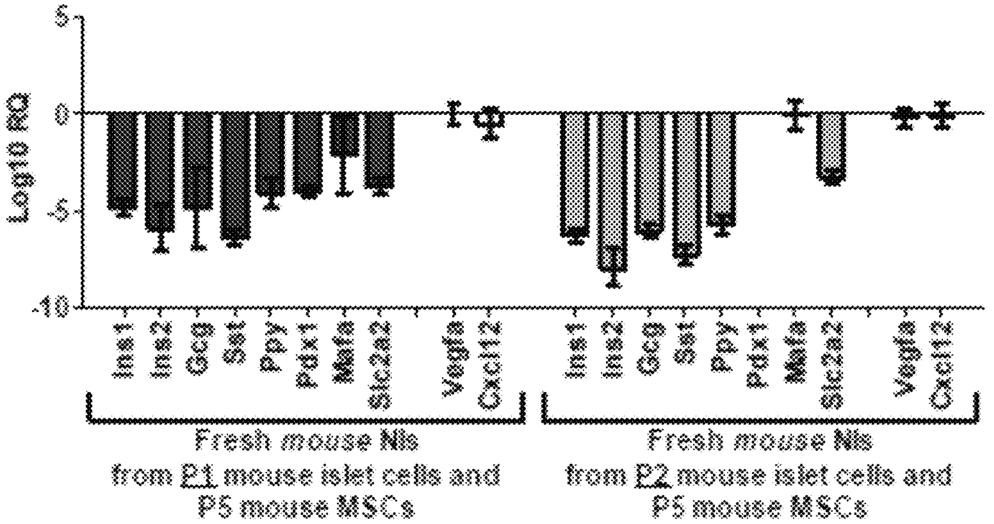
Figure 8B:
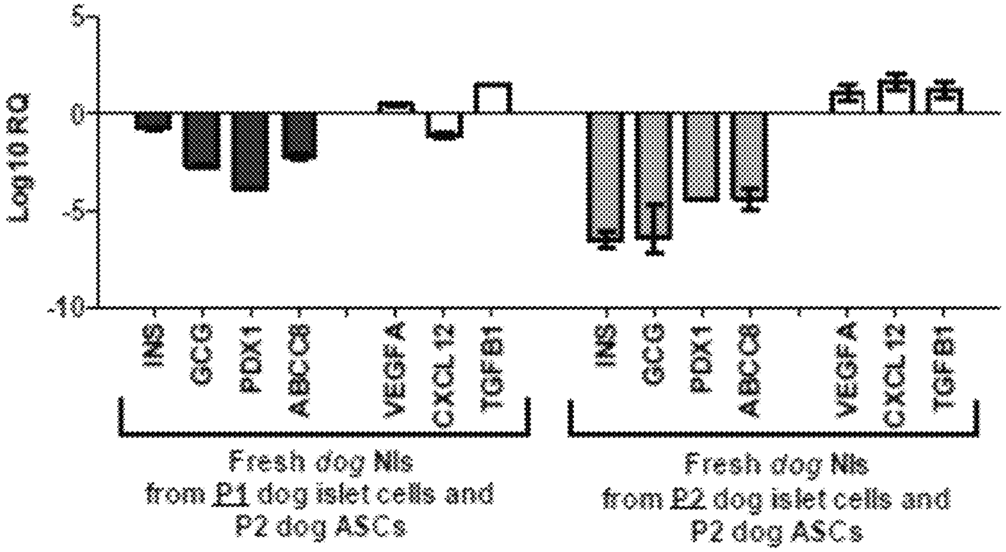
Figure 8B:
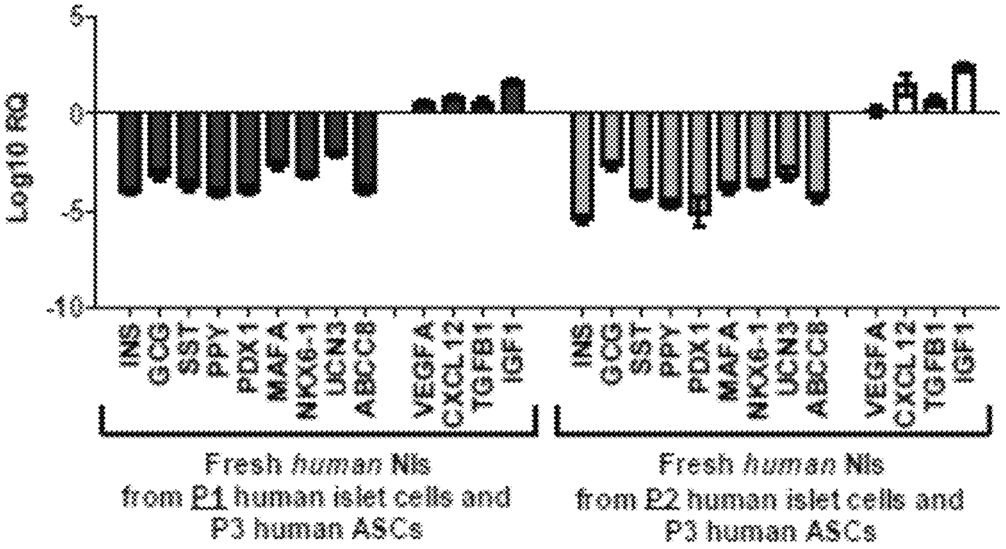
Figure 8C:
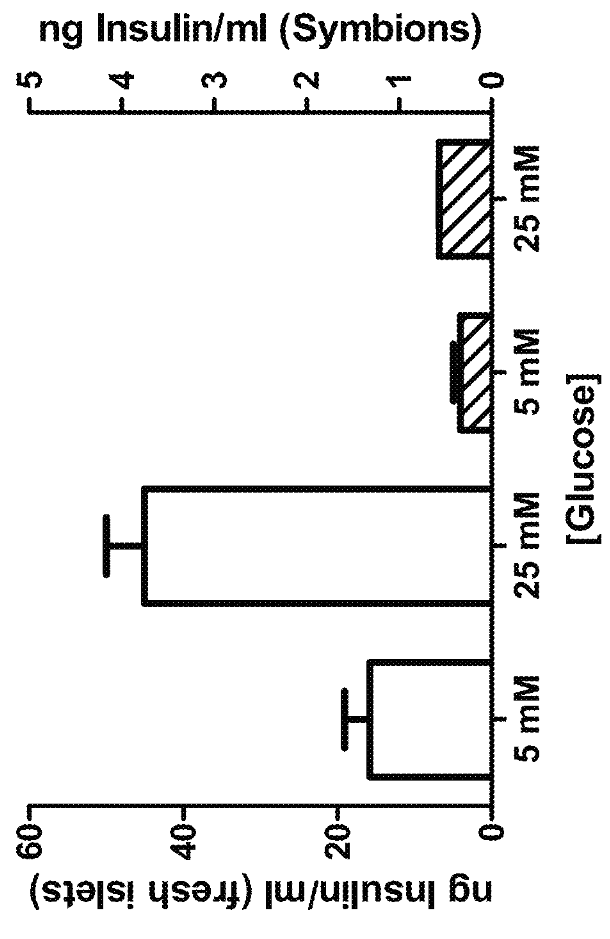

Gene expression profiles and Glucose Stimulated Insulin Secretion of murine, canine and human Neo-Islets: While these Neo-Islets do not express significant levels of insulin, as cultured islet cells undergo an Epithelial to Mesenchymal transition when cultured, they may be redifferentiated in vitro using the redifferentiation protocol outlined above, such that they re-express islet cell genes. When the two cell types, ICs and M/ASCs, were combined to form NIs as shown in FIG. 5, the NI gene expression pattern exhibited characteristics of both cell types. FIG. 8A shows the islet gene expression profiles of mouse (top) and dog (bottom) Neo-Islets 14 days post exposure to redifferentiation medium (left sides) compared with those of freshly isolated mouse or dog islets (right sides). Both sets of gene expression profiles were normalized to those of freshly formed, dedifferentiated mouse (top) or dog (bottom) Neo-Islets. These results indicate that the freshly formed mouse and dog Neo-Islets express low levels of all tested islet associated genes, and have the capacity to undergo redifferentiation to express higher levels of these genes. Freshly formed NIs were able to secrete insulin in response to glucose in vitro, albeit at approximately 100-fold less than intact islets FIG. 8B shows the gene expression profiles of freshly formed murine (top), canine (middle) and human (bottom) Neo-Islets made from MSCs or ASCs and either P1 (left) or P2 (right) islet cells as compared to freshly isolated islets from those species (normalization). As can be seen in this panel, freshly formed mouse, dog and human Neo-Islets all express low levels of islet associated genes, as well as genes associated with ASCs/MSCs (vegf-α, cxcl12, tgfβ1 and ifg1), and for each of these species, the expression of islet cell genes decreases with higher islet cell passage number. As shown in FIG. 8C, in response to exposure to 25 mM glucose, the Glucose Stimulated Insulin Secretion (GSIS) by 50 freshly formed C57Bl/6 mouse Neo-Islets (P1 islet cells and P5 MSCs, cross hatched bars) is approximately 1% that of 50 freshly isolated C57Bl/6 mouse islets (open bars). This parallels the decrease in insulin gene expression seen in FIG. 8B.

Conclusion: Taken together, these results indicate (i) that Neo-Islets of cultured islet cells and either MSCs or ASCs can be readily formed in vitro; (ii) that across species (mouse, dog, human), such Neo-Islets are similar in appearance and gene expression profiles, expressing low levels of islet associated genes; (iii) that across species (mouse, dog, human) such Neo-Islets are capable of being redifferentiated in vitro to re-express pancreatic endocrine associated genes. Furthermore, these results suggest that these Neo-Islets may be of therapeutic use in treating insulin dependent and non-insulin dependent diabetic humans or animals.

Example 6: In Vivo, Dose Finding and Proof of Principle Studies in Apontaneously Diabetic NOD Mice and STZ-Diabetic NOD/SCID Mice Treated I.P. with Rodent Neo-Islets

Animal Models

All studies involving animals were conducted in adherence to the NIH Guide for the Care and Use of Laboratory Animals, and were supervised and approved by an institutional veterinarian and member of the IACUC. Mice and rats were purchased from either Jackson Laboratory (Bar Harbor, ME) or Harlan (Haslett, MI), and were housed at constant temperature and humidity, with a 12:12-hour light-dark cycle in regular, shoebox type caging. Unless otherwise indicated, all mice and rats had unrestricted access to a standard diet and tap water. All mouse experiments were carried out using female C57Bl/6, female NOD or female NOD/SCID mice weighing between 15 and 35 g. All rat experiments were conducted on male Sprague-Dawley rats weighing between 538 and 650 g.

Polydextran Particle Omental Uptake protocol

Four, 2-year-old Sprague-Dawley rats weighing between 538-650 g were anesthetized and treated i.p. with 5 ml polydextran particles (PDP; sterile sephadex G-25, particle size 87-510 μm) suspended 1:1 in Normal Saline. On Day 7 post administration, animals were sacrificed, and their omenta and other organs were harvested and examined for the presence of PDP.

Diabetes Models

Streptozotocin (STZ): Non-Obese Diabetic/Severe Combined Immunodeficiency (NOD/SCID) and C57Bl/6 mice were made diabetic with 3-5 i.p. doses (1 dose per day) of 50-75 mg/kg b.w. STZ, freshly dissolved in 20 mM citrate buffer, pH 4.5. Mice were considered to be diabetic when their non-fasting blood glucose levels were >300 mg/dL on 3 separate days.

Spontaneous: Female NOD mice develop T1DM spontaneously between 12-20 weeks of age. Mice were considered to be diabetic when their non-fasting blood glucose levels were >300 mg/dL on 3 separate days. Insulin treatment: Where indicated in Results and the figures, insulin was administered to diabetic animals via slow-release, sub-cutaneous insulin pellets (Linbits). Animals were anesthetized with isoflurane, and 1-3 Linbit pellets were inserted just under the skin following the manufacturer's instructions. Tail vein blood glucose concentrations were monitored for several days to ensure animals were neither hyper-nor hypo-glycemic.

Blood Glucose Monitoring: In all animal studies, blood glucose concentrations were assessed twice per week via tail vein sampling, and using a OneTouch Ultra 2 glucometer (level of detection, 20-600 mg glucose/dL). Anesthesia: Animals were anesthetized with isoflurane, 1-5%, using an inhalation rodent anesthesia system (Euthanex, Palmer, PA). Rectal temperatures were maintained at 37° C. using a heated surgical waterbed (Euthanex, Palmer, PA).

Treatment of diabetic NOD mice with allogeneic NIs from C57Bl/6 mice: Diabetic NOD mice' blood glucose levels were normalized with Linbits, and NIs, composed of P5 eGFP+ MSCs and P1 islet cells ($2\times10^5$ NIs/kg b.wt. suspended in 0.5 ml serum-free DMEM-F12 medium; N=6) or vehicle (0.5 ml serum-free DMEM-F12 medium; N=6) were sterilely administered i.p., using light isofluorane anesthesia on Day 20 post-Linbit administration. No subsequent exogenous insulin was given in either group. At 10 weeks post NI administration, mice were euthanized, and their omenta, livers, spleens, lungs, kidneys and pancreases were harvested and examined by fluorescence microscopy for the presence of eGFP+ NIs. Sera were also collected to test for an allo-IgG response to the cells that make up the NIs. As a positive control for this test, an additional group of 3 NOD mice was given Linbits and treated i.p. with $2\times10^5$ freshly isolated, allogeneic islets/kg b.wt. suspended in 0.5 ml serum-free DMEM-F12. These mice were euthanized 14 days post-islet administration, and their sera harvested and examined as above.

STZ diabetic C57Bl/6 mouse treatment with syngeneic NIs, ASC-clusters or IC-clusters: Four groups of 10-week old, STZ-diabetic, blood glucose controlled (via Linbits) wt C57Bl/6 mice were administered i.p. (i) 0.5 ml vehicle (serum-free DMEM-F12; N=6), or $2\times10^5$/kg b.wt. (ii) freshly formed NIs (P5 eGFP+ MSCs and P1 ICs; N=6), (iii) clusters composed of P1 ASCs only (N=5), or (iv) clusters composed of P1 ICs only (N=5). Mice were followed as indicated. Upon euthanization, omenta, pancreata, spleens, livers, lungs and kidneys were harvested and fluoroscopically examined for the presence of eGFP+ NIs. In addition, islet associated gene expression profiles were obtained in all omenta and pancreata.

Treatment of non-diabetic mice with mouse or canine NIs: Mouse NIs: Six groups of 2 to 4, 12-week old C57Bl/6 mice each were administered i.p. either (i) $2\times10^5$/kg b.wt. freshly formed syngeneic NIs (P5 MSCs and P1 ICs) suspended in 0.5 ml serum-free DMEM-F12, or (ii) 0.5 ml serum-free DMEM-F12 (vehicle). Mice were followed for up to 12 weeks. Canine NIs: Two groups of 9-week old NOD/SCID mice were treated i.p. with (i) $2\times10^5$/kg b.wt. freshly formed cNIs suspended in 0.5 ml DMEM/F12 (N=6) or (ii) 0.5 ml serum-free DMEM-F12 (vehicle; N=3). Mice were followed for 10 weeks.

Results

To test our central hypothesis in a clinically highly informative autoimmune TIDM model, we first examined whether the i.p. administration of in vitro generated allogeneic NIs could reestablish euglycemia in spontaneously diabetic NOD mice as a reflection of (i) their survival, (ii) the redifferentiation of islet cells contained in the NIs into functional insulin-producing cells in vivo, and (iii) the MSC-mediated cyto-, allo- and auto-immune protection of the transplanted cell clusters.

Treatment of spontaneously diabetic NOD Mice with allogeneic NIs. Since others found that islet progenitor cells and dedifferentiated islet beta cells can differentiate into functional endocrine cells in vivo, we tested whether allogeneic murine NIs as described herein which were administered i.p. to spontaneously diabetic NOD mice, which develop a T-cell mediated, autoimmune form of T1DM, would reestablish euglycemia. This protocol was chosen because it closely resembles the most common clinical situation in which a patient with T1DM receives an allogeneic pancreas or islet transplant. To facilitate both in vivo tracking and post-mortem localization, administered NIs were dually labeled with DiR and composed of P5 MSCs derived from C57Bl/6 mice transgenic for the eGFP gene, constitutively expressed in all tissues, and P1 ICs from wild type C57Bl/6 mice (see FIG. 5). Others have demonstrated that normalization of blood glucose levels with insulin enhances the redifferentiation of islet cells into insulin producing cells in vivo which simultaneously reduces the glucotoxic effects on the transplanted cells. Thus, to avoid potential glucotoxic effects on the transplanted NIs, and to stimulate endocrine redifferentiation of transplanted ICs, blood glucose levels of twelve spontaneously diabetic, female NOD mice were normalized with the subcutaneous administration of insulin-releasing pellets (Linbits), an effect that lasts for 30-40 days post-administration.

Figure 9:
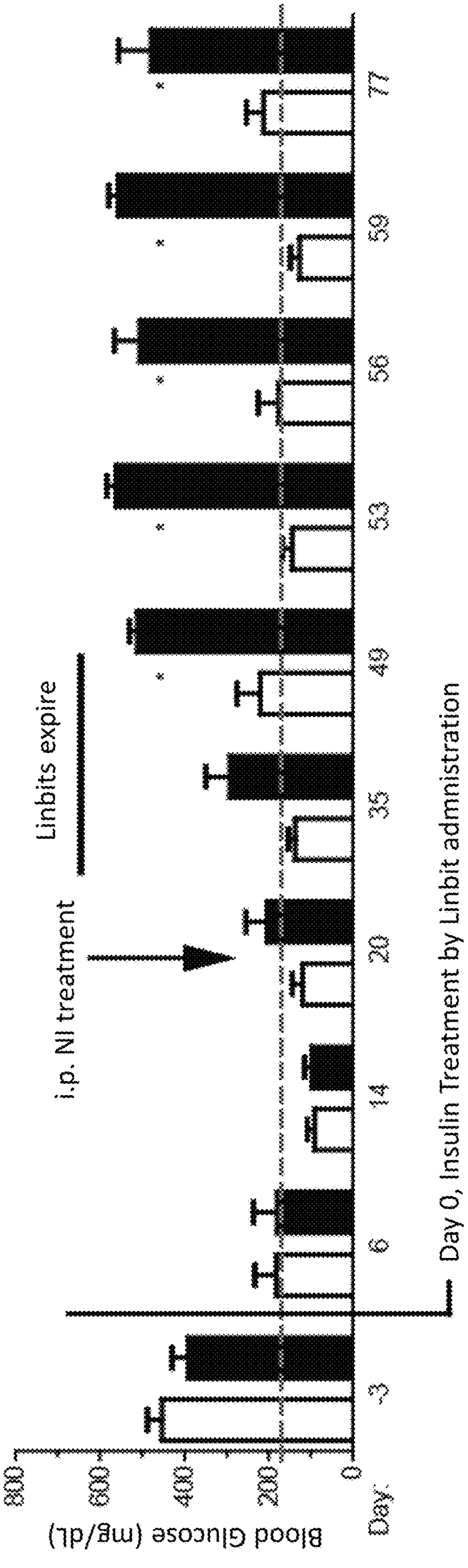
FIG. 9. Allogeneic NI-treatment established euglycemia in spontaneously diabetic NOD mice. Blood glucose levels (mean±SEM) of NOD mice normalized with Linbits (Day 0), then infused i.p. on Day 20 post Linbit therapy with $2\times10^5$ C57Bl/6 NI/kg (n=6; open bars) or vehicle (n=6; black bars). While vehicle treated mouse blood glucose levels increased when Linbits expired (approximately Day 35), euglycemia was maintained long term in NI treated mice, implying IC redifferentiation into insulin producing cells and NI-mediated immune protection from allo- and autoimmune attacks. Normal blood glucose level, hashed line. *, P<0.05 vs. vehicle treated group.
Figure 14A:
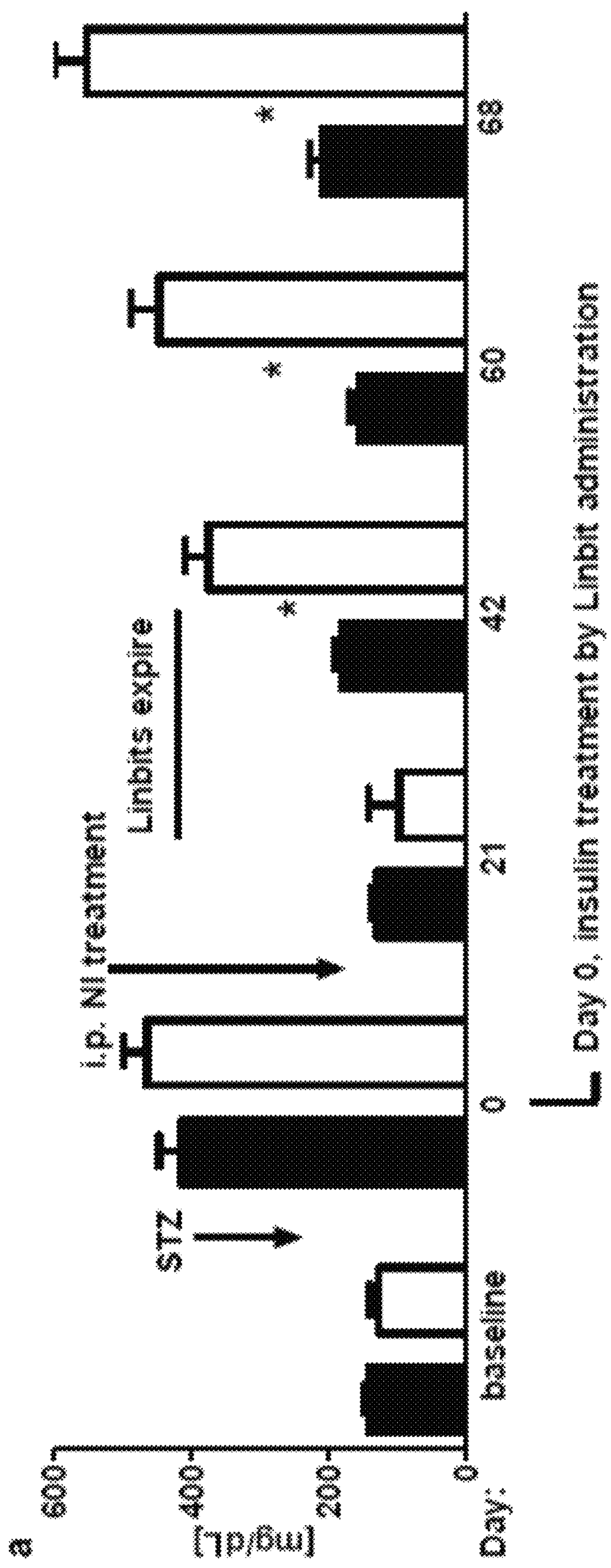
FIGS. 14A and 14B. I.P. administered syn- and xenogeneic NIs normalize blood glucose levels of STZ-diabetic mice.
Figure 14B:
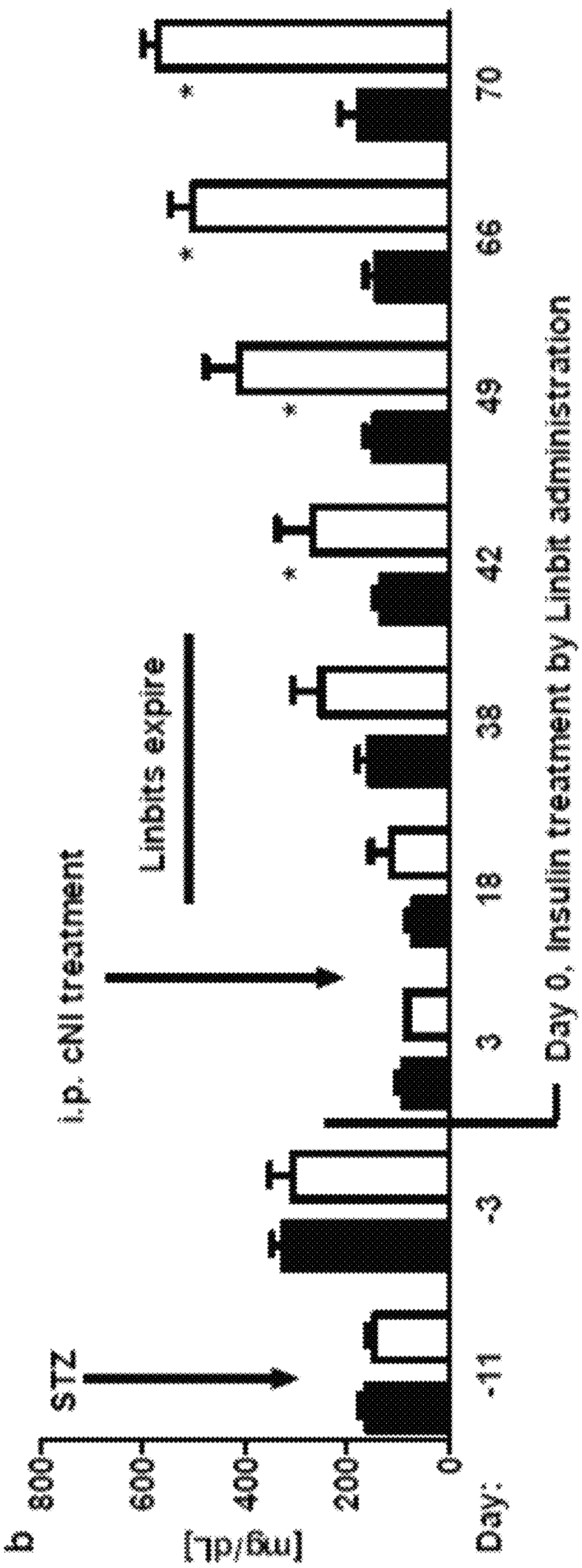

These mice were then divided into two groups and treated i.p. either with $2\times10^5$/kg b.wt. NIs from allogeneic C57Bl/6 mice (N=6) or with vehicle (N=6; FIG. 9). As expected, by day 35-40 post-Linbit treatment, hyperglycemia redeveloped in vehicle-treated NOD mice, while strikingly, blood glucose levels in NI-treated animals remained near normal (FIG. 9). Similar restoration of normoglycemia was achieved in parallel experiments for Streptozotocin (STZ) diabetic C57Bl/6 mice, treated with syngeneic, and STZ-diabetic NOD/SCID mice, treated with xenogeneic (canine) NIs (FIGS. 14A and 14B).

Together, these data show that (i) the NIs engraft and survive, (ii) the ICs within the NIs redifferentiate in vivo, providing the mouse with a new, endogenous source of insulin, and (iii) the MSCs contained in the NIs effectively provide cyto-protection and allo- and auto-immune-isolation of the insulin producing cells in NOD mice, and apparently establishing glycemic control in in this clinically highly relevant T1DM model.

Figure 11:
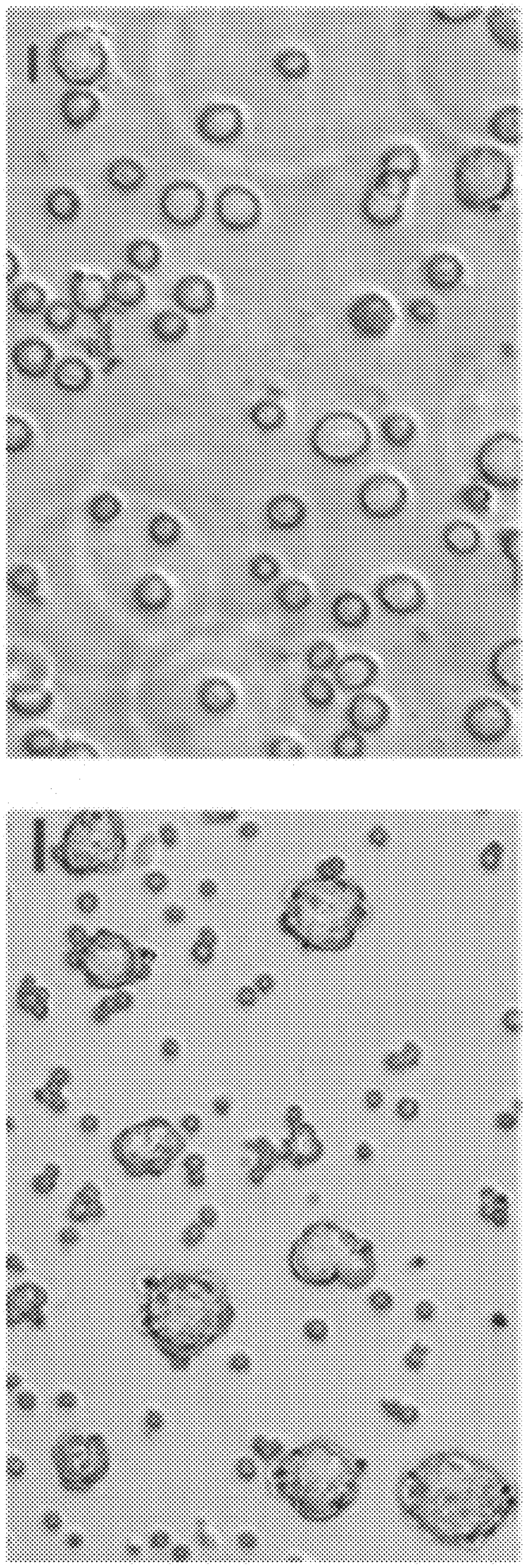
FIG. 11: Morphology and viability of C57Bl/6 IC— and ASCclusters used to treat mice in FIGS. 10A-10C. Fluorescence images of P1 IC-only (left) and P1 ASC-only (right) clusters post formation and stained for viability with PI (red) and FDA (green, see Methods). ASC-only and IC-only clusters are >95% viable prior to i.p. injection. Scale bar (red)=150 μm.

Collaboration of Islet Cells and M/ASCs within NIs is Essential to Establishing Normoglycemia in Diabetic Animals. To further explore the collaboration between ICs and M/ASCs in NIs, two experiments were conducted and are summarized in FIGS. 10A-10C. In these, a readily controllable Streptozotocin (STZ) model of T1DM in immune competent C57Bl/6 mice was used. In the first group, STZ-diabetic C57Bl/6 mice were treated i.p. with $2\times10^5$/kg b.wt. syngeneic NIs or with vehicle. In the second, STZ-diabetic C57Bl/6 mice were treated i.p. with $2\times10^5$/kg b.wt. control clusters composed of either ASCs (P1) or passaged ICs (P1) alone (FIG. 11). Importantly, the total number of cells in each generated cell cluster was identical to that in NIs (~1,000 cells per cluster). Three mice from the NI-treated group, and all mice from the control groups were euthanized at 12 weeks. The remaining three NI-treated mice were followed for 21 weeks. Long-term (21 weeks) euglycemia was obtained in STZ-diabetic C57Bl/6 mice that were treated i.p. with syngeneic NIs. Significantly, treatment with identically generated control clusters composed of either ASCs or cultured ICs alone only minimally reduced blood glucose levels when IC clusters were given (FIG. 10A), demonstrating that both ICs and stem cells must be present within NIs to facilitate optimal redifferentiation of insulin producing cells.

In vivo Redifferentiation. Data from the NOD mouse experiment (FIG. 9), as well as from retrieved omenta (FIG. 18B) imply that the NIs redifferentiate in vivo to produce sufficient insulin to render mice euglycemic. Indeed, omenta retrieved from the euglycemic, C57Bl/6 NI-treated mice at 21 weeks showed both engraftment of NIs and significantly increased insulin, glucagon, somatostatin and Pdx1 gene expression compared to the NIs they were treated with (FIG. 10B). This clearly demonstrates effective in vivo redifferentiation of islet hormone-expressing islet cells. Furthermore, expression of Ins1 and Ins2 in whole pancreata of STZ-diabetic mice was, as expected, significantly reduced in all animals (FIG. 10C), indicating that euglycemia in NI-treated mice was achieved by physiological insulin secretion provided by omentally engrafted NIs and not by residual pancreatic insulin.

Example 7: In Vivo, Dose Finding and Proof of Principle Studies in STZ-Diabetic NOD/SCID Mice Treated I.P. with Canine Neo-Islets Rationale: In Example 5, it was shown that freshly formed Neo-Islets of ASCs and dedifferentiated islet cells express low levels of islet associated genes as well as ASC/MSC associated genes. It was also observed that the endocrine derived component of such Neo-Islets have the capacity to redifferentiate in vitro to re-express higher levels of islet associated genes. Others have shown that endocrine precursor cells can redifferentiate in vivo to produce insulin. We therefore tested (i) whether Neo-Islets comprising canine ASCs and dedifferentiated islet cells can dose-dependently reverse hyperglycemia and affect animal survival, and (ii) whether removal of Neo-Islets would result in the return of hyperglycemia, confirming that Neo-Islets are exclusively responsible for the obtained treatment of T1DM.

Methods

Neo-Islets: Neo-Islets were formed from canine ASCs (passage 2) and canine cultured islet cells (passage 1).

Figure 12:
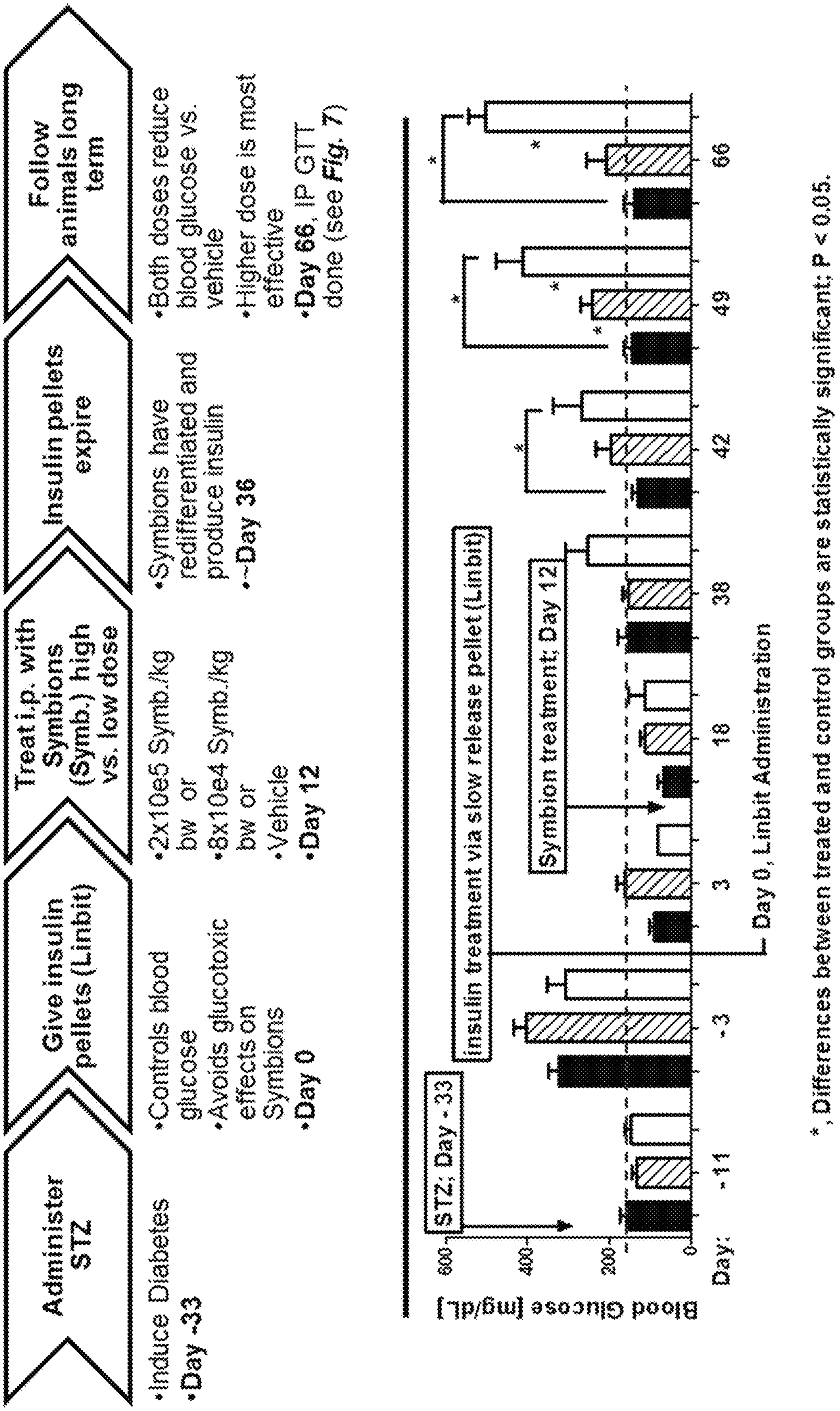
FIG. 12: Blood Glucose Profiles and Dose Finding Study in NOD/SCID mice treated i.p. three weeks after STZ-Induced Hyperglycemia, with vehicle or canine Neo-Islets. Both the $2\times10^5$ (black bars) and $8\times10^4$ Neo-Islets/kg bw (cross hatched bars) doses reduce blood glucose levels long term compared with vehicle treatment (open bars). However, $2\times10^5$ Neo-Islets/kg body weight ("bw") is a more effective dose.
Figure 13:
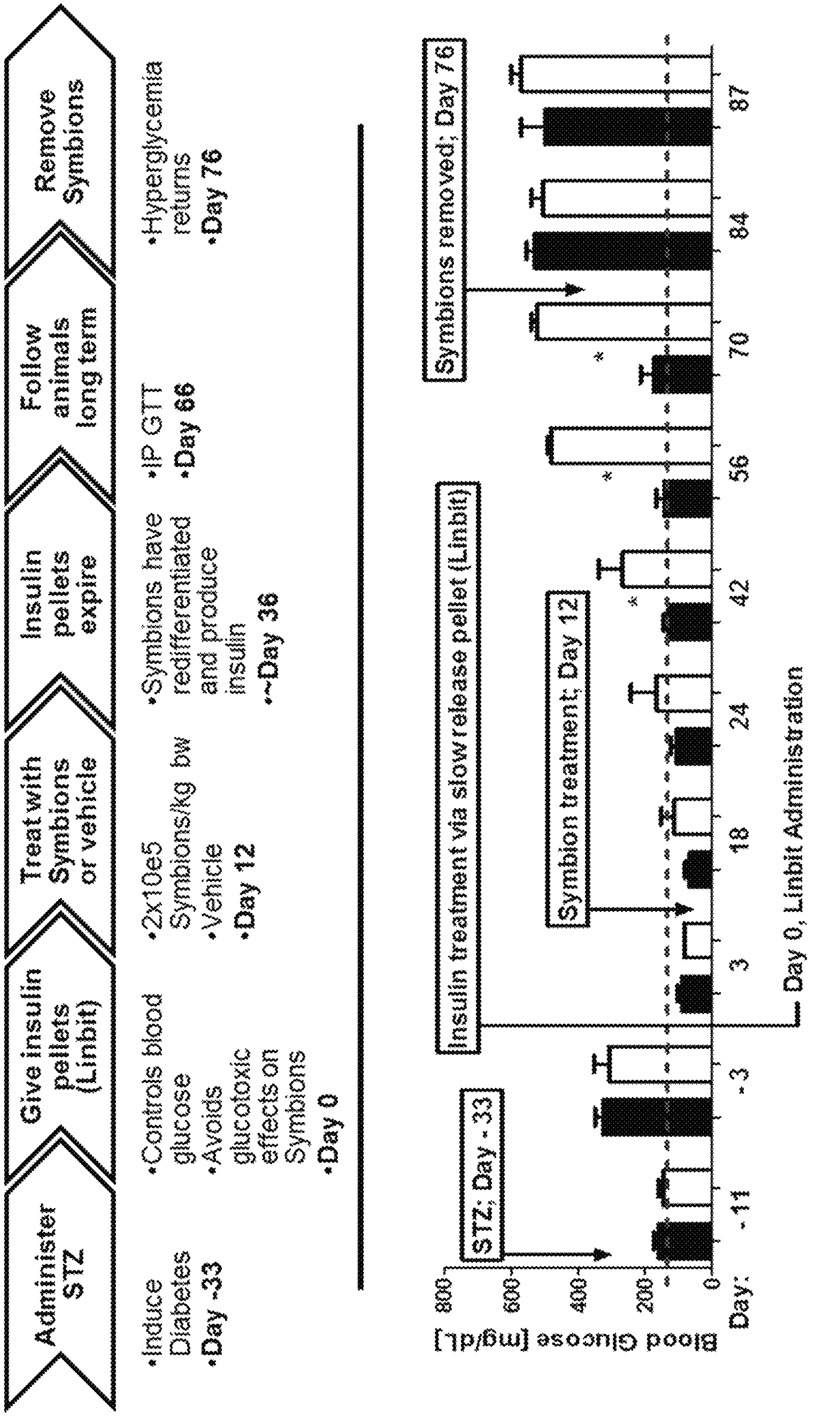
FIG. 13: Reversal of Euglycemia by removal of Canine Neo-Islets. Treatment i.p. of STZ diabetic NOD/SCID mice with canine Neo-Islets (black bars) causes sustained euglycemia compared to vehicle-treated animals (open bars), while removal of canine Neo-Islets from such treated animals results in return of hyperglycemia.

Diabetes Model: Non-obese diabetic/Severe Combined Immunodeficiency (NOD/SCID) mice were made diabetic with 5 i.p. doses of 50 mg/kg body weight Streptozotocin (STZ) in citrate buffer. Once blood glucose levels were >300 mg/dL on 3 separate days, they were given, on Day 0, one slow-release insulin pellet s.c. each (Linbit, Linshin, Canada) in order to control blood glucose levels and thereby avoid glucotoxic cell damage. These pellets expire by approximately 36 days (see FIG. 12). Animals were treated i.p. with (a) 200,000 or (b) 80,000 freshly formed, unredifferentiated canine derived Neo-Islets/kg body weight, or (c) vehicle (DMEM/F12). In some studies, NIs were surgically removed on day 76, and the mice were followed for an additional 2 weeks.

Intraperitoneal Glucose Tolerance Tests (GTT): At 55 days post treatment, 3 vehicle-treated and 5 canine Neo-Islet-treated mice were fasted 5 hours, whereupon baseline blood glucose levels were assessed using a OneTouch Ultra 2 Glucometer (Johnson and Johnson, New Brunswick, NJ; level of detection limit of 600 mg glucose/dL). Animals were then anesthetized, and 2 g glucose/kg bw (dissolved in serum free medium and filter sterilized) were administered via i.p. injection under isoflurane anesthesia. Blood glucose levels were assessed at 30 minutes, 60 minutes and 120 minutes post glucose administration.

Treatment Protocols

NOD allogeneic treatment: Once female NOD mice were confirmed to be hyperglycemic (non-fasting blood glucose >300 mg/dL on 3 separate days), they were treated s.c. with Linbit pellets. Once animals' blood glucose levels were normalized they were anesthetized (isoflurane), and Neo-Islets, composed of P5 gfp+ MSCs and P1 islet cells ($2\times10^5$ Neo-Islets/kg bw suspended in 0.5 ml serum-free DMEM-F12 medium; n=6) or vehicle (0.5 ml serum-free DMEM-F12 medium; n=3), were administered i.p. No subsequent exogenous insulin was given to animals in either group. Blood glucose levels and body weights were assessed twice per week, and mice were followed for 10 weeks. At 10 weeks post Neo-Islet administration, animals were sacrificed, and their sera, omenta, livers, spleens, lungs and kidneys and pancreases were harvested, and examined for the presence of Neo-Islets and insulin. None were found anywhere but the omenta.

C57Bl/6 syngeneic treatment of STZ diabetic animals: STZ-diabetic, blood glucose controlled (via Linbits) C57Bl/6 mice were anesthetized and administered i.p. either (a) $2\times10^5$ freshly formed gfp+ mouse Neo-Islets (P5 gfp+ MSCs and P1 islet cells) stained with DiR and suspended in 0.5 ml serum free DMEM-F12 (vehicle; n=3), or (b) $2\times10^5$ freshly formed gfp+ mouse Neo-Islets stained with DiR and embedded in gelfoam (n=3). Control group animals were anesthetized and treated i.p. with 0.5 ml vehicle (n=3). Blood glucose levels and weights were assessed at baseline and then twice per week in all animals for 18 weeks. Once per week, the animals were examined under isofluorane anesthesia using a Licor, Pearl Impulse imager to track the Neo-Islets. Upon sacrifice, omentum, pancreas, spleen, liver, lungs and kidneys were harvested and examined for the presence of Neo-Islets. None were found anywhere but the omenta.

Treatment of non-diabetic mice: Mouse Neo-Islet administration: Six groups of 2 to 4 non-diabetic, 12 week old female C57Bl/6 mice (average weight of 21.9 g) each were anesthetized and administered i.p. either (a) $2\times10^5$ freshly formed mouse Neo-Islets (P5 gfp+ MSCs and P1 islet cells) suspended in 0.5 ml serum-free DMEM-F12 (5 groups sacrificed at different time points for tracking purposes), or (b) 0.5 ml serum free DMEM-F12 (vehicle; 1 group). Blood glucose levels and weights were assessed at baseline and then twice per week for up to 12 weeks. Canine Neo-Islet administration: Two groups of non-diabetic, 9 week old, female NOD/SCID mice weighing 19.7 to 24.8 g were anesthetized administered i.p. either (a) $2\times10^5$ freshly formed, DiR stained canine Neo-Islets suspended in 0.5 ml DMEM/F12 (N=6) or (b) 0.5 ml serum free DMEM-F12 (vehicle; n=3). Blood glucose levels and weights were assessed at baseline and then twice per week for 10 weeks. Once per week, the animals were examined under isofluorane anesthesia using a Li-Cor, Pearl Impulse imager to track the Neo-Islets. Upon sacrifice, omentum, pancreas, spleen, liver, lungs and kidneys were harvested and examined for the presence of Neo-Islets. None were found anywhere but the omenta.

NOD/SCID recent onset diabetes, xenogeneic treatment: Groups of female, 20 week old, STZ-diabetic NOD/SCID mice weighing 17-29 g (n=5 per group) whose blood glucose levels were controlled with Linbit pellets were anesthetized and treated i.p. with (a) $2\times10^5$ or (b) $8\times10^4$ freshly formed, unredifferentiated cNeo-Islets/kg bw embedded in gelfoam, or (c) vehicle (DMEM/F12). Neo-Islets were composed of P1 Islet cells and P2 canine ASCs. Blood glucose levels and body weights were assessed twice per week, and mice were followed for 13 weeks. IP GTTs were performed in the high dose group at 55 days post treatment, and Neo-Islets were surgically removed from the high dose group of mice in week 10.

NOD/SCID remote onset diabetes, xenogeneic treatment: 11 week old female NOD/SCID mice weighing 18.4 to 22.8 g were made diabetic with three i.p. doses of 75 mg/kg body weight STZ in citrate buffer. The diabetic state was confirmed by blood glucose levels of >300 mg/dL on 3 separate days. Once the animals were confirmed to be diabetic, their blood glucose levels were controlled for approximately 3 months with insulin therapy using s.c. linbit pellets. To confirm that all animals were still diabetic prior to Neo-Islet or vehicle administration, Linbits were allowed to expire, and mice to re-develop hyperglycemia. Mice were again treated with Linbits (Day 0) to control blood glucose levels and prevent glucotoxic Neo-Islet damage. Anesthetized mice were then treated i.p. with either (i) $2\times10^5$ cNeo-Islets/kg b.w. embedded in gelfoam or (ii) vehicle (0.5 ml DMEM/F12). Neo-Islets were composed of P1 Islet cells and P2 canine ASCs. Blood glucose levels and body weights were assessed twice per week, and mice were followed for 11 weeks. IP GTTs: At 55 days post treatment, 3 vehicle-treated and 5 cNeo-Islet-treated mice were fasted 5 hours, whereupon baseline blood glucose levels were assessed. Animals were then anesthetized, and 2 g glucose/kg bw (dissolved in 0.5 ml serum free medium and filter sterilized) were administered via i.p. injection under anesthesia. Tail vein blood glucose levels were assessed at 30 minutes, 60 minutes and 120 minutes post glucose administration.

ELISA for Canine Insulin: Sera from vehicle and Neo-Islet-treated mice that had been collected during the glucose tolerance tests were examined by ELISA for the presence of canine specific insulin that does not cross react with mouse insulin (Mercodia, Uppsala, Sweden), following the manufacturer's instructions. Sera from a dog, as well as from a C56Bl/6 mouse were also analyzed as positive and negative controls, respectively, for cross-reactivity.

Antibody Response Test: Aliquots of ~$5\times10^4$ cells (MSCs, ASCs or islet cells that were used to create the Neo-Islets that were administered) were each incubated with ~500 μl of serum obtained from Neo-Islet or canine ASC-treated NOD mice >14 days post Neo-Islet or ASC administration. The cells were incubated with the sera for 30 minutes at room temperature. After 30 minutes cells were centrifuged at 600×g for 5 minutes, resuspended in FACS buffer and incubated with cy3-conjugated goat-anti-mouse (dilution) IgG antibody. The cells were incubated an additional 20 minutes in the dark at room temperature. One ml 1× PBS+ 1% BSA was then added, the cells vortexed, centrifuged, resuspended in 400 μl fixation buffer (1% Formaldehyde), and analyzed by FACS (BD FACScan Analyzer, San Jose, CA). A shift of >7% of the cells was considered a positive response, indicating that the serum contained antibodies to the tested cells. Embedding Neo-Islets in Gelfoam: Individual doses of Neo-Islets were collected in a 15 ml Falcon tube and centrifuge at 200×g for 2 minutes. The supernatants were discarded, and the pellets resuspended in 0.2 ml serum-free DMEM-F12 each. The Neo-Islet suspensions were then loaded into 0.5×0.5×0.5 cm blocks of sterile Gelfoam, which were incubated in a 37° C. incubator for 3 hours prior to i.p. administration to mice. Neo-Islet embedded in Gelfoam were surgically transplanted under sterile conditions and under anesthesia onto the peritoneal fat-pads and omenta of recipient mice. The abdominal incision was closed with two layer sutures.

In vivo Imaging: In vivo imaging of DiR stained Neo-Islets was performed in anesthetized mice using the Li-Cor, Pearl Impulse imager.

Results

Figure 15:
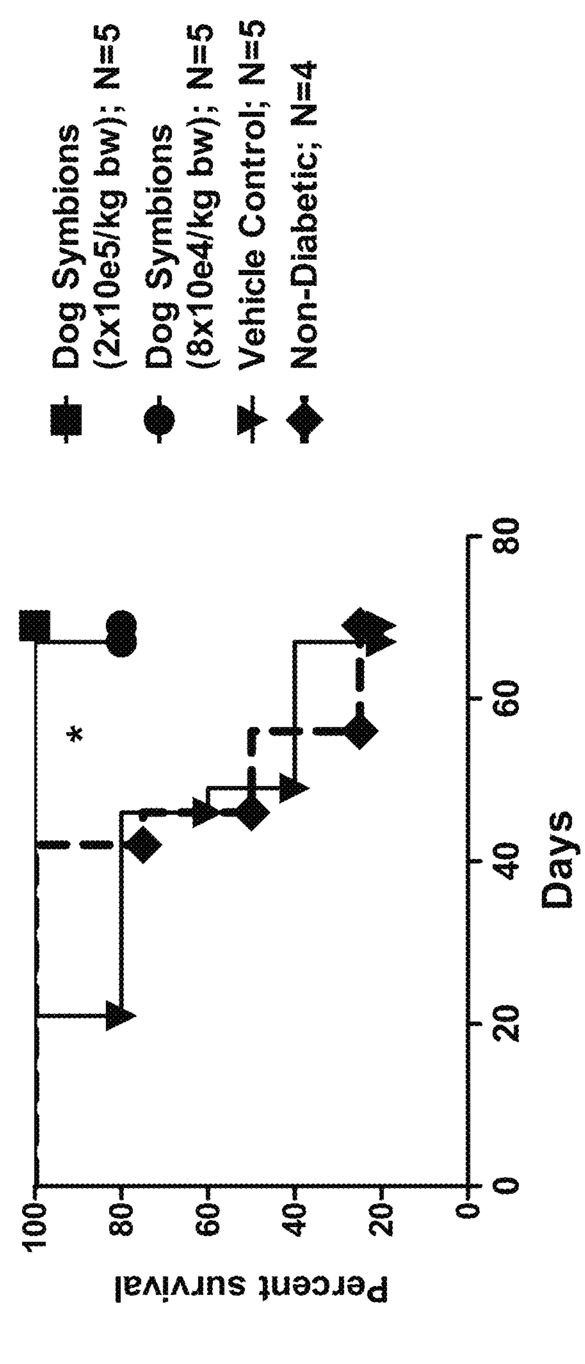
FIG. 15: Kaplan-Meier survival plots of diabetic NOD/SCID mice treated early after the development of diabetes with canine Neo-Islets or vehicle. Diabetic animals treated with either the $2\times10^5$ (squares) or $8\times10^4$ (circles) Neo-Islets/kg bw dose survive significantly longer than vehicle-treated (triangle), or, surprisingly, non-diabetic control (diamonds) animals.

A dose of $2\times10^5$ Neo-Islets/kg bw administered i.p. 1 month post STZ achieves and maintains euglycemia and promotes animal survival: Three groups of five NOD/SCID mice each were treated i.p. approximately one month after establishment of STZ-induced T1DM diabetes with (a) 200,000 or (b) 80,000 freshly formed, unredifferentiated canine derived Neo-Islets/kg body weight, suspended in 0.5 ml serum free medium (DMEM-F12), or (c) vehicle (0.5 ml serum free medium). Linbits were given once, ~1 month after STZ administration (Day 0 in FIGS. 12, 13, 14A, and 14B), and Neo-Islets or Vehicle were administered once blood glucose levels were stabilized, 12 days post Linbit administration. Vehicle-treated animals began to die by day 21, despite insulin therapy (see FIG. 15). As shown in FIGS. 12, 13, 14A, and 14B, once the Linbits wore off, remaining animals treated with vehicle (open bars) again became hyperglycemic. Neo-Islet-treated diabetic animals (black and cross hatched bars) showed normalized blood glucose levels, with the 200,000 Neo-Islets/kg bw dose more effectively controlling hyperglycemia than the 80,000 Neo-Islets/kg bw dose. As FIG. 15 demonstrates, mortality rates were significantly lower in the treated groups (squares and circles) than in either the vehicle-treated diabetic group (triangles) or, surprisingly, the healthy control, non-diabetic group (diamonds).

Figure 16:
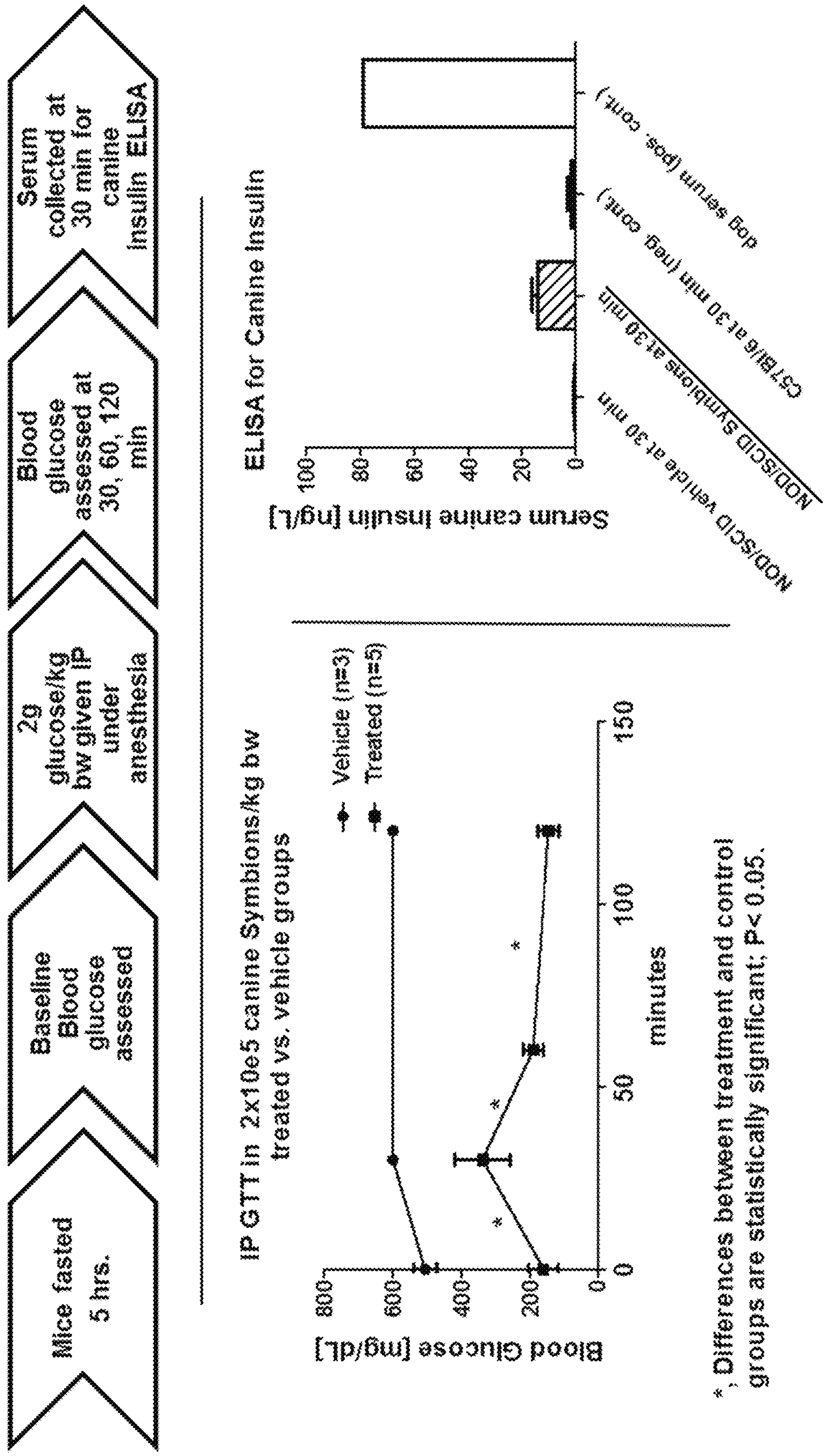
FIG. 16: Intraperitoneal Glucose Tolerance Test (IP GTTs) and Canine Insulin ELISA of Neo-Islet-treated NOD/SCID mice. Top: IP GTTs Experimental Protocol. Bottom Left: IP GTTs of $2\times10^5$ Neo-Islets/kg bw-treated (squares, n=5) vs. vehicle-treated NOD/SCID mice (circles, n=3). IP GTTs are normal in $2\times10^5$ Neo-Islets/kg bw-treated NOD/SCID mice, while blood glucose levels of vehicle-treated animals remain significantly elevated. Bottom Right: Canine-specific insulin ELISA conducted on duplicate samples of sera from vehicle (left bar, n=3) and canine Neo-Islet-treated (middle, cross-hatched bar, n=5) NOD/SCID mice that had been collected during the glucose tolerance tests, as well as sera from non-diabetic C57Bl/6 mice (middle black bar, n=2, negative control for ELISA specificity) and a healthy dog (open bar, positive control for ELISA specificity). In canine Neo-Islet-treated, but not vehicle-treated mice, a rise in blood glucose is accompanied by release of canine insulin, indicating that insulin release from the canine Neo-Islets is responsible for the normal IP GTTs.

Intraperitoneal glucose tolerance tests (IP GTTs) were normal in $2\times10^5$ Neo-Islets/kg bw-treated animals, and a rise in blood glucose was accompanied by release of canine insulin: IP GTTs (2 g glucose/kg bw) were performed at 54 days post canine Neo-Islet treatment (66 days post Linbit therapy) on NOD/SCID mice that had been treated with either the $2\times10^5$ canine Neo-Islets/kg body weight dose or vehicle as described in the Methods. As seen in FIG. 16, IP GTTs of Neo-Islet-treated animals were normal, whereas blood glucose levels of vehicle-treated mice remained elevated 2 hours post glucose administration.

Sera from vehicle and Neo-Islet-treated mice that had been collected during the glucose tolerance tests were examined by ELISA for the presence of canine specific insulin that does not cross react with mouse insulin as described in Methods. As can be seen in FIG. 16, canine insulin was detected in the sera of Neo-Islet-treated (cross hatched bar), but not vehicle-treated mice. The sera of healthy C57Bl/6 mice were tested as well to ensure there was no significant cross reactivity between canine and mouse insulin. No significant cross-reactivity was observed.

Retrieval of canine Neo-Islets reestablishes hyperglycemia: On Day 76, the Neo-Islets were removed from the $2\times10^5$ Neo-Islets/kg bw treatment group. As FIG. 13 demonstrates, removal of canine Neo-Islets resulted in reestablishment of hyperglycemia in this group of animals (black bars) similar to that of vehicle-treated animals (open bars).

Conclusion: The results presented in Example 6 demonstrate that freshly formed canine Neo-Islets administered i.p. to recent onset diabetic animals redifferentiate in vivo to provide adequate and physiologic insulin secretion and durable, but reversible, maintenance of euglycemia in rodents with T1DM. In addition the ability to remove the clusters via removal of the omentum is a safety feature of this technology when clinically warranted.

Example 8: Neo-Islet Tracking and Angiogenesis

Rationale: (A) It is well known that the Omentum accumulates cells and foreign bodies of various sizes. Thus we hypothesized and tested whether the Neo-Islets when delivered i.p. would be taken up by and engraft in the Omentum. Such a location offers two advantages: (i) As is the case for the pancreas, blood from the Omentum drains directly into the liver via the portal system. Thus insulin made by the Neo-Islets would be delivered in physiological fashion. (ii) The Omentum can be removed without significant ill effects, should it be desired for safety or other reasons that the Neo-Islets be removed. (B) As MSCs and ASCs express potent angiogenic and survival factors, we also examined whether the stem cell component of the engrafted Neo-Islets enhanced the development of a blood supply for the Neo-Islets.

Methods

Mouse Neo-Islets were generated from co-culture in low adherence vessels of P2 Islet cells derived from wild-type C57Bl/6 mice and P5 MSCs derived from C57Bl/6 mice transgenic for the $GFP^+$ gene to facilitate tracking of the Neo-Islets in vivo. As indicated below, in one group of experiments, after formation, the Neo-Islets were stained with the Infrared light-excitable carbocyanine probe DiR (Molecular Probes, Eugene, OR) to allow for tracking in vivo.

Dog Neo-Islets were formed from co-culture in low adherence vessels of P2 dog islet cells and P4 dog ASCs that had been stained with DiR to allow for tracking in live animals.

Diabetes model and allogeneic treatment: Female Non-Obese Diabetic (NOD) mice spontaneously develop T1DM at approximately 12-20 weeks of age. Once female NOD mice were confirmed to be hyperglycemic (blood glucose >300 mg/dL on three separate days), they were treated s.c. with Linbit pellets. Once animals' blood glucose levels were normalized, Neo-Islets ($2\times10^5$ Neo-Islet/kg bw suspended in 0.5 ml serum free DMEM-F12 medium) or vehicle (0.5 ml serum free DMEM-F12 medium) were administered i.p. to groups of five animals each. No subsequent exogenous insulin was given to animals in either group. Blood glucose levels and body weights were assessed twice per week, and mice were followed for 10 weeks. At 10 weeks post Neo-Islet administration, animals were sacrificed, and their sera, omenta, livers, spleens, kidneys and pancreases harvested.

Canine Neo-Islet administration: DiR labeled dog Neo-Islets were administered i.p. to 6 NOD/SCID mice, and the mice were examined weekly for 10 weeks under isoflurane anesthesia using a Li-Cor Pearl Impulse™ imager to track the Neo-Islets.

Syngeneic Neo-Islet administration: Two syngeneic administration experiments were performed, one in non-diabetic animals, and another in diabetic animals.

A) Non-diabetic animals: Six groups of non-diabetic C57Bl/6 mice were administered i.p. either (a) $2\times10^5$ freshly formed gfp+ mouse Neo-Islets suspended in 0.5 ml serum free DMEM-F12 (5 groups), or (b) 0.5 ml serum free DMEM-F12 (vehicle; 1 group). Blood glucose levels (OneTouch Ultra 2 glucometer) and weights were assessed at baseline and then twice per week in all animals. At various time points up to 12 weeks, groups of animals were sacrificed and their sera, omenta, livers, spleens, lungs, kidneys and pancreases harvested.

B) Diabetic animals: Two groups of STZ-diabetic C57Bl/6 mice were administered i.p. either (a) $2\times10^5$ freshly formed gfp+ mouse Neo-Islets stained with DiR and suspended in 0.5 ml serum free DMEM-F12, or (b) 0.5 ml serum free DMEM-F12 (vehicle). Blood glucose levels (OneTouch Ultra™ 2 glucometer) and weights were assessed at baseline and then twice per week in all animals for 13 weeks. Once per week, the animals were examined under isoflurane anesthesia using a Licor, Pearl Impulse imager to track the Neo-Islets.

Immunohistochemistry: Omenta and other organs were harvested, fixed and embedded as previously described.[13] Omental sections were deparaffinized and stained by immunohistochemistry for DNA with 4', 6-diamidino-2-phenylindole (DAPI, Molecular Probes, Eugene, OR) and insulin protein using a guinea-pig anti-insulin antibody (Dako, Carpinteria, CA), and a $cy^3$-conjugated anti-guinea pig antibody (Jackson ImmunoResearch, West Grove, PA) following the manufacturers' instructions.

Results

Neo-Islets spontaneously engraft in the murine Omentum and produce Insulin. We hypothesized that injected NIs would home to, attach to, and engraft in the mice' well-vascularized omenta, which would offer the advantage of physiologic insulin secretion into the portal system of the liver. Indeed, as shown in FIG. 18A, fluorescence in vivo imaging of a euglycemic NOD mouse treated 10 weeks previously with DiR labeled NIs demonstrates their persistent location in the upper abdomen.

Figure 17:
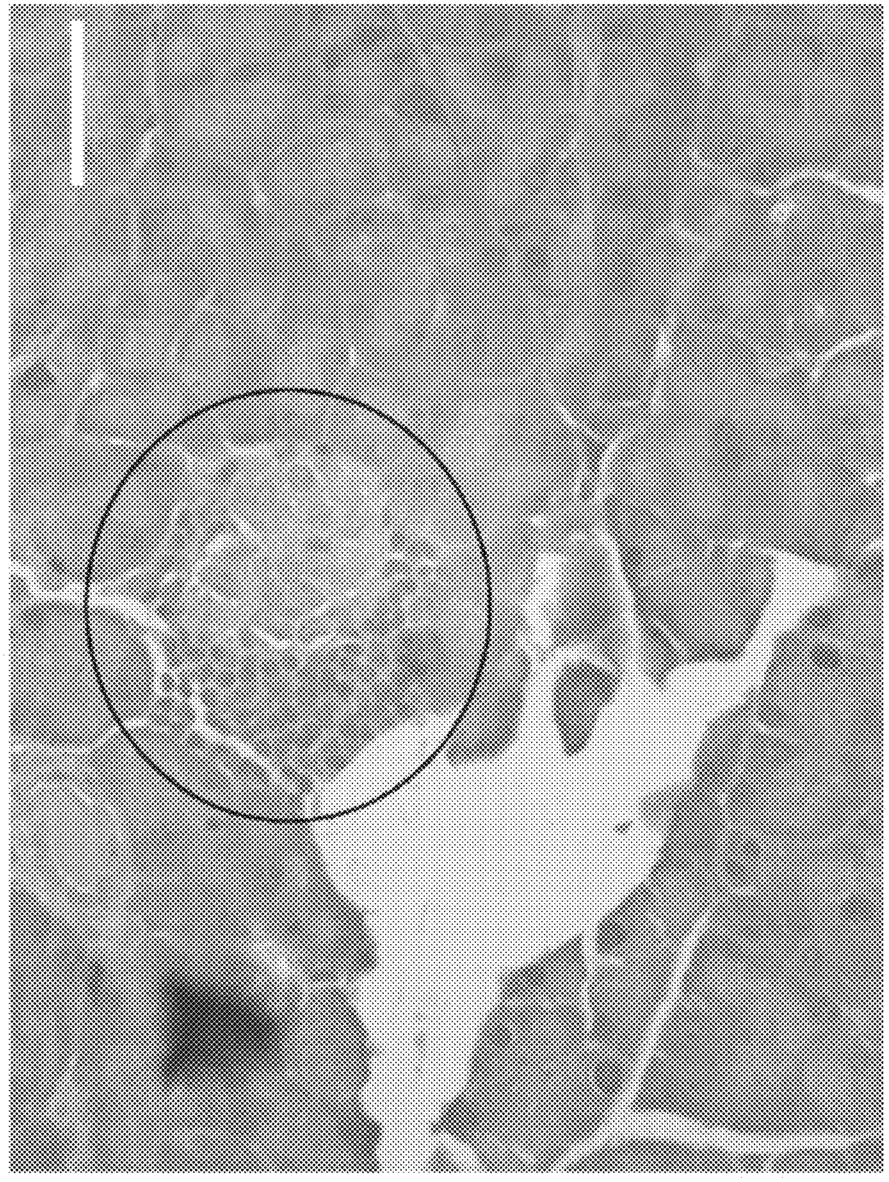
FIG. 17: Insulitis remains in NI-treated NOD mice. Representative image (40×) of a Hematoxylin Eosin stained pancreatic section from a euglycemic, NI-treated NOD mouse 11 weeks post treatment demonstrating the presence of persistent, high-grade insulitis (black circle). Scale bar (white)=200 μm.
Figure 18A:
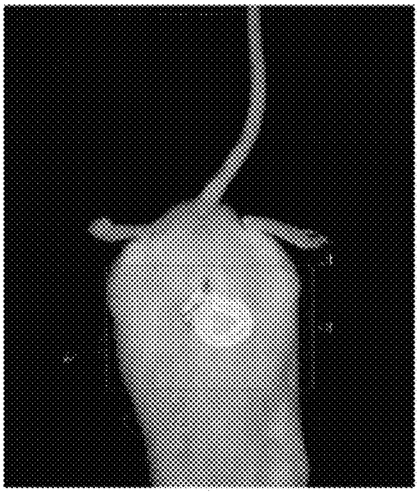
FIGS. 18A-18C. NI engraftment, survival, and insulin expression in NOD mice.
Figure 18B:
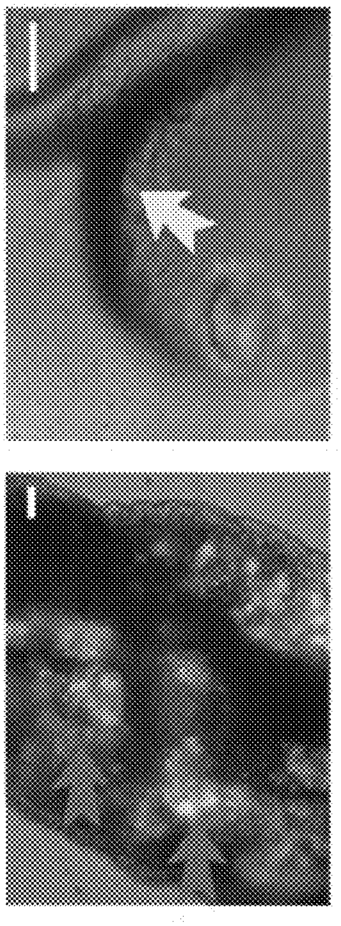
Figure 18C:
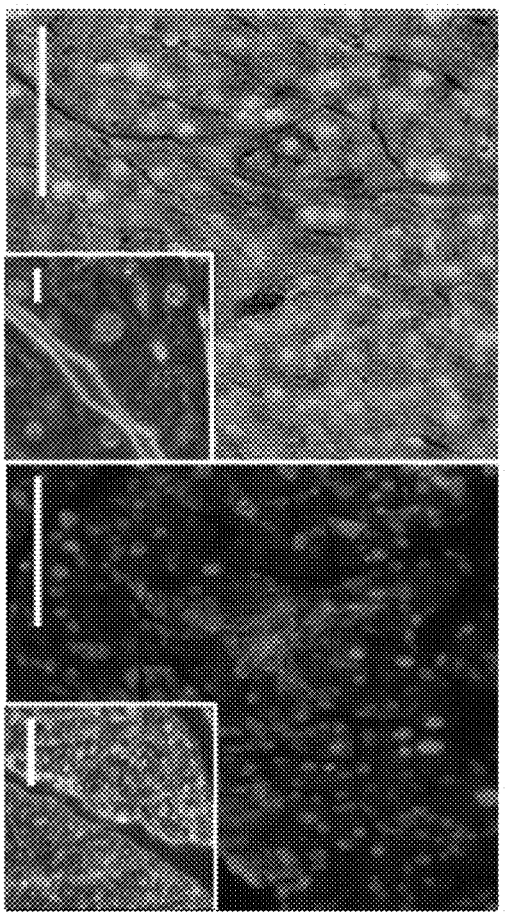

To further assess the intraperitoneal engraftment pattern and function of DiRlabeled, eGFP+ NIs as detected in FIG. 18A, upon euthanasia of the NI-treated NOD mice from the experiment shown in FIG. 9, we examined histologically the omenta, pancreata, spleens, livers, lungs and kidneys for the presence of eGFP+Ms. NIs were detected only in the animals' omenta (FIG. 18B). Furthermore, sections of the omentum stained positive for insulin (FIG. 18C, left panel), while negative controls (FIG. 18C, inset) and omenta from vehicle treated, diabetic NOD mice showed no insulin staining (FIG. 18C, right panel). Pancreata were shown to have high-grade insulitis, as expected (FIG. 17), indicating that euglycemia was not achieved through islet recovery, but rather through physiologic insulin secretion by the omentally engrafted NIs. Importantly, there was no histologic evidence for tumor formation or ectopic maldifferentiation (adipo-, osteo-, chondrogenic) in any of the examined organs.

Conclusion: Taken together, the foregoing results demonstrate that across species: (i) Neo-Islets that are administered i.p. engraft in the omentum where they remain long term, redifferentiate, secrete insulin in physiologic fashion and are not rejected. (ii) The angiogenic properties of the stem cell component of the Neo-Islet helps vascularize the Neo-Islets, providing them with needed oxygen, nutrition, and optimized delivery of insulin from the Neo-Islets into the portal vein of the liver.

Example 9: Neo-Islet Treatment of Remote Onset Diabetics

Rationale: We showed in Example 5 that the Neo-Islets are effective in treating recent onset T1DM. We tested here whether Neo-Islets were also effective in treating remote onset T1DM.

Methods

Neo-Islets: Neo-Islets were formed from canine ASCs (passage 2) and canine cultured islet cells (passage 1).

Diabetes Model: Non-obese diabetic/Severe Combined Immunodeficiency (NOD/SCID) mice were made diabetic with 3 i.p. doses of 75 mg/kg body weight Streptozotocin (STZ) in citrate buffer. The diabetic state was confirmed by blood glucose levels of >300 mg/dL on 3 separate days. Once the animals were confirmed to be diabetic, their blood glucose levels were controlled for approximately 3 months with insulin therapy using s.c. linbit pellets. To confirm that all animals were still diabetic prior to the Neo-Islet or vehicle administration, Linbits were allowed to expire, and all mice re-developed hyperglycemia. Mice were again treated with Linbits (Day 0 on FIG. 19 to control blood glucose levels and prevent glucotoxic cell damage.

IP GTTs and Insulin ELISAs—were carried out as described in Example 5, and results were combined with those of animals in Example 6 (recent onset) and presented in FIG. 16.

Results

Figure 19:
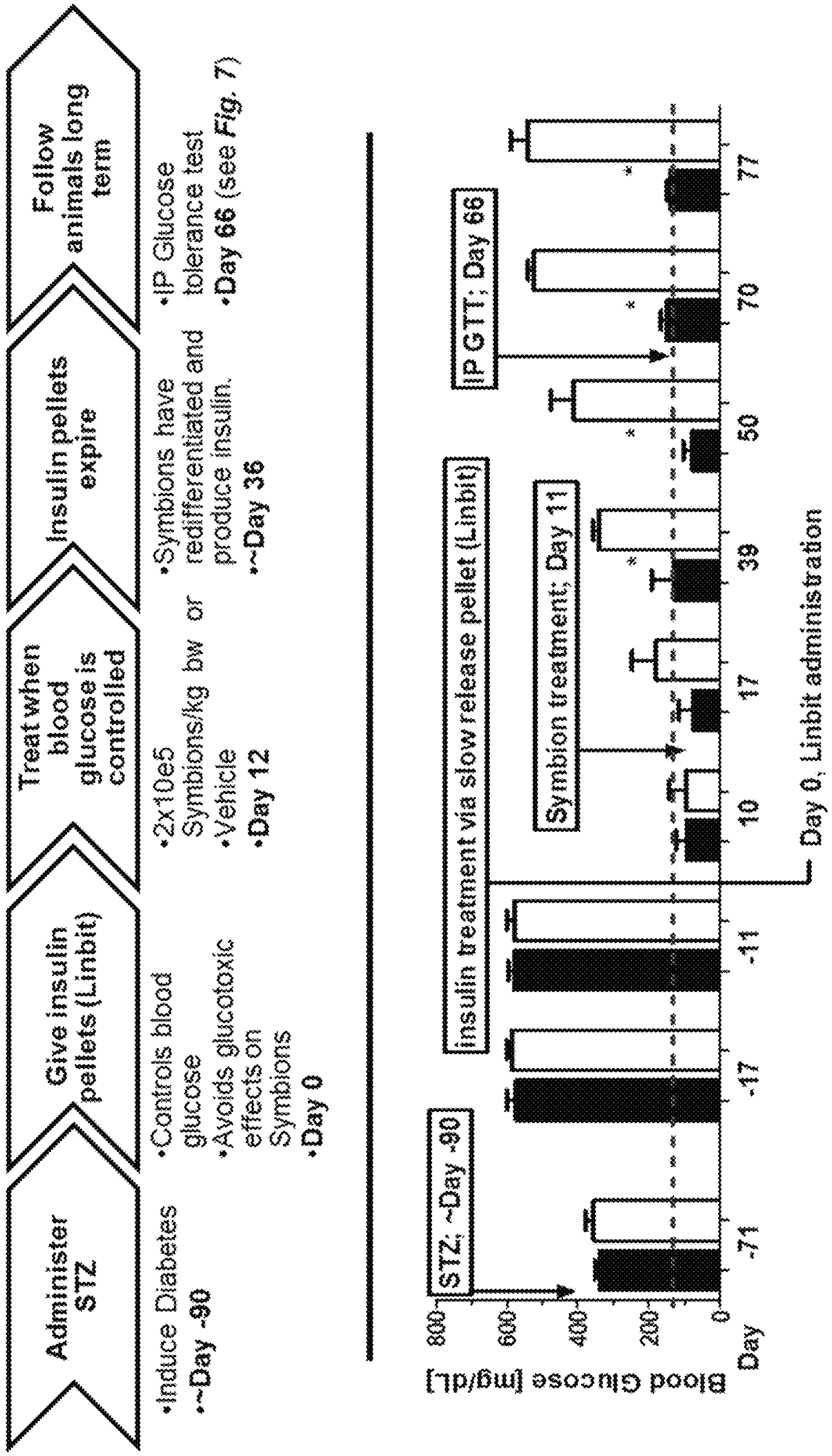
FIG. 19: Blood Glucose Levels of canine Neo-Islet-treated STZ-diabetic NOD/SCID mice. Animals were treated with Neo-Islets 3 months post onset of diabetes and followed Long-term. Animals with established diabetes exhibit normoglycemia following treatment with canine Neo-Islets (black bars), while those treated with vehicle (open bars) remain hyperglycemic after insulin release by Linbits expires on—Day 36. This demonstrates that Neo-Islets are effective in establishing euglycemia in remote onset diabetes.

Two groups of 5 diabetic NOD/SCID mice each were treated i.p. at 3 months after STZ-induced T1DM with (a) 200,000 freshly formed canine derived Neo-Islets/kg body weight suspend in 0.5 ml serum free medium (DMEM-F12) or (b) vehicle. An overview of the experimental design is given in FIG. 19. As shown in FIG. 19, animals with remote onset diabetes exhibit normoglycemia following treatment with canine Neo-Islets (black bars), while those treated with vehicle (open bars) remain hyperglycemic once their insulin pellets expire.

Conclusion: The above data demonstrate that, as is the case with recent onset diabetes, Neo-Islets are also effective in establishing euglycemia in remote onset diabetes.

Example 10: Treatment of Spontaneously Diabetic NOD Mice with Allogeneic Mouse Neo-Islets Rationale: We showed in Examples 5 and 7 that canine Neo-Islets can reverse STZ induced diabetes in NOD/SCID mice. While the NOD/SCID data presented above indicate that Neo-Islets generated from canine derived cells are capable of safely and effectively undergoing redifferentiation in vivo to produce insulin and secrete it in physiologic fashion long-term, the NOD/SCID model does not address the issues of protection of the transplanted cells from diabetogenic autoimmune and allo-immune attacks. ASCs and MSCs exhibit powerful immune modulating properties.[16] We hypothesized the stem cell component of the Neo-Islets would provide local immune isolation, and tested whether the Neo-Islets could restore euglycemia when administered allogeneically to spontaneously diabetic NOD mice.

Methods

Mouse Neo-Islets were generated from co-culture in low adherence vessels of P2 Islet cells derived from wild-type C57Bl/6 mice and P5 MSCs derived from C57Bl/6 mice transgenic for the $GFP^+$ gene.

Spontaneous diabetes model and allogeneic treatment: Once female NOD mice were confirmed to be hyperglycemic (blood glucose >300 mg/dL on 3 separate days), they were treated s.c. with Linbit pellets. Once animals' blood glucose levels were normalized, Neo-Islets ($2\times10^5$ Neo-Islet/kg bw suspended in 0.5 ml serum free DMEM-F12 medium) or vehicle (0.5 ml serum free DMEM-F12 medium) were administered i.p. to groups of 5 animals each. No subsequent exogenous insulin was given to animals in either group. Blood glucose levels and body weights were assessed twice per week, and mice were followed long term.

Results

Figure 20:
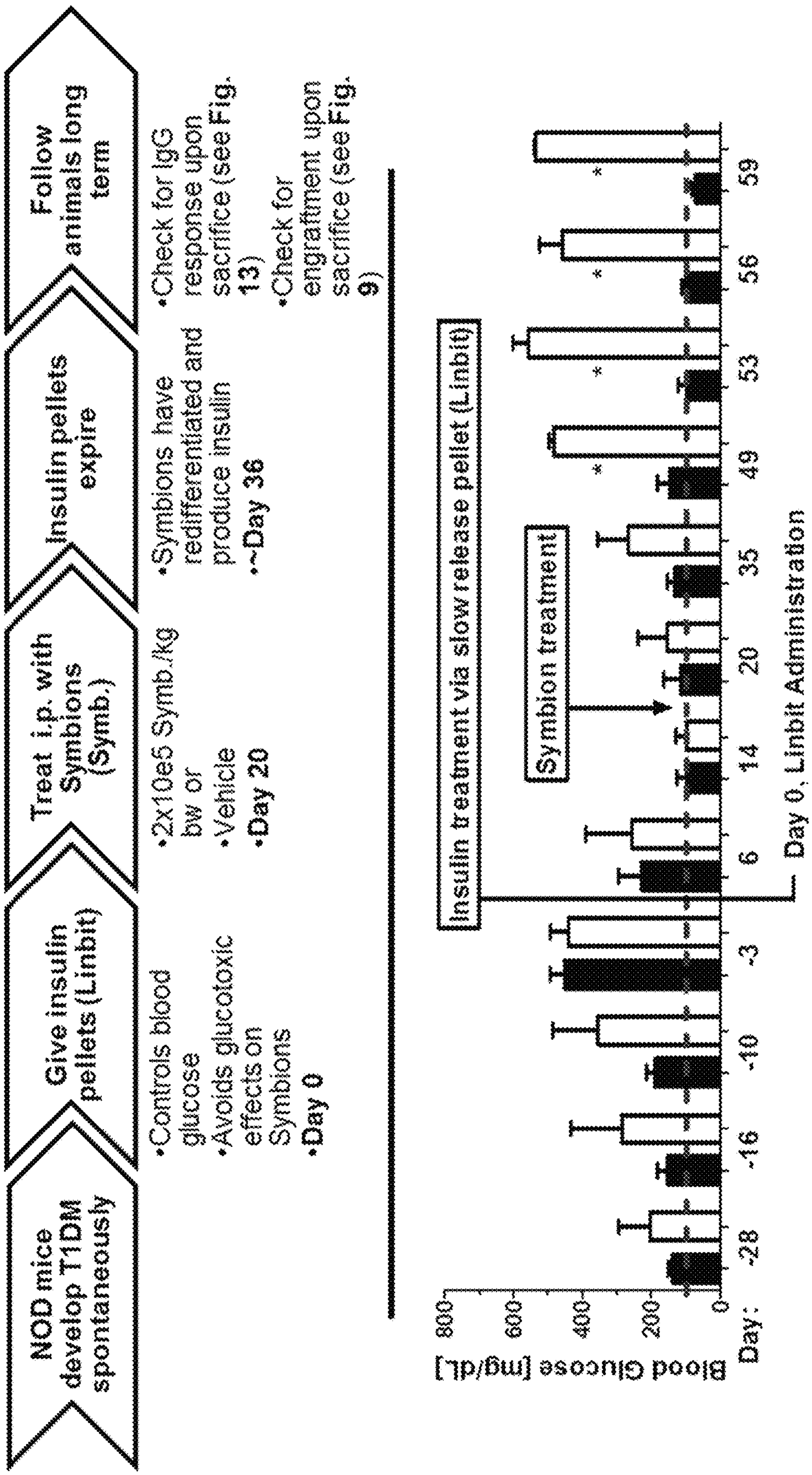
FIG. 20: Blood glucose levels of autoimmune T1DM NOD mice treated with allogeneic Neo-Islets. Spontaneously diabetic female NOD mice were treated with slow-release insulin pellets (Linbits, s.c.) to control hyperglycemia. On Day 20 post Linbit therapy, mice were treated with allogeneic Neo-Islets derived from C57Bl/6 mice (generated from P2 islet cells and P5 gfp+ MSCs; n=5; black bars) or vehicle (n=3; open bars). These data clearly demonstrate that euglycemia is maintained as a consequence of Neo-Islet induced immune isolation against both allo- and autoimmune attacks.

A dose of 200,000 allogeneic Neo-Islets/kg bw administered i.p. achieves and maintains euglycemia in spontaneously diabetic NOD mice. Blood glucose levels of vehicle and Neo-Islet-treated NOD mice are shown in FIG. 20. To summarize, blood glucose levels were normalized in mice treated with allogeneic Neo-Islets (black bars), while vehicle-treated mice (open bars) remained hyperglycemic.

Conclusion: These data demonstrate that, like the canine Neo-Islets, mouse Neo-Islets (i) redifferentiate in vivo to provide adequate insulin secretion to reestablish and maintain euglycemia, and importantly (ii) that they afford immune isolation against both allo- and auto-immune attacks without encapsulation, as hypothesized.

Example 11: Neo-Islets do not Induce Hypoglycemia in Non-Diabetic Mice

Rationale: From the previous examples, it is apparent that the Neo-Islets engraft in the omentum where they redifferentiate to produce and secrete insulin. However, if insulin secretion were to be constitutive and non-physiologic, this could potentially lead to episodes of hypoglycemia. We tested, therefore, whether administration of Neo-Islets to non-diabetic animals would result in hypoglycemia.

Methods

Mouse Neo-Islets were generated from co-culture in low adherence vessels of P2 Islet cells derived from wild-type C57Bl/6 mice and P5 MSCs derived from C57Bl/6 mice transgenic for $GFP^+$ gene.

Dog Neo-Islets were formed from co-culture in low adherence vessels of P2 dog islet cells and P4 dog ASCs.

Mouse Neo-Islet administration: Six groups of 2 to 4 non-diabetic C57Bl/6 mice each were administered i.p. either (a) $2\times10^5$ freshly formed mouse sNeo-Islets suspended in 0.5 ml serum free DMEM-F12 (5 groups), or (b) 0.5 ml serum free DMEM-F12 (vehicle; 1 group). Blood glucose levels (OneTouch Ultra 2 glucometer) and weights were assessed at baseline and then twice per week for up to 12 weeks.

Canine Neo-Islets: Two groups of NOD/SCID mice were administered i.p. either (a) $2\times10^5$ freshly formed dog Neo-Islets (N=6) or (b) 0.5 ml serum free DMEM-F12 (vehicle; N=3). Blood glucose levels (OneTouch Ultra 2 glucometer) and weights were assessed at baseline and then twice per week for 10 weeks.

Results

Figure 21:
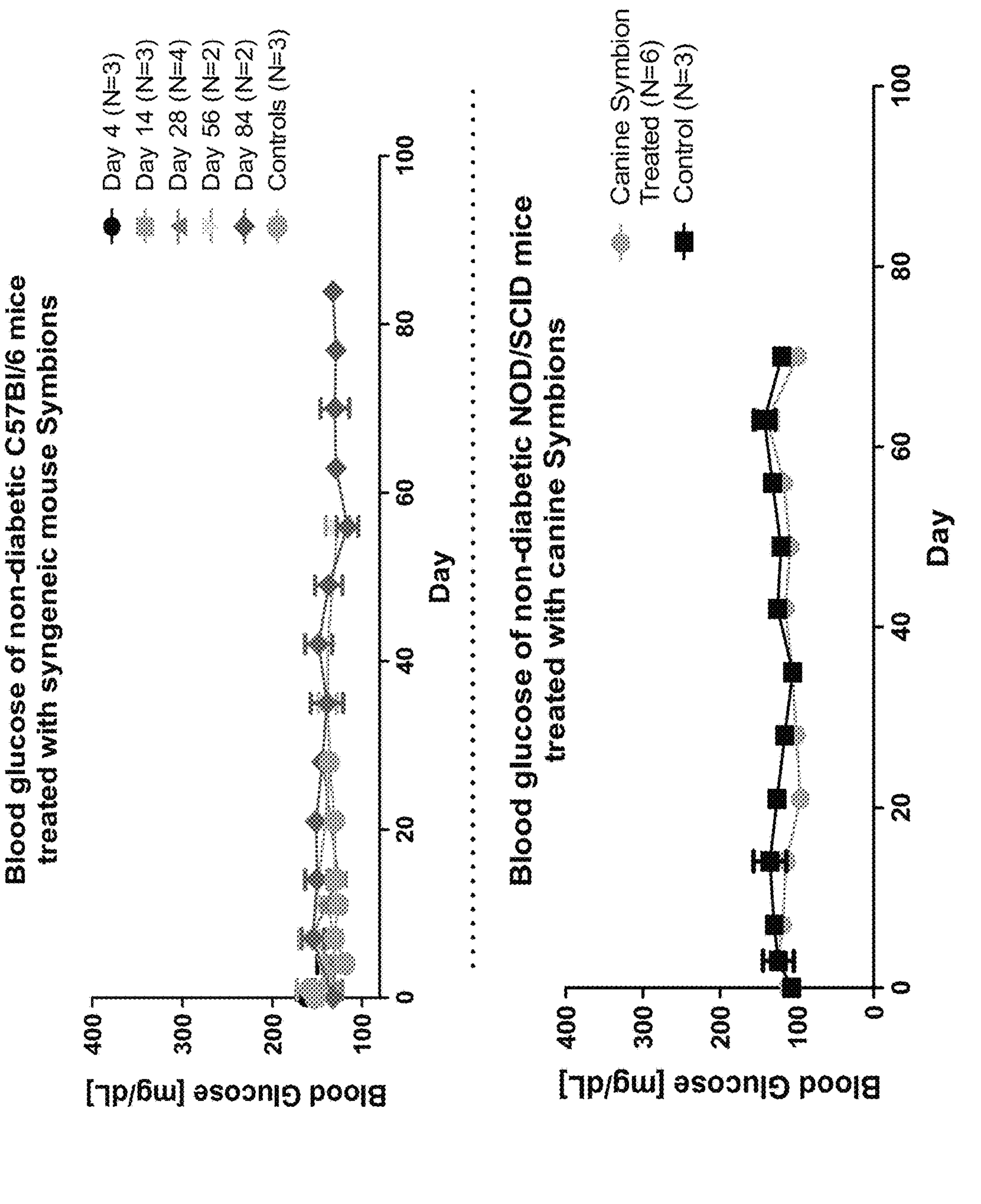
FIG. 21: Neo-Islets do not induce hypoglycemia in non-diabetic mice. Top Panel: $2\times10^5$ Neo-Islets/kg bw derived from C57Bl/6 mice were administered i.p. to non-diabetic C57Bl/6 mice. Treated animals were followed for up to 12 weeks. Blood glucose levels were assessed weekly. No hypoglycemia was observed at any time point, demonstrating physiologic insulin release by mouse Neo-Islets. Neo-Islets remain engrafted and were not rejected. Bottom Panel: Blood glucose levels of NOD/SCID mice treated i.p. with either (a) $2\times10^5$ freshly formed DiR labeled dog Neo-Islets (P2 dog islet cells+P4 dog ASCs; grey line; n=6) or (b) 0.5 ml serum free DMEM-F12 (Control; black line; n=3). Neo-Islets remain engrafted (see FIG. 18A). No hypoglycemia was observed at any time point. These data further demonstrate physiologic insulin release by dog Neo-Islets.

Neo-Islets do not cause hypoglycemia in non-diabetic mice. As shown in Example 8 and FIG. 18B, i.p. administered mouse or dog Neo-Islets engraft in the omentum. As can be seen in FIG. 21, upper panel, blood glucose levels of C57Bl/6 mice that were treated with mouse Neo-Islets remain normal and comparable to those of vehicle-treated mice. Similar results were obtained for NOD/SCID mice treated with canine Neo-Islets (FIG. 21, lower panel).

Conclusion: These data demonstrate that engrafted Neo-Islets formed from either mouse or canine cells release insulin physiologically and not constitutively.

Example 12: Allogeneic MSCs and Cultured Islet Cells Contained in the Neo-Islets do not Elicit an Antibody Response in Recipients Rationale: The preceding examples indicate the Neo-Islets described herein may be used allogeneically to reestablish normoglycemia in diabetic animals without rejection. The following study was undertaken to further test whether animals treated allogeneically with Neo-Islets produce antibodies to either of the cell types that make up the Neo-Islets.

Methods

Mouse Neo-Islets were generated from co-culture in low adherence vessels of P2 Islet cells derived from wild-type C57Bl/6 mice and P5 MSCs derived from C57Bl/6 mice.

Antibody Response Test: Test sera were incubated with either: (a) $1\times10^5$ gfp+C57Bl/6 MSCs, or (b) $1\times10^5$ cultured C57Bl/6 islet cells for 30 minutes. Positive control sera were incubated with $1\times10^5$ canine ASCs. After incubation with serum, the cells were centrifuged, resuspended in FACS buffer and incubated with Phycoerythrin (PE) labeled anti-mouse IgG antibody (Pharmingen, San Diego, CA). The cells were incubated an additional 20 minutes in the dark at room temperature. One m 1×PBS (Roche, Indianapolis, IN)+1% BSA (Sigma, St. Louis, MO) was then added. The cells were vortexed, then centrifuged, resuspended in fixation buffer (1% Formaldehyde), and analyzed by FACS (BD FACScan Analyzer, San Jose, CA; 10,000 cells counted).

Results

Sera were obtained from:

(i) NOD mice that had been treated i.p. with $2\times10^5$ Neo-Islet/kg bw 12 weeks post Neo-Islet treatment (see Example 8), (ii) NOD mice that had been treated i.p. with vehicle 12 weeks post vehicle treatment (see Example 8), and (iii) NOD mice that had not been infused (naïve mice).

Mouse MSCs from Neo-Islets and mouse islet cells from the Neo-Islets were incubated with the collected sera, and then with Phycoerythrin (PE) labeled anti-mouse IgG antibody. The serum-exposed cells were then analyzed by FACS as described above in Methods to determine whether any IgG antibodies to administered MSCs or islet cells were present in the sera of treated mice.

As xenogeneic administration of ASCs is known to elicit an immune response, canine ASCs that had been exposed to sera from NOD mice 14 days post canine ASC administration were incubated with PE labeled anti-mouse IgG antibody, analyzed by FACS, and used as positive controls.

If Neo-Islet-treated mice had developed an allo-immune response to the MSCs or the islet cells in the Neo-Islets, then the PE-labeled α-mouse IgG antibody would bind to the serum exposed cells, and the cells would appear shifted (PE positive) on FACS analysis. A shift of >7% of the cells (% of PE positive cells) on FACS was considered a positive allo-antibody response.

Figure 22A:
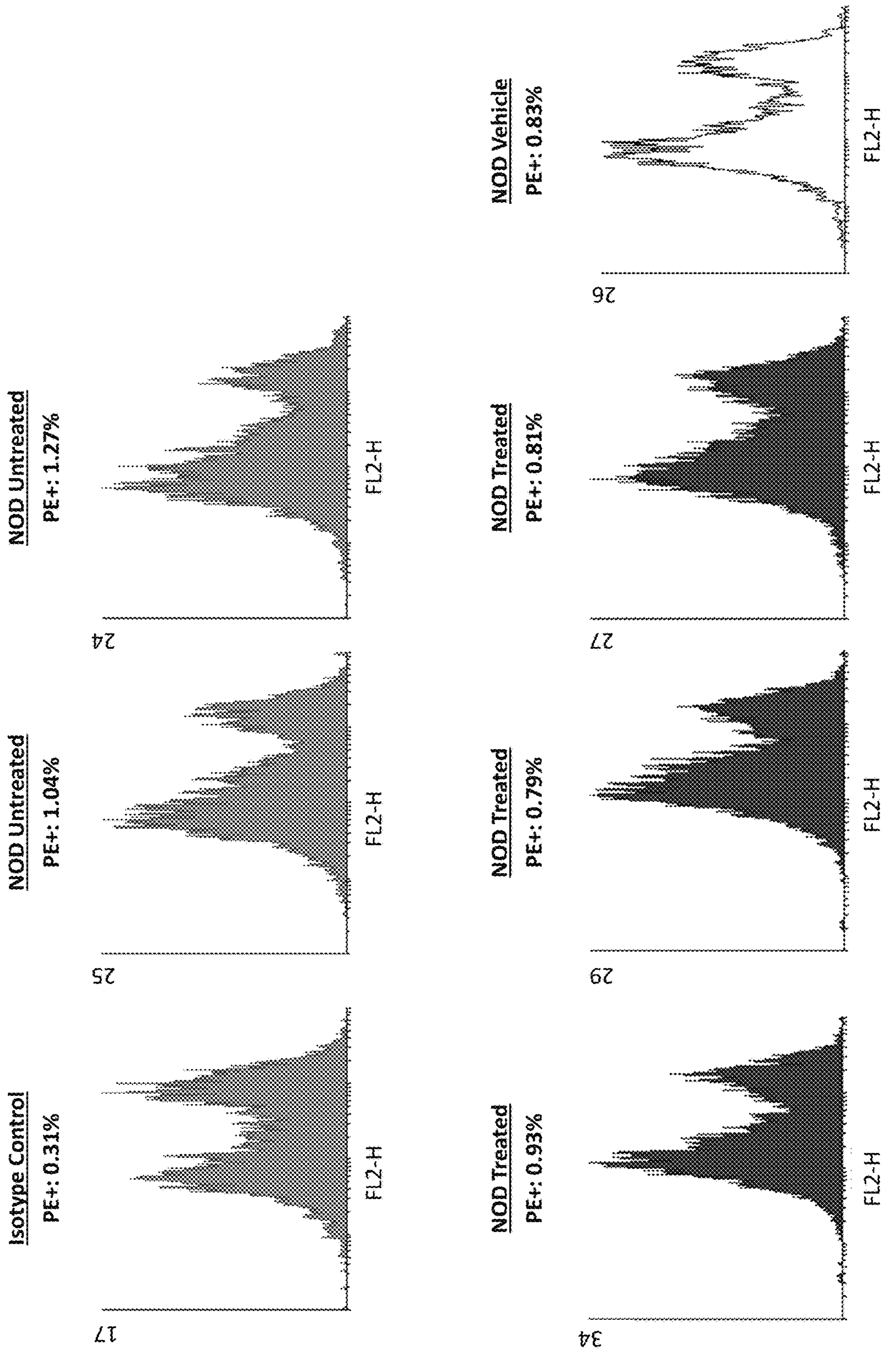
FIGS. 22A-22C: Neither MSCs nor cultured islet cells contained in allogeneic Neo-Islets induce antibody formation. In all panels, cells were incubated with sera from control or treated mice and then with Phycoerythrin-labeled (PE) anti-mouse IgG, then analyzed by FACS. In Panels A and B, sera were collected from NOD mice that were rendered euglycemic by Neo-Islet treatment 12 weeks post treatment, or from vehicle-treated or untreated, control NOD mice.
Figure 22B:
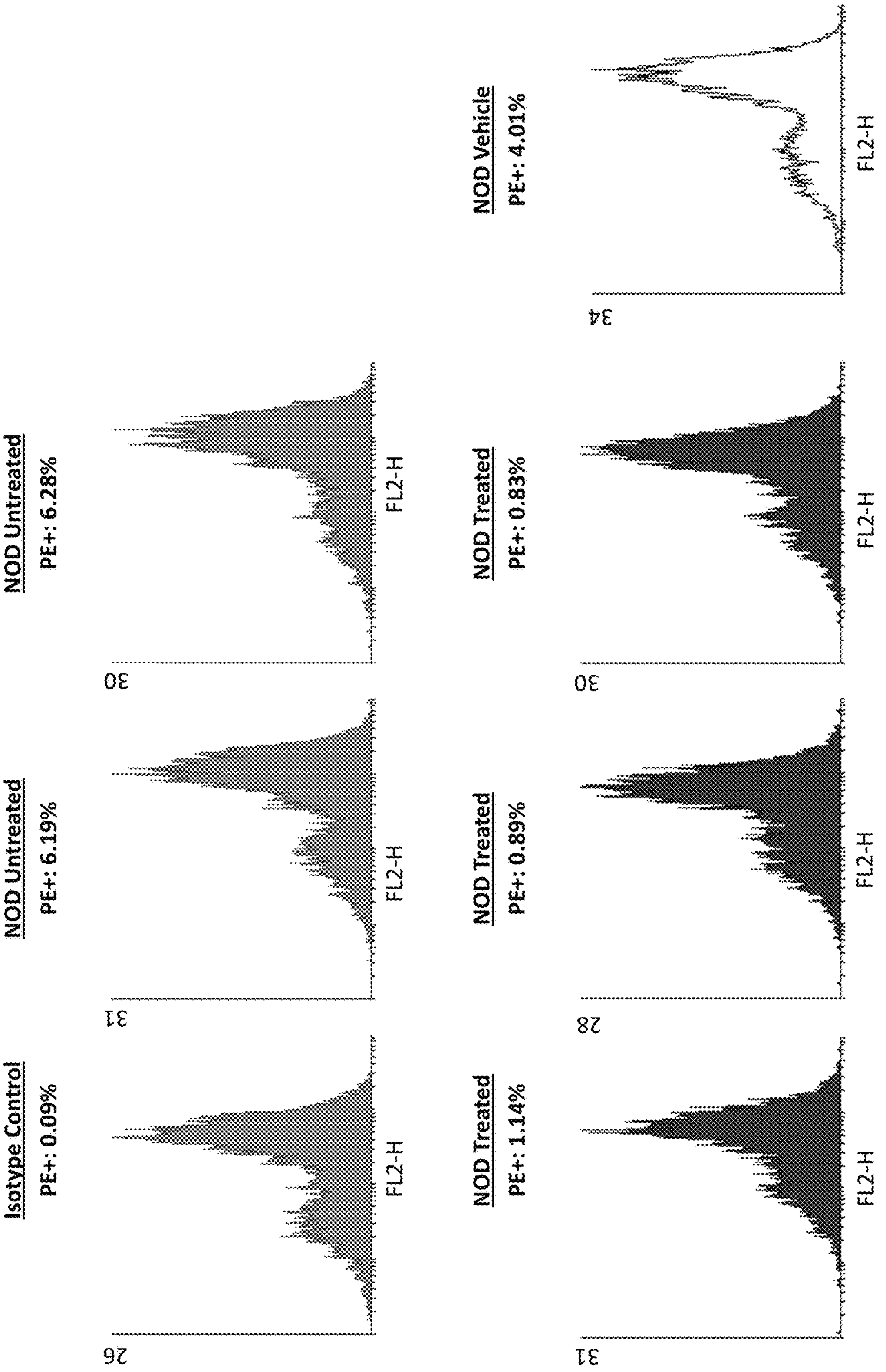
Figure 22C:
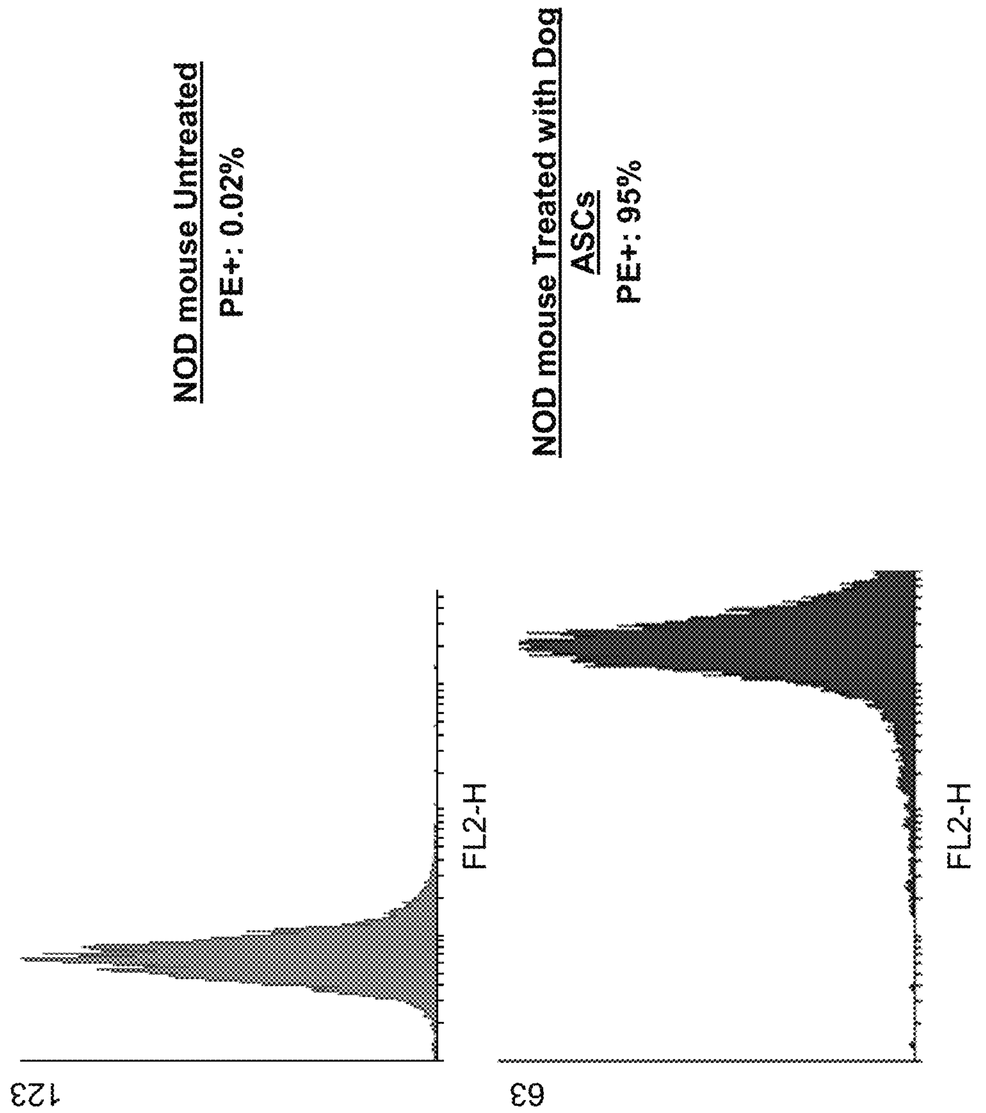

As shown in FIGS. 22A-22C, sera from allogeneic Neo-Islet-treated mice contained no IgG antibodies to the allogeneic, mouse MSCs (FIG. 22A) or islet cells (FIG. 22B). In addition, these data suggest that sera from vehicle-treated NOD mice contained no preformed IgG antibodies against MSCs or dedifferentiated islet cells. As expected, sera from mice treated with canine ASCs (positive control) did contain high levels of IgG antibodies to the canine ASCs as evidenced by a shift in 95% of the cells (FIG. 22C).

NOD mice do not mount an allo-immune IgG Response to the MSCs and Islet Cells of NIs. To examine whether islet cells and MSCs contained in the NIs are protected from a humoral immune attack, we assessed whether sera from normoglycemic, NI-treated NOD mice contained IgG antibodies directed against either the MSCs or cultured ICs that were used to generate the administered NIs. Sera from NI-treated, normoglycemic NOD mice contained neither IgG antibodies directed at MSCs nor at cultured ICs, while the i.p. administration of identical numbers of allogeneic (C57Bl/6), freshly isolated islets used as a positive control, elicited a robust antibody response (FIG. 23). The lack of an IgG antibody response to the cells that are used to form the allogeneic NIs, along with the achievement of long term euglycemia, further indicates that the NIs, as described herein, also provide humoral, allo-immune protection to their islet cell and MSC components.

Figure 24:
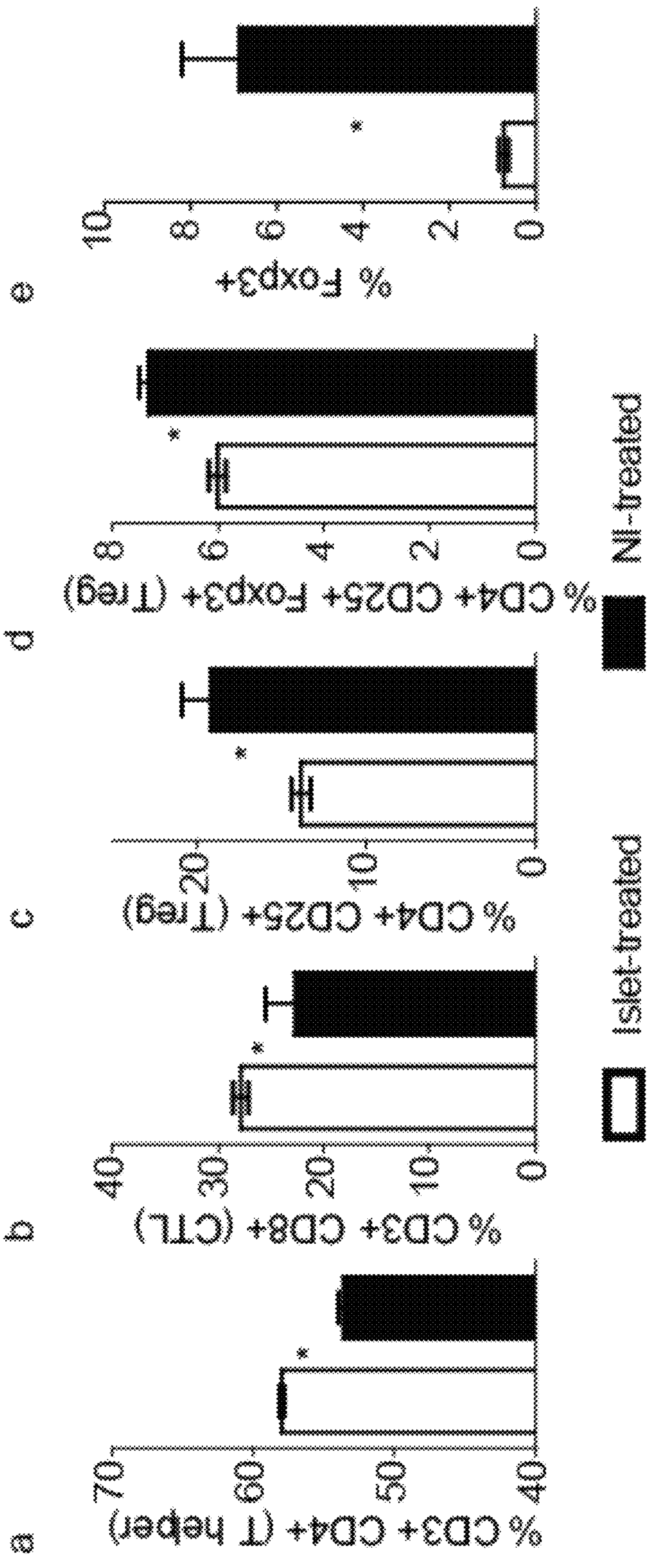
FIG. 24: Percent of helper, cytotoxic and regulatory T cells from spleens (a-d) and omenta (e) of islet-treated (N=3) vs. NI-treated NOD mice (N=3) 14 days post i.p. administration. For (a) and (b), shown are the percent of CD3+ cells that are also (a) CD4+ or (b) CD8+. For (c) and (d), shown are the percent of CD4+ cells that were also (c) CD25+ or (d) CD25+ Foxp3+. While the percentages of helper and cytotoxic T cells were lower in NI treated mice than in islet treated mice, the percentages of regulatory T cells were significantly increased, suggesting that NIs helped restore normoglycemia in NOD mice (see FIG. 2) in part through immune-modulation. (e) The percent of Foxp3 positive cells in Omenta of NI-treated NOD mice was markedly increased vs. islet treated animals. Omenta were stained for Foxp3, and percent of positive cells counted as described in Supplementary Information. *, P<0.05 vs. islet-treated group.

Inhibition of Autoimmune Response. Critical to effectively treating autoimmune T1DM with insulin producing cells is the autoimmune isolation of those cells, and the results presented in FIG. 9 imply that the ICs within the NIs are protected from the autoimmune attack of the treated NOD mice. Autoimmune destruction of beta cells in NOD mice is mediated, as in human T1DM, by autoreactive CD4+ Th1 cells, and is characterized by insulitis involving islet infiltration by macrophages, CD4+ and CD8+ T cells. It has previously been shown that allo-ASC administration either alone or with islets alleviates or prevents hyperglycemia in diabetic animals and humans in part by promoting expansion of regulatory T cells and suppressing expansion of immune cells through here confirmed Tgfb 1 expression (FIGS. 3, 8A and 8B) and IDO upregulation in dogs (FIG. 4C). To explore the possibility that the M/ASC component of the NIs protects the islet cells from the NOD mouse's autoimmune attack through similar mechanisms, we examined here a select set of known MSC immunomodulatory mechanisms as follows. We treated another group of diabetic NOD mice i.p. with allogeneic C57Bl/6 islets (N=3) or with allogeneic NIs (N=3). After 14 days, such mice were euthanized, and their blood, pancreata, kidneys, lungs, spleens and omenta were harvested. Pancreata were examined histologically and demonstrated to show insulitis as expected. Spleens were harvested and tested by FACS for the percentages of CD3, CD4, CD8, FOXP3, CD25 positive cells. Harvested omenta were examined by IHC for the presence of Foxp3+ cells. The percent of CD3/CD4 and CD3/CD8 double positive cells (helper and cytotoxic T Lymphocytes) were significantly lower in spleen cells of NI-treated vs. Islet treated NOD mice, while the percent of CD4/CD25 double positive and CD4/CD25/Foxp3 triple positive Tregs were significantly increased in the spleens of NI-treated vs. Islet treated NOD mice (FACS analysis, FIG. 24, Panels a-d). Similarly, IHC analysis of omenta of NI treated mice showed a significant increase in the percent of Foxp3 positive cells vs. those of vehicle treated mice (FIG. 24, Panel e). While the number of animals tested is small, these results are in agreement with others' findings and with our hypothesis that NIs, and specifically their M/ASC component, promotes euglycemia in T1-diabetic mice through modulation of the diabetogenic auto-immune response. Omenta from the above mice were also stained for Ki67 to examine whether there was significant cell division associated with NI grafts. None was found.

Conclusion: The above data indicate that administration of Neo-Islets does not elicit an antibody response to either cell type that composes the Neo-Islet, further supporting the hypothesis that the Neo-Islets provide immune isolation and eliminate the need for anti-rejection drugs and encapsulation devices.

Our extensive in vitro and in vivo data to date and presented above demonstrate that the treatment of experimental T1DM in mice with syngeneic and allogeneic Neo-Islets, and Neo-Islets from multiple species are able to effectively re-establish euglycemia, i.e., treat T1DM, and this during long-term follow-up. No Adverse Events, such as oncogenic transformation or ectopic mal-differentiation of Neo-Islets were observed. This novel therapy can be used as treatment of insulin-dependent diabetes both in companion animals (dogs, cats) and humans with type 1 diabetes mellitus.

Example 13: Treatment of Insulin-Dependent Diabetes Mellitus Using Neo-Islets Containing Allogeneic Islet Cells Neo-Islets containing human cells are generated as described in the above examples using ASCs and/or MSCs from a human subject identified as suffering from insulin-dependent Diabetes Mellitus and islet cells from an allogeneic source. The resulting Neo-Islets are administered to the subject. Several weeks after treatment, the subject displays improved glycemic control.

Example 14: Treatment of Insulin-Dependent Diabetes Mellitus Using Neo-Islets Containing Allogeneic Islet Cells and Allogeneic MSCs and/or ASCs Neo-Islets containing human cells are generated as described in the above examples using ASCs and/or MSCs and islet cells where stems cells and islet cells are from a source allogeneic to a human subject identified as suffering from insulin-dependent Diabetes Mellitus. The resulting Neo-Islets are administered to the subject. Several weeks after treatment, the subject displays improved glycemic control.

Example 15: Treatment of Insulin-Dependent Diabetes Mellitus Using Neo-Islets Containing Xenogeneic Islet Cells and/or Allogeneic MSCs and/or ASCs Neo-Islets containing human cells are generated as described in the above examples using ASCs and/or MSCs and islet cells where stems cells and/or islet cells are from a source xenogeneic to a human subject identified as suffering from insulin-dependent Diabetes Mellitus. The resulting Neo-Islets are administered to the subject. Several weeks after treatment, the subject displays improved glycemic control.

Example 16: Treatment of Insulin-Dependent Diabetes Mellitus Using Neo-Islets Containing Allogeneic Islet Cells and Adjuvant ASCs and/or MSCs Neo-Islets containing human cells are generated as described in the above examples using ASCs and/or MSCs from a human subject identified as suffering from insulin-dependent Diabetes Mellitus and islet cells from an allogeneic source. The resulting Neo-Islets are administered to the subject, and adjuvant human ASCs/MSCs are also administered to the subject. Several weeks after treatment, the subject displays improved glycemic control.

Example 17: Treatment of Insulin-Dependent Diabetes Mellitus Using Neo-Islets Containing Allogeneic Islet Cells and Allogeneic MSCs and/or ASCs and Adjuvant ASCs and/or MSCs Neo-Islets containing human cells are generated as described in the above examples using ASCs and/or MSCs and islet cells where stems cells and islet cells are from a source allogeneic to a human subject identified as suffering from insulin-dependent Diabetes Mellitus. The resulting Neo-Islets are administered to the subject, and adjuvant human ASCs/MSCs are also administered to the subject. Several weeks after treatment, the subject displays improved glycemic control.

Example 18: Treatment of Insulin-Dependent Diabetes Mellitus Using Neo-Islets Containing Xenogeneic Islet Cells and/or Allogeneic MSCs and/or ASCs and Adjuvant ASCs and/or MSCs Neo-Islets containing human cells are generated as described in the above examples using ASCs and/or MSCs and islet cells where stems cells and/or islet cells are from a source xenogeneic to a human subject identified as suffering from insulin-dependent Diabetes Mellitus. The resulting Neo-Islets are administered to the subject, and adjuvant human ASCs/MSCs are also administered to the subject. Several weeks after treatment, the subject displays improved glycemic control.

Example 19: Treatment of Insulin-Dependent Diabetes Mellitus Using Neo-Islets Containing Redifferentiated Islet Cells and/or Allogeneic MSCs and/or ASCs Neo-Islets containing human cells are generated as described in the above examples using ASCs and/or MSCs and islet cells where stems cells and/or islet cells are from a source allogeneic to a human subject identified as suffering from insulin-dependent Diabetes Mellitus. The Neo-Islets redifferentiated ex vivo. The redifferentiated Neo-Islets are administered to the subject. Several weeks after treatment, the subject displays improved glycemic control.

Example 20: Treatment of Insulin-Dependent Diabetes Mellitus Using Neo-Islets Containing Redifferentiated Islet Cells and/or Allogeneic MSCs and/or ASCs and Adjuvant ASCs and/or MSCs Neo-Islets containing human cells are generated as described in the above examples using ASCs and/or MSCs and islet cells where stems cells and/or islet cells are from a source allogeneic to a human subject identified as suffering from insulin-dependent Diabetes Mellitus. The Neo-Islets redifferentiated ex vivo. The redifferentiated Neo-Islets are administered to the subject, and adjuvant human ASCs/MSCs are also administered to the subject. Several weeks after treatment, the subject displays improved glycemic control.

Example 21: Treatment of Type 2 Diabetes Mellitus Using Neo-Islets Containing Allogeneic Islet Cells Insulin therapy has been used in patients suffering from type 2 diabetes mellitus, see, e.g., K. Horvath, K. Jeitler, A. Berghold, S. H. Ebrahim, T. W. Gratzer, J. Plank, T. Kaiser, T. R. Pieber, and A. Siebenhofer, "Long-acting insulin analogues versus NPH insulin (human isophane insulin) for type 2 diabetes mellitus," *Cochrane Database of Systematic Reviews* 2007, Issue 2 Art. No.: CD005613, DOI: 10.1002/14651858.CD005613.pub3, incorporated herein by reference. Neo-Islets containing human cells are generated as described in the foregoing Examples using ASCs and/or MSCs from a human subject identified as suffering from type 2 diabetes mellitus and islet cells from an allogeneic source. The resulting Neo-Islets are administered to the subject. Several weeks after treatment, the subject displays improved glycemic control. In the interim, the subject is treated with an oral hypoglycemic drug and/or insulin.

Example 22: Treatment of Type 2 Diabetes Mellitus Using Neo-Islets Containing Allogeneic Islet Cells and Allogeneic MSCs and/or ASCs Neo-Islets containing human cells are generated as described in the foregoing examples using ASCs and/or MSCs and islet cells where stems cells and islet cells are from a source allogeneic to a human subject identified as suffering from type 2 diabetes mellitus. The resulting Neo-Islets are administered to the subject. Several weeks after treatment, the subject displays improved glycemic control. In the interim, the subject is treated with an oral hypoglycemic drug and/or insulin.

Example 23: Treatment of Type 2 Diabetes Mellitus Using Neo-Islets Containing Xenogeneic Islet Cells and/or Allogeneic MSCs and/or ASCs Neo-Islets containing human cells are generated as described in the foregoing examples using ASCs and/or MSCs and islet cells where stems cells and/or islet cells are from a source xenogeneic to a human subject identified as suffering from type 2 diabetes mellitus. The resulting Neo-Islets are administered to the subject. Several weeks after treatment, the subject displays improved glycemic control. In the interim, the subject is treated with an oral hypoglycemic drug and/or insulin.

Example 24: Treatment of Type 2 Diabetes Mellitus Using Neo-Islets Containing Allogeneic Islet Cells and Adjuvant ASCs and/or MSCs Neo-Islets containing human cells are generated as described in the foregoing examples using ASCs and/or MSCs from a human subject identified as suffering from type 2 diabetes mellitus and islet cells from an allogeneic source. The resulting Neo-Islets are administered to the subject, and adjuvant human ASCs/MSCs are also administered to the subject. Several weeks after treatment, the subject displays improved glycemic control. In the interim, the subject is treated with an oral hypoglycemic drug and/or insulin.

Example 25: Treatment of Type 2 Diabetes Mellitus Using Neo-Islets Containing Allogeneic Islet Cells and Allogeneic MSCs and/or ASCs and Adjuvant ASCs and/or MSCs Neo-Islets containing human cells are generated as described in the foregoing examples using ASCs and/or MSCs and islet cells where stems cells and islet cells are from a source allogeneic to a human subject identified as suffering from type 2 diabetes mellitus. The resulting Neo-Islets are administered to the subject, and adjuvant human ASCs/MSCs are also administered to the subject. Several weeks after treatment, the subject displays improved glycemic control. In the interim, the subject is treated with an oral hypoglycemic drug and/or insulin.

Example 26: Treatment of Type 2 Diabetes Mellitus Using Neo-Islets Containing Xenogeneic Islet Cells and/or Allogeneic MSCs and/or ASCs and Adjuvant ASCs and/or MSCs Neo-Islets containing human cells are generated as described in the foregoing examples using ASCs and/or MSCs and islet cells where stems cells and/or islet cells are from a source xenogeneic to a human subject identified as suffering from type 2 diabetes mellitus. The resulting Neo-Islets are administered to the subject, and adjuvant human ASCs/MSCs are also administered to the subject. Several weeks after treatment, the subject displays improved glycemic control. In the interim, the subject is treated with an oral hypoglycemic drug and/or insulin.

Example 27: Treatment of Type 2 Diabetes Mellitus Using Neo-Islets Containing Redifferentiated Islet Cells and/or Allogeneic MSCs and/or ASCs Neo-Islets containing human cells are generated as described in the foregoing examples using ASCs and/or MSCs and islet cells where stems cells and/or islet cells are from a source allogeneic to a human subject identified as suffering from type 2 Diabetes Mellitus. The Neo-Islets redifferentiated ex vivo. The redifferentiated Neo-Islets are administered to the subject. Several weeks after treatment, the subject displays improved glycemic control. In the interim, the subject is treated with an oral hypoglycemic drug and/or insulin.

Example 28: Treatment of Type 2 Diabetes Mellitus Using Neo-Islets Containing Redifferentiated Islet Cells and/or Allogeneic MSCs and/or ASCs and Adjuvant ASCs and/or MSCs Neo-Islets containing human cells are generated as described in the foregoing examples using ASCs and/or MSCs and islet cells where stems cells and/or islet cells are from a source allogeneic to a human subject identified as suffering from type 2 diabetes mellitus. The Neo-Islets redifferentiated ex vivo. The redifferentiated Neo-Islets are administered to the subject, and adjuvant human ASCs/MSCs are also administered to the subject. Several weeks after treatment, the subject displays improved glycemic control. In the interim, the subject is treated with an oral hypoglycemic drug and/or insulin.

Example 29: Administration of Neo-Islets

Neo-Islets generated as described in any one of the foregoing examples where the Neo-Islet is administered intravenously to the subject suffering insulin-dependent diabetes mellitus. Several weeks after treatment, the subject displays improved glycemic control.

Example 30: Administration of Neo-Islets

Neo-Islets generated as described in any one of the foregoing examples where the Neo-Islet is administered intravenously to the subject suffering type 2 diabetes mellitus. Several weeks after treatment, the subject displays improved glycemic control.

Example 31: Administration of Neo-Islets

Neo-Islets generated as described in any one of the foregoing examples where the Neo-Islet is administered subcutaneously to the subject suffering insulin-dependent diabetes mellitus. Several weeks after treatment, the subject displays improved glycemic control.

Example 32: Administration of Neo-Islets

Neo-Islets generated as described in any one of the foregoing examples where the Neo-Islet is administered subcutaneously to the subject suffering type 2 diabetes mellitus. Several weeks after treatment, the subject displays improved glycemic control.

Example 33: Treatment of Prediabetes Mellitus Using Neo-Islets

Neo-Islets generated as described in any one of the foregoing examples are administered to the subject suffering from impaired glucose tolerance or Prediabetes. Several weeks after treatment, the subject displays improved glycemic control.

REFERENCES (THE CONTENTS OF THE ENTIRETY OF EACH OF WHICH ARE INCORPORATED HEREIN BY THIS REFERENCE)

ADDIN Mendeley Bibliography CSL_BIBLIOGRAPHY 1. Hara M., X. Wang, T. Kawamura, V.P. Bindokas, R. F. Dizon, S. Y. Alcoser, M. A. Magnuson, and G. I. Bell: Transgenic mice with green fluorescent protein-labeled pancreatic beta-cells. *Am. J. Physiol. Endocrinol. Metab.* 284:E177-E183, 2003.

2. Zhou X., K. Merchak, W. Lee, J. P. Grande, M. Cascalho, and J. L. Platt: Cell Fusion Connects Oncogenesis with Tumor Evolution. *Am. J. Pathol.* 185:2049-60, 2015.
3. DelaRosa O., B. Sanchez-Correa, S. Morgado, C. Ramirez, B. del Rio, R. Menta, E. Lombardo, R. Tarazona, and J. G. Casado: Human Adipose-Derived Stem Cells Impair Natural Killer Cell Function and Exhibit Low Susceptibility to Natural Killer-Mediated Lysis. *Stem Cells Dev.* 21:1333-1343, 2012.
4. Burr S. P., F. Dazzi, 0. Garden: Mesenchymal stromal cells and regulatory T cells: the Yin and Yang of peripheral tolerance? *Immunol. Cell Biol.* 91:12-8, 2013.
5. English K: Mechanisms of mesenchymal stromal cell immunomodulation. *Immunol. Cell Biol.* 91:19-26, 2012.
6. Kim Y.-H., Y.-M. Wee, M.-Y. Choi, D.-G. Lim, S.-C. Kim, D.-J. Han: Interleukin (IL)-10 induced by CD11b(+) cells and IL-10-activated regulatory T cells play a role in immune modulation of mesenchymal stem cells in rat islet allografts. *Mol. Med.* 17:697-708, 2011.
7. Spaggiari G. M., L. Moretta: Cellular and molecular interactions of mesenchymal stem cells in innate immunity. *Immunol. Cell Biol.* 91:27-31, 2013.
8. Le Blanc K., L.C. Davies: Mesenchymal stromal cells and the innate immune response. *Immunol.* Lett. in press: 2015 May 15. pii: S0165-2478(15)00072-3. doi: 10.1016/j.imlet.2015.05.004. [Epub ahead of print].
9. Plock J. A., J. T. Schnider, W. Zhang, R. Schweizer, W. Tsuji, N. Kostereva, P. M. Fanzio, S. Ravuri, M. G. *Solari*, H.-Y. Cheng, P. J. Rubin, K. G. Marra, V. S. Gorantla: Adipose- and Bone Marrow-Derived Mesenchymal Stem Cells Prolong Graft Survival in Vascularized Composite Allotransplantation. *Transplantation* 99(9):1765-73: 2015.
10. Vrabelova D., C. A. Adin, A. Kenzig, C. Gilor, F. Xu, J. L. Buss, A. Rajab: Evaluation of a high-yield technique for pancreatic islet isolation from deceased canine donors. *Domest. Anim. Endocrinol.* 47:119-26, 2014.
11. Woolcott O.O., R. N. Bergman, J. M. Richey, E. L. Kirkman, L. N. Harrison, V. lonut, M. Lottati, D. Zheng, I. R. Hsu, D. Vski, M. Kabir, S. P. Kim, K. J. Catalano, J. D. Chiu, and R. H. Chow: Simplified method to isolate highly pure canine pancreatic islets. *Pancreas* 41:31-8, 2012.
12. Lange C., F. Rigel, H. Ittrich, F. Clayton, C. Nolte-Ernsting, A. R. Zander, and C. Westenfelder: Administered mesenchymal stem cells enhance recovery from ischemia/reperfusion-induced acute renal failure in rats. *Kidney Int.* 68:1613-7, 2005.
13. Rigel F., Z. Hu, K. Weiss, J. Isaac, C. Lange, and C. Westenfelder: Administered mesenchymal stem cells protect against ischemic acute renal failure through differentiation-independent mechanisms. *Am. J. Physiol. Renal Physiol.* 289:F31-42, 2005.
14. Rigel F., K. Weiss, Y. Yang, Z. Hu, P. Zhang, and C. Westenfelder: Vasculotropic, paracrine actions of infused mesenchymal stem cells are important to the recovery from acute kidney injury. *Am. J. Physiol. Renal Physiol.* 292:F1626-35, 2007.
15. Pittenger M. F., A.M. Mackay, S. C. Beck, R. K. Jaiswal, R. Douglas, J. D. Mosca, M. A. Moorman, D. W. Simonetti, S. Craig, and D. R. Marshak: Multilineage potential of adult human mesenchymal stem cells. *Science* 284: 143-7, 1999.
16. Crop M. J., C. C. Baan, S. S. Korevaar, J. N. M. IJzermans, I. P. J. Alwayn, W. Weimar, and M. J. Hoogduijn: Donor-Derived Mesenchymal Stem Cells Suppress Alloreactivity of Kidney Transplant Patients. *Transplantation* 87:896-906, 2009.

What is claimed is:

1. A composition comprising suspended cell clusters, wherein the cell clusters comprise:

i) insulin expressing cells; and ii) mesenchymal stem cells or adipose stem cells;

wherein the cell clusters are suspended in a medium; and wherein at least 69.77% of the nearest neighbors of the mesenchymal stem cells or adipose stem cells are insulin expressing cells.

2. The composition of claim 1, wherein the ratio of insulin expressing cells to mesenchymal stem cells or adipose stem cells is from about 1:2 to about 2:1.

3. The composition of claim 1, wherein the insulin expressing cells and stem cells are present in the clusters at an insulin expressing cell: stem cell ratio of about 1:100, 1:75, 1:50, 1:25, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 25:1, 50:1, 75:1, or 100:1.

4. The composition of claim 1, wherein the cell clusters are approximately the size of an islet found in the pancreas.

5. The composition of claim 1, wherein the ratio of insulin expressing cells to mesenchymal stem cells or adipose stem cells is about 1:1.

6. The composition of claim 1, wherein the clusters are approximately 150 μm in diameter.

7. The composition of claim 1, wherein the cell clusters comprise about 1,000 cells per cluster.

8. The composition of claim 1, wherein the medium comprises serum or platelet lysate.

9. The composition of claim 1, wherein the insulin expressing cells and the mesenchymal stem cells or adipose stem cells are stochastically distributed throughout the cell cluster.

* * * * *